(12) United States Patent
Langkopf et al.

(10) Patent No.: US 8,163,911 B2
(45) Date of Patent: Apr. 24, 2012

(54) ARYLSULFONYLAMINOMETHYLPHOSPHONIC ACID DERIVATIVES, THE PREPARATION THEREOF AND THE USE THEREOF AS PHARMACEUTICAL COMPOSITIONS

(75) Inventors: Elke Langkopf, Warthausen (DE);
Alexander Pautsch, Ulm (DE);
Corinna Schoelch, Mittelbiberach (DE);
Annette Schuler-Metz, Ulm (DE);
Ruediger Streicher, Biberach (DE);
Holger Wagner, Mettenberg (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 12/676,319

(22) PCT Filed: Sep. 4, 2008

(86) PCT No.: PCT/EP2008/061651
§ 371 (c)(1),
(2), (4) Date: May 7, 2010

(87) PCT Pub. No.: WO2009/030715
PCT Pub. Date: Mar. 12, 2009

(65) Prior Publication Data
US 2010/0261677 A1    Oct. 14, 2010

(30) Foreign Application Priority Data
Sep. 5, 2007   (DE) .................. 10 2007 042 154

(51) Int. Cl.
C07F 9/28    (2006.01)

(52) U.S. Cl. .......... 546/23; 514/232; 514/244; 514/337; 548/113; 548/119; 548/413; 558/175; 558/386; 562/16

(58) Field of Classification Search .................. None
See application file for complete search history.

(56) References Cited

U.S. PATENT DOCUMENTS

| | | | |
|---|---|---|---|
| 6,812,250 B2 | 11/2004 | Defossa et al. | |
| 7,138,414 B2 | 11/2006 | Schoenafinger et al. | |
| 7,223,796 B2 | 5/2007 | Defossa et al. | |
| 7,262,220 B2 | 8/2007 | Defossa et al. | |
| 7,989,622 B2 | 8/2011 | Bajjalieh et al. | |
| 2006/0142250 A1 | 6/2006 | Blaskovich et al. | |
| 2010/0093703 A1 | 4/2010 | Wagner et al. | |
| 2010/0130557 A1 | 5/2010 | Wagner et al. | |
| 2010/0210594 A1 | 8/2010 | Wagner et al. | |
| 2010/0210595 A1 | 8/2010 | Wagner et al. | |

FOREIGN PATENT DOCUMENTS

| | | |
|---|---|---|
| EP | 0604657 A1 | 7/1994 |
| EP | 0638581 A1 | 2/1995 |
| EP | 1074542 A1 | 2/2001 |
| JP | 2005206492 A | 8/2005 |
| WO | 9928297 A1 | 6/1999 |
| WO | 0170754 A1 | 9/2001 |
| WO | 02096864 A1 | 12/2002 |
| WO | 03084922 A1 | 10/2003 |
| WO | 2004007437 A1 | 1/2004 |
| WO | 2004007455 A1 | 1/2004 |
| WO | 2004104001 A2 | 12/2004 |
| WO | 2005013976 A1 | 2/2005 |
| WO | 2005013977 A1 | 2/2005 |
| WO | 2005013978 A1 | 2/2005 |
| WO | 2005024535 A2 | 3/2005 |
| WO | 2006034418 A2 | 3/2006 |
| WO | 2007044729 A2 | 4/2007 |
| WO | 2008099000 A2 | 2/2008 |
| WO | 2008103354 A2 | 2/2008 |
| WO | 2008113760 A2 | 9/2008 |
| WO | 2009016118 A1 | 2/2009 |
| WO | 2009016119 A1 | 2/2009 |
| WO | 2009030715 A1 | 3/2009 |

OTHER PUBLICATIONS

Martin, Yvonne C. et al., Do Structurally Similar Molecules Have Similar Biological Activity?, 45 J. Med. Chem. 4350-4358 (2002).*
Chen et al., Discovering Benzamide Derivatives as Glycogen Phosphorylase Inhibitors and Their Binding Site at the Enzyme, 15 Bioorg. & Med. Chem. 6763-6774 (2007).*
International Search Report, Form PCT/ISA/210, for corresponding PCT/EP2008/061651; date of mailing: Dec. 1, 2008.
Abstract in English for JP200506492 cited herein.
International Search Report for PCT/EP2008/051824 mailed May 8, 2009.
International Search Report for PCT/EP2008/053087 mailed Sep. 5, 2008.
International Search Report for PCT/EP2008/059805 mailed Nov. 6, 2008.
International Search Report for PCT/EP2008/059807 mailed Nov. 12, 2008.

(Continued)

*Primary Examiner* — Janet Andres
*Assistant Examiner* — Timothy R Rozof
(74) *Attorney, Agent, or Firm* — Michael P. Morris; Mary-Ellen M. Devlin; Usha R. Patel

(57) ABSTRACT

The invention relates to substituted arylsulphonylaminomethylphosphonic acid derivatives of general formula (I) wherein the groups $R^a$ to $R^f$, A and Z are defined as mentioned in the specification and claims, which are suitable for preparing a medicament for the treatment of metabolic disorders, particularly type 1 or type 2 diabetes mellitus.

(I)

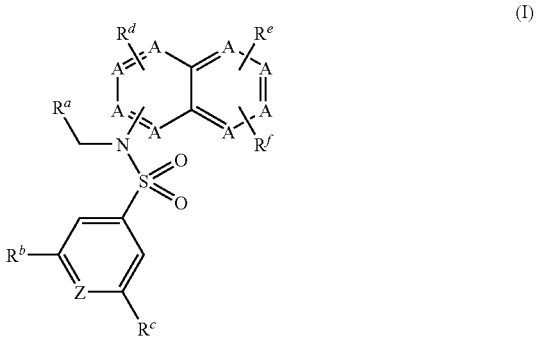

4 Claims, No Drawings

OTHER PUBLICATIONS

Jordan, V Craig, "Tamoxifen: A Most Unlikely Pioneering Medicine" Nature Reviews Drug Discovery, vol. 2, Mar. 2003, pp. 205-213.

Cohen, Philip "The Twentieth Centry Struggle to Decipher Insulin Signalling" Nature Reviews Molecular Cell Biology, vol. 7, Nov. 2006, pp. 867-874.

Zibrova, Darya et al., "Inhibition of the interaction between protein phosphatase 1 glycogen-targeting subunit and glycogen phosphorylase increases glycogen synthesis in primary rat hepatocytes" Biochem Journal, 2008, 412, pp. 359-365.

WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pages: 681. This PCT publication is too large for EFS submission via the foreign patent section, therefore submitting in two parts in the NPL section. PP. 1-340.

WO2006052722 (Part 1 of 2) International Publication Date: May 18, 2006. Applicant: Smithkline Beecham Corporation, Inventors: Evans, Karen et al., Title: "Glycogen Phosphorylase Inhibitor Compounds and Pharmaceutical Compositions Thereof" Total pages. 681. This PCT publication is too large for EFS submission via the foreign patent section, therefore submitting in two parts in the NPL section. PP. 341-681.

* cited by examiner

ARYLSULFONYLAMINOMETHYLPHOS-PHONIC ACID DERIVATIVES, THE PREPARATION THEREOF AND THE USE THEREOF AS PHARMACEUTICAL COMPOSITIONS

The present invention relates to new substituted arylsulphonylaminomethylphosphonic acid derivatives of general formula

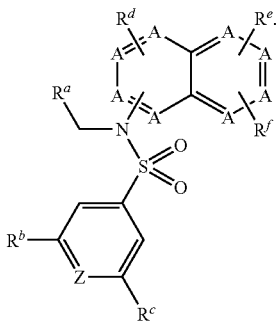

(I)

wherein the groups $R^a$ to $R^f$, A and Z are defined as hereinafter, including the tautomers, stereoisomers, mixtures thereof and salts thereof. This invention further relates to pharmaceutical compositions containing a compound of formula (I) according to the invention as well as the use of a compound according to the invention for preparing a pharmaceutical composition for the treatment of metabolic disorders, particularly type 1 or type 2 diabetes mellitus. The invention also relates to processes for preparing a pharmaceutical composition as well as a compound according to the invention.

Compounds of formula (I) are suitable for preventing the inhibiting effect of glycogen phosphorylase on the activity of glycogen synthase by stopping the interaction of glycogen phosphorylase a with the $G_L$ subunit of glycogen-associated protein phosphatase 1 (PP1). Compounds with these properties stimulate glycogen synthesis and are proposed for the treatment of metabolic disorders, particularly diabetes (P. Cohen, *Nature Reviews Molecular Cell Biology* 2006, 7, 867-874).

AIM OF THE INVENTION

The aim of the present invention is to provide new arylsulphonylaminomethylphosphonic acid derivatives that suppress the interaction of glycogen phosphorylase a with the $G_L$ subunit of glycogen-associated protein phosphatase 1 (PP1).

A further aim of the present invention is to provide new pharmaceutical compositions that are suitable for the prevention and/or treatment of metabolic disorders, particularly diabetes.

Another aim of this invention is to provide a process for preparing the compounds according to the invention.

Other aims of the present invention will become directly apparent to the skilled man from the foregoing remarks and those that follow.

OBJECT OF THE INVENTION

In a first aspect the present invention relates to new substituted arylsulphonylaminomethylphosphonic acid derivatives of general formula:

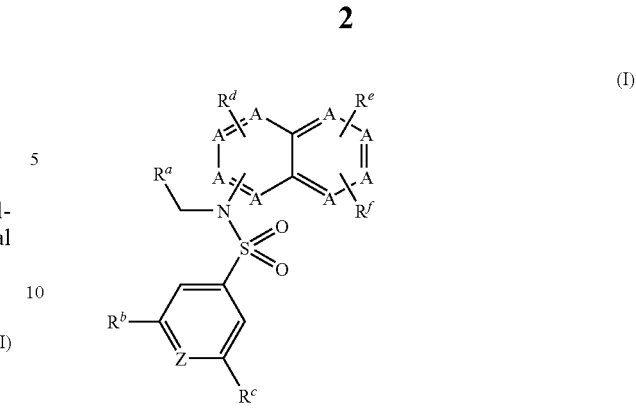

(I)

In the above formula (I)

$R^a$ denotes a phosphonic acid group $PO(OH)_2$ or a group that may be converted in vivo into a phosphonic acid group, $R^b$ and $R^c$ independently of one another denote H, halogen, cyano, $C_{1-3}$-alkyl, $C_{2-3}$-alkenyl, $C_{2-3}$-alkynyl, $C_{1-3}$-fluoroalkyl, $C_{1-3}$-perfluoroalkyl, $C_{1-3}$-alkoxy, $C_{1-3}$-fluoroalkoxy, $C_{1-3}$-perfluoroalkoxy, hydroxy, amino or nitro, A denotes CH or N, while in all not more than four nitrogen atoms may be present in the bicyclic system, Z denotes CH, CF or N and $R^d$ denotes H, halogen, cyano, hydroxy, nitro, $C_{1-6}$-alkyl, $C_{2-6}$-alkenyl, $C_{2-6}$-alkynyl, $C_{1-6}$-fluoroalkyl, $C_{1-6}$-perfluoroalkyl, $C_{3-7}$-cycloalkyl, heterocylcoalkyl, aryl, heteroaryl, $C_{1-6}$-alkoxy, $C_{1-6}$-fluoroalkoxy, $C_{1-6}$-perfluoroalkoxy, $C_{3-7}$-cycloalkyloxy, heterocylcoalkyloxy, aryloxy, heteroaryloxy, $C_{1-6}$-alkylsulphanyl, $C_{3-7}$-cycloalkylsulphanyl or a group selected from among $R^1R^2N$, $R^1R^2N$—CO, $R^1R^2N$—CO—$NR^3$, $R^1R^2N$—SO, $R^1R^2N$—$SO_2$, $R^1R^2N$—$SO_2$—$NR^3$, $R^4$—CO, $R^4$—CO—$NR^3$, $R^5$—SO, $R^5$—SO—$NR^3$, $R^5$—$SO_2$, $R^5$—$SO_2$—$NR^3$ or $R^5$—CO—O—, wherein $R^1$ denotes H, $C_{1-6}$-alkyl, $C_{3-7}$-cycloalkyl, heterocylcoalkyl, aryl or heteroaryl, $R^2$ denotes H, $C_{1-6}$-alkyl, $C_{3-7}$-cycloalkyl, heterocylcoalkyl, aryl or heteroaryl, $R^3$ denotes H, $C_{1-6}$-alkyl or $C_{3-7}$-cycloalkyl, $R^4$ denotes $C_{1-6}$-alkyl, $C_{3-7}$-cycloalkyl, heterocylcoalkyl, aryl, heteroaryl, hydroxy, or $C_{1-6}$-alkyloxy and $R^5$ denotes $C_{1-6}$-alkyl, $C_{3-7}$-cycloalkyl, heterocylcoalkyl, aryl or heteroaryl, and $R^e$ and $R^f$ have the same meaning as $R^d$ hereinbefore, while the groups $R^d$, $R^e$ and $R^f$ may be identical or different, while the $C_{1-6}$-alkyl, $C_{2-6}$-alkenyl, $C_{2-6}$-alkynyl, $C_{3-7}$-cycloalkyl, $C_{1-6}$-alkyloxy- and $C_{3-7}$-cycloalkyloxy groups contained in the groups mentioned hereinbefore for $R^d$, $R^e$, $R^f$ as well as $R^1$ to $R^5$ groups may each be monosubstituted or independently of one another di- or trisubstituted in the carbon skeleton by a group selected from among cyano, hydroxy, $C_{3-7}$-cycloalkyl, heterocylcoalkyl, aryl, heteroaryl, $C_{1-6}$-alkoxy, $C_{1-6}$-perfluoroalkoxy, $C_{3-7}$-cycloalkyloxy, heterocylcoalkyloxy, aryloxy, heteroaryloxy, or a group selected from among $R^6R^7N$, $R^6R^7N$—CO, $R^6R^7N$—CO—$NR^8$, $R^6R^7N$—$SO_2$—$NR^8$, $R^9$—CO, $R^9$—CO—$NR^8$, $R^{10}$—$SO_2$, $R^{10}$—$SO_2$—$NR^8$ or $R^{10}$—CO—O, wherein $R^6$ denotes H, $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl or heteroaryl-$C_{1-4}$-alkyl, $R^7$ denotes H, $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl or heteroaryl-$C_{1-4}$-alkyl, $R^8$ denotes H, $C_{1-4}$-alkyl, $C_{3-6}$-cycloalkyl or $C_{3-6}$-cycloalkyl-$C_{1-4}$-alkyl, $R^9$ denotes $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl, heteroaryl-$C_{1-4}$-alkyl, hydroxy or $C_{1-4}$-alkyloxy and $R^{10}$ denotes $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl or heteroaryl-$C_{1-4}$-alkyl, while the above-mentioned substituents must not be bound to a common carbon atom and heteroatoms must be separated from one another by at least two carbon atoms, and the aryl, heteroaryl, aryloxy- and heteroaryloxy groups contained in the groups mentioned above for $R^d$, $R^e$ as well as $R^1$ to $R^5$ may each be monosubstituted or independently of one another di- or trisubstituted in the carbon skeleton by a group selected from among halogen, cyano, hydroxy, nitro, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-4}$-alkyl, $C_{1-6}$-fluoroalkyl, $C_{1-6}$-perfluoroalkyl, $C_{1-6}$-alkoxy, $C_{1-6}$-fluoroalkoxy, $C_{1-6}$-perfluoroalkoxy, $C_{3-7}$-cycloalkyloxy, $C_{3-7}$-cycloalkyl-$C_{1-4}$-alkyloxy, heterocylcoalkyloxy, heterocylcoalkyl-$C_{1-4}$-alkyloxy $C_{1-6}$-alkylsulphanyl, $C_{3-7}$-cycloalkylsulphanyl, or a group selected from among $R^6R^7N$, $R^6R^7N$—CO, $R^6R^7N$—CO—$NR^8$, $R^6R^7N$—SO, $R^6R^7N$—$SO_2$, $R^6R^7N$—$SO_2$—$NR^8$, $R^9$—CO, $R^9$—CO—$NR^8$, $R^{10}$—SO, $R^{10}$—SO—$NR^8$, $R^{10}$—$SO_2$, $R^{10}$—$SO_2$—$NR^8$ or $R^{10}$—CO—O, wherein $R^6$ to $R^{10}$ are as hereinbefore defined.

The invention also relates to the tautomers, stereoisomers, mixtures and salts, particularly the physiologically acceptable salts, of the compounds according to the invention.

The compounds of general formula I according to the invention and the physiologically acceptable salts thereof have valuable pharmacological properties, in particular they suppress the interaction of glycogen phosphorylase a with the $G_L$-subunit of glycogen-associated protein phosphatase 1 (PP1).

Therefore this invention also relates to the use of the compounds according to the invention, including the physiologically acceptable salts, as pharmaceutical compositions.

This invention further relates to pharmaceutical compositions containing at least one compound according to the invention or a physiologically acceptable salt according to the invention, optionally together with one or more inert carriers and/or diluents.

A further object of this invention is the use of at least one compound according to the invention or a physiologically acceptable salt of such a compound for preparing a pharmaceutical composition that is suitable for the treatment or prevention of diseases or conditions that can be influenced by suppressing the interaction of glycogen phosphorylase a with the $G_L$-subunit of glycogen-associated protein phosphatase 1 (PP1).

The invention also relates to the use of at least one compound according to the invention for preparing a pharmaceutical composition which is suitable for the treatment of metabolic disorders, for example type I or II diabetes mellitus.

The invention also relates to the use of at least one compound according to the invention for preparing a pharmaceutical composition for suppressing the interaction of glycogen phosphorylase a with the $G_L$-subunit of glycogen-associated protein phosphatase 1 (PP1).

A further object of this invention is a process for preparing a pharmaceutical composition according to the invention, characterised in that a compound according to the invention is incorporated in one or more inert carriers and/or diluents by a non-chemical method.

The present invention also relates to a process for preparing the compounds of general formula (I) according to the invention.

DETAILED DESCRIPTION OF THE INVENTION

Unless stated otherwise, the groups, radicals and substituents, particularly $R^a$ to $R^f$, $R^1$ to $R^{10}$, A and Z, have the meanings given hereinbefore and hereinafter.

If groups, substituents or radicals occur more than once in a compound, they may have the same or different meanings.

Preferred compounds of the above general formula (I) are those wherein $R^a$, $R^b$, $R^c$, A, Z, $R^d$ and $R^e$ are as hereinbefore defined, and $R^f$ denotes H or $C_{1-3}$-alkyl.

Particularly preferred compounds of the above general formula (I) are those wherein the bicyclic heteroaromatic group

(II)

denotes naphthaline, quinoline, isoquinoline, quinazoline, quinoxaline, cinnoline, phthalazine, [1,5]naphthyridine, [1,8]naphthyridine, pyrido[3,2-d]pyrimidine, pyrimido[5,4-d]pyrimidine, or pteridine, and $R^a$ denotes a group of formula $PO(OH)_2$, wherein one or two OH groups in each case may be replaced by
  a $C_{1-4}$-alkoxy group, which is substituted in the alkyl moiety by a $C_{1-4}$-alkyl-carbonyloxy or $C_{1-4}$-alkoxy-carbonyloxy group, or by
  a $C_{1-3}$-alkylamino group, which is substituted in the alkyl moiety by a $C_{1-3}$-alkoxy-carbonyl group.

$R^b$ and $R^c$ independently of one another denote halogen, cyano, $C_{1-3}$-alkyl, $C_{2-3}$-alkenyl, $C_{2-3}$-alkynyl, $C_{1-3}$-fluoroalkyl, $C_{1-3}$-perfluoroalkyl, $C_{1-2}$-alkoxy, $C_{1-2}$-fluoroalkoxy, $C_{1-2}$-perfluoroalkoxy, amino or nitro, Z denotes CH, CF or N, $R^d$ denotes H, halogen, cyano, hydroxy, nitro, $C_{1-4}$-alkyl, $C_{2-4}$-alkenyl, $C_{2-4}$-alkynyl, aryl-$C_{2-3}$-alkynyl, $C_{1-4}$-fluoroalkyl, $C_{1-4}$-perfluoroalkyl, $C_{3-6}$-cycloalkyl, $C_{3-6}$-cycloalkyl-$C_{1-4}$-alkyl, heterocylcoalkyl, heterocycloalkyl-$C_{1-4}$-alkyl, aryl, aryl-$C_{1-4}$-alkyl, heteroaryl, heteroaryl-$C_{1-4}$-alkyl, $C_{1-4}$-alkoxy, $C_{1-4}$-fluoroalkoxy, $C_{1-4}$-perfluoroalkoxy, $C_{3-6}$-cycloalkyloxy, $C_{3-6}$-cycloalkyl-$C_{1-4}$-alkyloxy, heterocylcoalkyloxy, heterocylcoalkyl-$C_{1-4}$-alkoxy, aryloxy, aryl-$C_{1-4}$-alkyloxy, heteroaryloxy, heteroaryl-$C_{1-4}$-alkyloxy, $C_{1-4}$-alkylsulphanyl, $C_{3-6}$-cycloalkylsulphanyl, or a group selected from among $R^1R^2N$, $R^1R^2N$—CO, $R^1R^2N$—CO—$NR^3$, $R^1R^2N$—SO, $R^1R^2N$—$SO_2$, $R^1R^2N$—$SO_2$—$NR^3$, $R^4$—CO, $R^4$—CO—$NR^3$, $R^5$—SO, $R^5$—SO—$NR^3$, $R^5$—$SO_2$ or $R^5$—$SO_2$—$NR^3$, wherein R¹ denotes H, $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl, heteroaryl-$C_{1-4}$-alkyl, R² denotes H, $C_{1-4}$-alkyl, $C_{3-6}$-cycloalkyl, $C_{3-6}$-cycloalkyl-$C_{1-4}$-alkyl, heterocylcoalkyl, heterocylcoalkyl-$C_{1-4}$-alkyl, aryl, aryl-$C_{1-4}$-alkyl, heteroaryl or heteroaryl-$C_{1-4}$-alkyl, R³ denotes H, $C_{1-4}$-alkyl, $C_{3-6}$-cycloalkyl or $C_{3-6}$-cycloalkyl-$C_{1-4}$-alkyl, R⁴ denotes $C_{1-4}$-alkyl, $C_{3-6}$-cycloalkyl, $C_{3-6}$-cycloalkyl-$C_{1-4}$-alkyl, heterocylcoalkyl, aryl, aryl-$C_{1-4}$-alkyl, heteroaryl, heteroaryl-$C_{1-4}$-alkyl, hydroxy or $C_{1-4}$-alkyloxy and R⁵ denotes $C_{1-4}$-alkyl, $C_{3-6}$-cycloalkyl, heterocylcoalkyl, aryl, aryl-$C_{1-4}$-alkyl, heteroaryl, heteroaryl-$C_{1-4}$-alkyl,
and $R^e$ has the meaning given for $R^d$ hereinbefore, with the proviso that at least one of the groups $R^d$ and $R^e$ must be H or $C_{1-3}$-alkyl, and $R^f$ denotes H or $C_{1-3}$-alkyl.

Particularly preferred are those compounds of the above general formula (I), wherein
the bicyclic heteroaromatic group of general formula (II) denotes naphthalene, quinoline, isoquinoline, quinazoline, quinoxaline or cinnoline, $R^a$ denotes a group of formula $PO(OH)_2$, wherein one or two OH groups in each case may be replaced by
a $C_{1-2}$-alkoxy group, which is substituted in the alkyl moiety by a $C_{1-4}$-alkyl-carbonyloxy or $C_{1-4}$-alkoxy-carbonyloxy group, or by
a $C_{1-3}$-alkylamino group, which is substituted in the alkyl moiety by a $C_{1-3}$-alkoxy-carbonyl group, $R^b$ and $R^c$ independently of one another denote fluorine, chlorine, bromine, cyano, $C_{1-2}$-alkyl, ethynyl, trifluoromethyl, methoxy, amino or nitro, Z denotes CH or CF and $R^d$ denotes H, fluorine, chlorine, bromine, cyano, $C_{1-3}$-alkyl, $C_{2-3}$-alkynyl, aryl, heteroaryl, aryl-$C_{2-3}$-alkynyl, $C_{1-3}$-alkoxy, arylcarbonyl, di-($C_{1-3}$-alkyl)-aminosulphonyl,
5- to 7-membered cycloalkyleneimino-carbonyl,
aminocarbonyl, wherein one or two hydrogen atoms independently of one another may be replaced in each case by a $C_{1-3}$-alkyl or aryl-($C_{1-3}$-alkyl)-group, or
amino, which may be substituted by one or two $C_{1-3}$-alkyl groups or an aryl-$C_{1-3}$-alkylcarbonyl or arylaminocarbonyl group,
while by an aryl group is meant a phenyl group which may optionally be substituted by a cyano group,
and by a heteroaryl group is meant a 5-methyl-[1,2,4]oxadiazolyl, benzoxazolyl, benzothiazolyl or pyrimidinyl group, $R^e$ has the meaning given hereinbefore for $R^d$ with the proviso that at least one of the groups $R^d$ and $R^e$ must be H or $C_{1-3}$-alkyl, and $R^f$ denotes H or $C_{1-3}$-alkyl.

Most particularly preferred are those compounds of the above general formula (I) wherein
the bicyclic heteroaromatic group of formula (II) denotes naphthalene, quinoline, quinazoline, quinoxaline or cinnoline, $R^a$ denotes a group of formula $PO(OH)_2$, wherein one or two OH groups may be replaced in each case by a tert.-butyl-carbonyloxy-methoxy, iso-propyloxy-carbonyloxy-methoxy or 1-ethoxycarbonyl-ethylamino group, $R^b$ and $R^c$ independently of one another denote fluorine, chlorine, bromine, $C_{1-2}$-alkyl or trifluoromethyl, Z denotes CH, $R^d$ denotes hydrogen,
or, if $R^e$ denotes hydrogen, $R^d$ may also denote a group selected from among chlorine, bromine, cyano, $C_{1-2}$-alkyl, ethynyl, 2-phenyl-ethynyl, $C_{1-2}$-alkoxy, 5-methyl-[1,2,4]oxadiazolyl, benzoxazolyl, benzothiazolyl, phenylcarbonyl, pyrrolidinylcarbonyl and
aminocarbonyl, wherein a hydrogen atom may be replaced by a methyl or benzyl group and optionally another hydrogen atom may be replaced by a further methyl group, $R^e$ denotes hydrogen,
or, if $R^d$ denotes hydrogen, $R^d$ may also denote a group selected from among cyano, $C_{1-2}$-alkyl, $C_{1-2}$-alkoxy, dimethylaminosulphonyl, 5-methyl-[1,2,4]oxadiazolyl, pyrimidinyl,
amino, which is substituted by one or two methyl groups or a benzyl-carbonyl or phenylaminocarbonyl group, and
aminocarbonyl, wherein a hydrogen atom may be replaced by a methyl group and the other hydrogen atom may optionally be replaced by a phenyl-($C_{1-2}$-alkyl) group, which may be substituted in the phenyl moiety by a cyano group,
and $R^f$ denotes H,
the enantiomers, the mixtures and the salts thereof.

The following compounds may be mentioned by way of example:

(1)  {[(3,5-dichloro-phenylsulphonyl)-naphthalen-2-yl-amino]-methyl}-phosphonic acid, (2)  ({(3,5-dichloro-phenylsulphonyl)-[6-(5-methyl-[1,2,4]oxadiazol-3-yl)-naphthalen-2-yl]-amino}-methyl)-phosphonic acid, (3)  {[(5-benzylaminocarbonyl-naphthalen-2-yl)-(3,5-dichloro-phenylsulphonyl)-amino]-methyl}-phosphonic acid, (4)  {[(5-benzylaminocarbonyl-naphthalen-1-yl)-(3,5-dichloro-phenylsulphonyl)-amino]-methyl}-phosphonic acid, (5)  ({(3,5-dichloro-phenylsulphonyl)-[6-(phenylaminocarbonylamino)-naphthalen-2-yl]-amino}-methyl)-phosphonic acid, (6)  {[(6-benzylcarbonylamino-naphthalen-2-yl)-(3,5-dichloro-phenylsulphonyl)-amino]-methyl}-phosphonic acid, (7)  {[(3,5-dichloro-phenylsulphonyl)-naphthalen-1-yl-amino]-methyl}-phosphonic acid, (8)  {[[5-(N-benzyl-N-methyl-aminocarbonyl)-naphthalen-1-yl]-(3,5-dichloro-phenylsulphonyl)-amino]-methyl}-phosphonic acid, (9)  {[(3,5-dichloro-phenylsulphonyl)-(5-phenylethylaminocarbonyl-naphthalen-1-yl)-amino]-methyl}-phosphonic acid,

(10) {[(3,5-dichloro-phenylsulphonyl)-(5-methylaminocarbonyl-naphthalen-2-yl)-amino]-methyl}-phosphonic acid,

(11) ({(3,5-dichloro-phenylsulphonyl)-[5-(phenylaminocarbonylamino)-naphthalen-1-yl]-amino}-methyl)-phosphonic acid,

(12) {[(3,5-dichloro-phenylsulphonyl)-(6-pyrimidin-2-yl-naphthalen-2-yl)-amino]-methyl}-phosphonic acid,

(13) ({[5-(4-cyano-benzylaminocarbonyl)-naphthalen-2-yl]-(3,5-dichloro-phenylsulphonyl)-amino}-methyl)-phosphonic acid,

(14) {[(5-cyano-naphthalen-1-yl)-(3,5-dichloro-phenylsulphonyl)-amino]-methyl}-phosphonic acid,

(15) {[(3,5-dichloro-phenylsulphonyl)-[5-(5-methyl-[1,2,4]oxadiazol-3-yl)-naphthalen-1-yl]-amino}-methyl)-phosphonic acid,
(16) {[(3,5-dibromo-phenylsulphonyl)-naphthalen-1-yl-amino]-methyl}-phosphonic acid,
(17) {[(3,5-dichloro-phenylsulphonyl)-(5-dimethylaminosulphonyl-naphthalen-1-yl)-amino]-methyl}-phosphonic acid,
(18) {[(3,5-dichloro-phenylsulphonyl)-quinolin-8-yl-amino]-methyl}-phosphonic acid,
(19) ({3,5-dichloro-phenylsulphonyl)-[6-(5-methyl-[1,2,4]oxadiazol-3-yl)-naphthalen-1-yl]-amino}-methyl)-phosphonic acid,
(20) {[(3,5-dichloro-phenylsulphonyl)-quinolin-5-yl-amino]-methyl}-phosphonic acid,
(21) {[(3-chloro-5-methyl-phenylsulphonyl)-naphthalen-1-yl-amino]-methyl}-phosphonic acid,
(22) {[(3-bromo-5-chloro-phenylsulphonyl)-naphthalen-1-yl-amino]-methyl}-phosphonic acid,
(23) {[(3,5-dichloro-phenylsulphonyl)-(3-methyl-naphthalen-2-yl)-amino]-methyl}-phosphonic acid,
(24) {[(3,5-dichloro-phenylsulphonyl)-quinoxalin-6-yl-amino]-methyl}-phosphonic acid,
(25) {[(3,5-dichloro-phenylsulphonyl)-quinolin-3-yl-amino]-methyl}-phosphonic acid,
(26) {[(3,5-dichloro-phenylsulphonyl)-quinolin-6-yl-amino]-methyl}-phosphonic acid,
(27) {[(3,5-dichloro-phenylsulphonyl)-(2-cyano-naphthalen-1-yl)-amino]-methyl}-phosphonic acid,
(28) {[(3-bromo-5-methyl-phenylsulphonyl)-naphthalen-1-yl-amino]-methyl}-phosphonic acid,
(29) {[(3,5-dichloro-phenylsulphonyl)-(2-chloro-naphthalen-1-yl)-amino]-methyl}-phosphonic acid,
(30) {[(3,5-dichloro-phenylsulphonyl)-(5-methoxy-naphthalen-1-yl)-amino]-methyl}-phosphonic acid,
(31) {[(3,5-dichloro-phenylsulphonyl)-(4-methoxy-naphthalen-1-yl)-amino]-methyl}-phosphonic acid,
(32) {[(3,5-dichloro-phenylsulphonyl)-(2-bromo-naphthalen-1-yl)-amino]-methyl}-phosphonic acid,
(33) {[(3,5-dichloro-phenylsulphonyl)-(7-methyl-quinolin-8-yl)-amino]-methyl}-phosphonic acid,
(34) {[(3,5-dichloro-phenylsulphonyl)-(2-methyl-quinolin-8-yl)-amino]-methyl}-phosphonic acid,
(35) {[(3,5-dichloro-phenylsulphonyl)-(2-methoxy-naphthalen-1-yl)-amino]-methyl}-phosphonic acid,
(36) {[(3,5-dichloro-phenylsulphonyl)-(2-ethynyl-naphthalen-1-yl)-amino]-methyl}-phosphonic acid,
(37) {[(2-benzylaminocarbonyl-naphthalen-1-yl)-(3,5-dichloro-phenylsulphonyl)-amino]-methyl}-phosphonic acid,
(38) bis(2,2-dimethyl-propionyloxymethoxy){[(3,5-dichloro-phenylsulphonyl)-(5-methylaminocarbonyl-naphthalen-2-yl)-amino]-methyl}-phosphonate,
(39) mono-(2,2-dimethyl-propionyloxymethoxy){[(3,5-dichloro-phenylsulphonyl)-(5-methylaminocarbonyl-naphthalen-2-yl)-amino]-methyl}-phosphonate,
(40) bis(isopropyloxycarbonyloxymethyl){[(3,5-dichloro-phenylsulphonyl)-(5-methylaminocarbonyl-naphthalen-2-yl)-amino]-methyl}-phosphonate,
(41) bis(isopropyloxycarbonyloxymethyl){[(3-bromo-5-chloro-phenylsulphonyl)-naphthalen-1-yl-amino]-methyl}-phosphonate,
(42) bis(2,2-dimethyl-propionyloxymethoxy)-ester {[(3-bromo-5-chloro-phenylsulphonyl)-naphthalen-1-yl-amino]-methyl}-phosphonate,
(43) {[(3,5-dichloro-phenylsulphonyl)-(3-methyl-cinnolin-5-yl)-amino]-methyl}-phosphonic acid,
(44) {[(3,5-dichloro-phenylsulphonyl)-quinoxalin-5-yl-amino]-methyl}-phosphonic acid,
(45) {[(3,5-dichloro-phenylsulphonyl)-quinoline-7-yl-amino]-methyl}-phosphonic acid,
(46) {[(3,5-dichloro-phenylsulphonyl)-(3-methyl-quinolin-5-yl)-amino]-methyl}-phosphonic acid,
(47) {[(3,5-dichloro-phenylsulphonyl)-(4-dimethylamino-quinazolin-8-yl)-amino]-methyl}-phosphonic acid,
(48) bis(2,2-dimethyl-propionyloxymethoxy){[(3,5-dichloro-phenylsulphonyl)-quinolin-6-yl-amino]-methyl}-phosphonate,
(49) bis(isopropyloxycarbonyloxymethyl){[(3,5-dichloro-phenylsulphonyl)-quinolin-6-yl-amino]-methyl}-phosphonate and
(50) {[(3,5-dichloro-phenylsulphonyl)-quinazolin-8-yl-amino]-methyl}-phosphonic acid
and the salts thereof.

Terms and Definitions Used

Some terms used hereinbefore and hereinafter to describe the compounds according to the invention are defined more specifically below.

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Where a hyphen open on one side "-" is used in the structural formula of a substituent, this hyphen is to be understood as the linkage point to the remainder of the molecule. The substituent replaces the corresponding groups $R^a$, $R^b$, etc. If no hyphen open on one side is used in the structural formula of a substituent, the linkage point to the remainder of the molecule is clear from the name or the structural formula itself.

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds.

The subject-matter of this invention also includes the compounds according to the invention, including the salts thereof, wherein one or more hydrogen atoms, for example one, two, three, four or five hydrogen atoms, are replaced by deuterium.

The term "halogen" within the scope of the present invention denotes fluorine, chlorine, bromine or iodine. Unless stated otherwise, fluorine, chlorine and bromine are regarded as preferred halogens.

By the term "$C_{1-n}$-alkyl" (including those which are part of other groups) are meant branched and unbranched alkyl groups with 1 to n carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. Unless described otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-n}$-fluoroalkyl" (including those which are part of other groups) are meant partly fluorinated, branched and unbranched alkyl groups with 1 to n carbon atoms, in which at least one hydrogen atom is replaced by fluorine. Examples of such partly fluorinated alkyl groups include difluoromethyl, trifluoroethyl and tetrafluoroethyl.

By the term "$C_{1-n}$-perfluoroalkyl" (including those which are part of other groups) is meant a F—$(CF_2)_n$ group. Examples of such groups include trifluoromethyl, pentafluorethyl, heptafluoro-n-propyl, heptafluoro-iso-propyl etc., but preferably trifluoromethyl and pentafluorethyl.

By the term "$C_{2-n}$-alkenyl" (including those which are part of other groups) are meant branched and unbranched alkenyl groups, with 2 to n carbon atoms, which contain one or more double bonds. Examples include: ethenyl or vinyl, propenyl, butenyl, pentenyl, or hexenyl. Unless described otherwise, the definitions propenyl, butenyl, pentenyl and hexenyl include all the possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-n}$-alkynyl" (including those which are part of other groups) are meant branched and unbranched alkynyl groups, with 2 to n carbon atoms, which contain one or more triple bonds. Examples include: ethynyl, propynyl or butynyl. Unless described otherwise, the definitions propynyl and butynyl include all the possible isomeric forms of the groups in question. Thus, for example propynyl includes 1-propynyl and 2-propynyl, butynyl includes 1,2- and 3-butynyl, 1-methyl-1-propynyl, 1-methyl-2-propynyl etc.

By the term "$C_{3-n}$-cycloalkyl" (including those which are part of other groups) are meant saturated mono-, bi, tri or spirocyclic alkyl groups with 3 to n carbon atoms. Examples include: cyclopropyl, cyclobutyl, cyclopentyl, cyclohexyl, cycloheptyl, bicyclo[3.2.1.]octyl, spiro[4.5]decyl, norpinyl, norbornyl, norcaryl, adamantyl. Preferably the term $C_{3-7}$-cycloalkyl includes monocyclic alkyl groups. Unless otherwise stated, the cyclic alkyl groups may be substituted by one or more groups selected from among methyl, ethyl, hydroxy, methoxy, amino, methylamino, dimethylamino.

By the term "aryl" (including those which are part of other groups) are meant aromatic ring systems with 6, 10 or 14 carbon atoms. Examples include: phenyl, naphthyl, anthracenyl or phenanthrenyl. Unless otherwise stated, the aromatic groups may be substituted by one or more groups selected from among methyl, ethyl, difluoromethyl, trifluoromethyl, cyano, hydroxy, methoxy, difluoromethoxy, trifluoromethoxy, amino, fluorine, chlorine, bromine, iodine. Preferred aryl groups are naphthyl and phenyl, of which phenyl is particularly preferred.

By the term "heteroaryl" are meant 5-10-membered mono- or bicyclic aromatic heterocycles, wherein up to three carbon atoms may be replaced by one or more heteroatoms selected from among oxygen, nitrogen or sulphur. Each of the above-mentioned heterocycles may optionally also be anellated to a benzene ring.

The ring may be linked to the molecule through a carbon atom or, if present, through a nitrogen atom.

The following are examples of five- or six-membered heterocyclic aromatic groups:

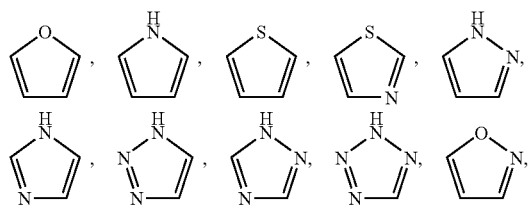

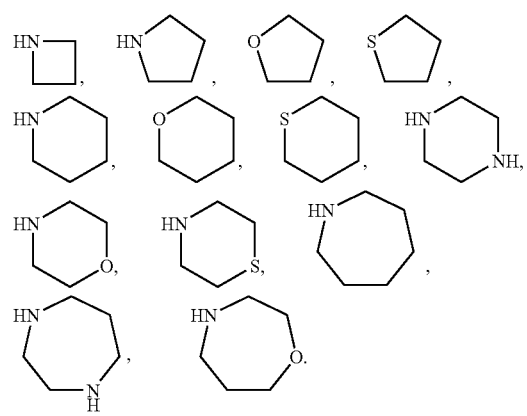

The following are mentioned as examples of 5-10-membered bicyclic heteroaryl rings: pyrrolizine, indole, indolizine, isoindole, indazole, purine, quinoline, isoquinoline, quinazoline, quinoxaline, cinnoline, phthalazine, naphthyridine, benzimidazole, benzofuran, benzothiophene, benzoxazole, benzothiazole, benzoisothiazole, pyridopyrimidine, pteridine, pyrimidopyrimidine.

Unless otherwise stated, the heteroaromatic groups may be substituted by one or more groups selected from among methyl, ethyl, difluoromethyl, trifluoromethyl, cyano, hydroxy, methoxy, difluoromethoxy, trifluoromethoxy, amino, fluorine, chlorine, bromine, iodine.

Preferred heteroaryl groups are furanyl, thiophenyl, pyrrole, 1H-imidazole, 1H-pyrazole, oxazole, isoxazole, thiazole, [1,2,4]oxadiazole, pyridinyl, pyrimidinyl, benzoxazolyl and benzothiazolyl.

Particularly preferred heteroaryl groups are [1,2,4]oxadiazol, pyrimidinyl, benzoxazolyl and benzothiazolyl.

By the term "heterocycloalkyl" are meant four- to seven-membered, preferably five- to six-membered, saturated heterocycles which may contain one, two or three heteroatoms, selected from among oxygen, sulphur and nitrogen, preferably oxygen and nitrogen. The ring may be linked to the molecule via a carbon atom or, if present, via a nitrogen atom.

The following are mentioned by way of example:

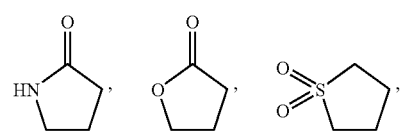

Unless otherwise mentioned, the heterocyclic group may be provided with one or more oxo groups. Examples include:

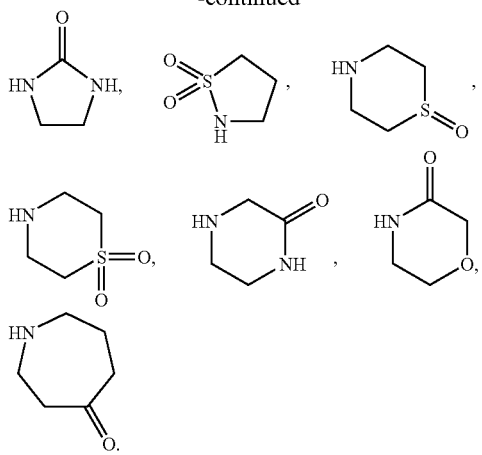

Unless otherwise mentioned, any nitrogen atoms contained in the ring may optionally be substituted by a methyl, ethyl, acetyl or methylsulphonyl group and the cyclic carbon atoms may be substituted by a methyl, ethyl, hydroxy, methoxy, amino, methylamino or dimethylamino group.

Preferred heterocycloalkyl groups are tetrahydrofuranyl, pyrrolidinyl, piperidinyl, morpholinyl, homomorpholinyl, piperazinyl, homopiperazinyl, 2-oxo-piperazinyl, 3-oxo-morpholinyl, 1,1-oxo-thiomorpholinyl and 1,1-dioxo-thiomorpholinyl. Particularly preferred heterocycloalkyl groups are tetrahydrofuranyl, pyrrolidinyl, piperidinyl, morpholinyl and piperazinyl.

By the term "group which may be converted in-vivo into a phosphonic acid group" is meant a group that can be cleaved under physiological conditions, with which a phosphonic acid group may be masked as a prodrug.

A number of groups that can be cleaved in vivo which may be used as phosphonic acid prodrugs are described in the literature (J. E. Starret et al. *Journal of Medicinal Chemistry* 1994, 37, 1857; H. T. Serafinowska et al. *Journal of Medicinal Chemistry* 1995, 38, 1372; J. P. Krise and V. J. Stella in *Advanced Drug Delivery Reviews* 1996, 19, 287; S. Freeman and K. C. Ross in *Progress in Medicinal Chemistry* 1997, 34, 111; P. Ettmayer et al. *Journal of Medicinal Chemistry* 2004, 47, 2393 and the reference literature cited therein). By a group which may be converted in-vivo into a phosphonic acid group is meant for example a mono- or diester PO(OH)(OR$^I$) or PO(OR$^I$)(OR$^{II}$), wherein R$^I$ and R$^{II}$ may be identical or different and denote for example acyloxyalkyl or alkyloxycarbonyloxyalkyl (G. J. Friis and H. Bundgaard, *European Journal of Pharmaceutical Sciences* 1996, 4, 49; R. Ortmann et al. *Archiv der Pharmazie—Chemistry in Life Sciences* 2005, 338, 305; P. Annaert et al. *Journal of Pharmaceutical Sciences* 2000, 89, 1054), aryl or benzyl (A. G. Mitchell et al. *Journal of the Chemical Society, Perkin Transactions I* 1992, 2345; S. De Lombaert et al. *Bioorganic & Medicinal Chemistry* 1995, 5, 151; S. De Lombaert et al. *Journal of Medicinal Chemistry* 1994, 37, 498), while the cleavability of the esters may be influenced by suitable substituents. Sulphur-containing phosphonic acid esters wherein R$^I$ and R$^{II}$ represent S-acylthioethyl, S-acylthiopropyl (SATE, SATP) or hydroxy-ethyl-disulphanylethyl ("dithiodiethyl" or DTE) are also described as phosphonic acid prodrugs (S. Benzaria et al. *Journal of Medicinal Chemistry* 1996, 39, 4958; V. Gagnard et al. *European Journal of Medicinal Chemistry* 2003, 38, 883, F. Puech et al. *Antiviral Research* 1993, 22, 155).

In addition cyclic phosphonic acid esters are also described, wherein OR$^I$ and OR$^{II}$ together denote an optionally substituted 1-aryl-propane-1,3-dioxy group, which are oxidatively cleaved by cytochrome P450 3A, preferably in the liver (M. D. Erion et al. *Journal of the American Chemical Society* 2004, 126, 5145; M. D. Erion et al. *Journal of Pharmacology and Experimental Therapeutics* 2005, 312, 554; U.S. Pat. No. 6,312,662).

Cyclic phosphonic acid esters, wherein OR$^I$ and OR$^{II}$ together denote a salicyl-alcohol group ("cycloSal"), are also proposed as prodrugs for phosphonic acid (C. Meier et al. *Journal of Medicinal Chemistry* 2005, 48, 8079).

Mono- or bis-phosphonamides PO(OR)(NR$^{III}$R$^{IV}$) or PO(NR$^{III}$R$^{IV}$)(NR$^V$R$^{VI}$), wherein R denotes H or aryl and the groups NR$^{III}$R$^{IV}$ and NR$^V$R$^{VI}$, which may be identical or different, denote an alkoxycarbonylalkylamino group, for example an alanine alkylester or glycinealkylester group, are also described as phosphonic acid prodrugs (C. Ballatore et al. *Bioorganic & Medicinal Chemistry Letters* 2001, 1, 1053). Cyclic variants of the phosphonamides and phosphonediamides are also possible.

Bis-POC-esters (wherein R' and R" are isopropyloxycarbonyloxymethyl) and bis-POM-esters (wherein R' and R" are pivaloyloxymethyl) are also mentioned as examples of particularly preferred phosphonic acid prodrugs PO(OR$^I$)(OR$^{II}$).

The term enantiomerically pure describes within the scope of the present invention compounds of formula (I), which are present in an enantiomerical purity of at least 85% ee, preferably at least 90% ee, particularly preferably >95% ee. The term ee (enantiomeric excess) is known in the art and describes the optical purity of chiral compounds.

The term "protective group" for the purposes of the present invention is to be understood as being a collective term for those organic groups with which certain functional groups of a molecule can be temporarily protected from attach by reagents, so that reactions can be carried out in a manner targeted on only the desired locations in the molecule. The protective groups should be capable of being introduced selectively under mild conditions and should be stable under the conditions of the planned reactions and cleaning operations, while racemisations and epimerisations should also be excluded. The protective groups should be cleavable under mild conditions selectively and ideally in a high yield. The choice of a suitable protective group, suitable conditions for its introduction (solvent, temperature, duration, etc.) as well as the possible ways of removing the protective group are known in the art (e.g. P. Kocienski, Protecting Groups, 3rd ed. 2004, THIEME, Stuttgart, ISBN: 3131370033).

By an "organic solvent" is meant, within the scope of the invention, an organic, low-molecular substance which can dissolve other organic substances by a physical method. To be suitable the prerequisite for the solvent is that neither the dissolving substance nor the dissolved substance should be chemically altered during the dissolving process, i.e. the components of the solution should be recoverable in their original form by physical separation processes such as distillation, crystallisation, sublimation, evaporation or adsorption. For various reasons, not only the pure solvents but also mixtures that combine the dissolving properties may be used. Examples include:

alcohols, preferably methanol, ethanol, propanol, butanol, octanol, cyclohexanol;
glycols, preferably ethyleneglycol, diethyleneglycol;
ethers/glycolethers, preferably diethyl ether, tert-butyl-methylether, dibutylether, anisol, dioxane, tetrahydrofuran, mono-, di-, tri-, polyethyleneglycol ethers;
ketones, preferably acetone, butanone, cyclohexanone;
esters, preferably acetic acid esters, glycolesters;
amides and other nitrogen compounds, preferably dimethylformamide, pyridine, N-methylpyrrolidone, acetonitrile;
sulphur compounds, preferably carbon disulphide, dimethylsulphoxide, sulpholane;
nitro compounds, preferably nitrobenzene;

halogenated hydrocarbons, preferably dichloromethane, chloroform, tetrachlormethane, tri- and tetrachloroethene, 1,2-dichloroethane, chlorofluorocarbons;

aliphatic or alicyclic hydrocarbons, preferably benzines, petroleum ether, cyclohexane, methylcyclohexane, decaline, terpene-L; or aromatic hydrocarbons, preferably benzene, toluene, o-xylene, m-xylene, p-xylene;

or corresponding mixtures thereof.

Compounds of general formula (I) may contain acid groups, such as e.g. carboxylic acid or phosphonic acid groups and/or basic groups such as e.g. amino functions. Compounds of general formula (I) may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali metal or alkaline earth metal hydroxides or carbonates, zinc or ammonium hydroxides or organic amines such as e.g. diethylamine, triethylamine, triethanolamine, inter alia. For preparing the alkali metal and alkaline earth metal salts of the compound of formula (I), it is preferable to use the alkali metal and alkaline earth metal hydroxides and hydrides, while the hydroxides and hydrides of the alkali metals, particularly sodium and potassium are preferred, and sodium and potassium hydroxide are particularly preferred. (See also *Pharmaceutical Salts*, S. M. Birge et al., *J. Pharm. Sci.* 1977, 66, 1-19)

Preparation Processes

The preparation of compounds of general formula (I) may be carried out according to the process shown in Scheme 1, wherein $R^a$ to $R^d$, A and Z are as hereinbefore defined, starting from a compound of general formula (III).

Scheme 1

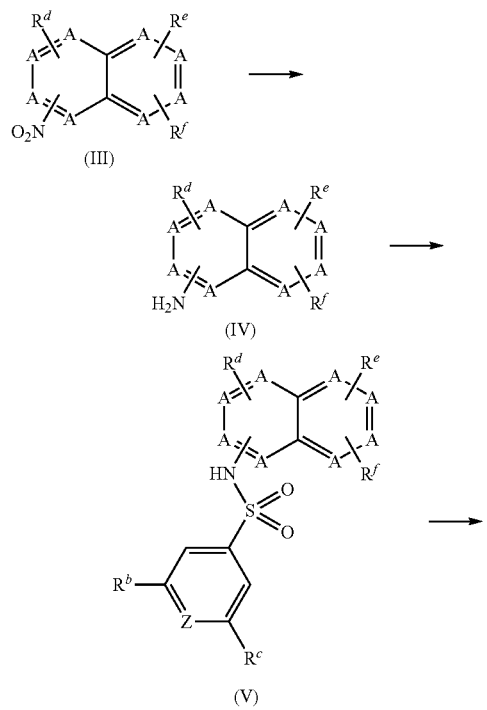

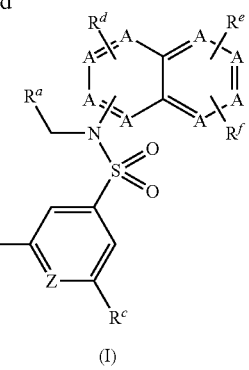

Here, compounds of general formula (IV) are obtained by reacting a compound of general formula (III) with a reducing agent.

A suitable reducing agent is for example hydrogen in the presence of a catalyst, such as palladium on charcoal, palladium hydroxide on charcoal or Raney nickel, while palladium on charcoal is particularly suitable. The hydrogenation is carried out in a suitable solvent such as methanol, ethanol, isopropanol, tetrahydrofuran, dichloromethane or ethyl acetate, but preferably methanol, ethanol or tetrahydrofuran, at a pressure between 0.5 and 7 bar, but preferably at a pressure between 0.5 and 3 bar, and at a temperature between 0° C. and 60° C., but preferably at a temperature between 15° C. and 40° C. Reactions of this kind are described by way of example in Example XXIII.

Also suitable for the reduction is tin dichloride hydrate in lower alcoholic solvents such as methanol or ethanol at a temperature between ambient temperature and 80° C.

Alternatively titanium trichloride may be used as reducing agent. Suitable solvents are mixtures of acetone and water. The reaction is carried out between 0° C. and 60° C., but preferably between 15° C. and 40° C. and in the presence of ammonium acetate.

Compounds of general formula (V) are obtained by sulphonylation of compounds of general formula (IV).

The sulphonylation is carried out with aromatic sulphonyl chlorides in the presence of a base, such as triethylamine, diisopropylethylamine, pyridine, or 4-dimethylamino-pyridine, but preferably pyridine. The reaction may be carried out in suitable solvents, such as diethyl ether, tetrahydrofuran, toluene, pyridine, dichloromethane, or chloroform, but preferably dichloromethane. The temperature may be between 0° C. and 60° C., but preferably between 15° C. and 40° C. Reactions of this kind are described by way of example in Example X.

Compounds of general formula (I) wherein $R^a$=PO(OH)$_2$ are obtained from compounds of general formula (V) by alkylation with a suitable methylphosphonic acid ester derivative and subsequent conversion into the free phosphonic acid.

Suitable alkylating agents are methylphosphonic acid ester derivatives that contain a leaving group such as chlorine, bromine, iodine, p-tolylsulphonate or methylsulphonate, but preferably trifluoromethylsulphonate. The alkylation is carried out in a solvent such as dimethylformamide, dimethylacetamide, tetrahydrofuran, acetonitrile, N-methylpyrrolidone or dimethylsulphoxide, but preferably in dimethylformamide, in the presence of a base such as sodium carbonate, potassium carbonate or caesium carbonate, but preferably potassium carbonate, and at a temperature between 0° C. and 100° C., but preferably between 15° C. and 50° C. Reactions of this kind are described by way of example in Example VIII.

If ethyl methylphosphonate derivatives are used as alkylating agents, the ethyl phosphonates PO(OEt)$_2$ obtained may be converted into the free phosphonic acids by cleaving the ethyl groups. The ethyl groups are preferably cleaved by treating with trimethylsilyl bromide or trimethylsilyl iodide in dichloromethane or 1,2-dichloroethane. Reactions of this kind are described by way of example in Example 2.

The free phosphonic acid of formula (I) thus obtained wherein R$^a$=PO(OH)$_2$ may optionally be converted by alkylation into a suitable phosphonic acid ester prodrug PO(OR')$_2$. The free phosphonic acid is reacted for example with C$_{1-6}$-alkyl-CO—O—C$_{1-3}$-alkyl-chlorides or C$_{1-6}$-alkoxy-CO—O—C$_{1-3}$-alkyl-chlorides. The reaction is carried out in the presence of silver carbonate and catalytic amounts of potassium iodide in a dipolar aprotic solvent such as dimethylformamide, N-methyl-pyrrolidine or acetonitrile, but preferably acetonitrile, optionally with the addition of small amounts of water at temperatures between 0° C. and 150° C., but preferably between ambient temperature and 90° C.

Reactions of this kind are described by way of example in Example 3.

The free phosphonic acid of formula (I) may alternatively also be converted into the phosphonic acid dichloride by reacting with a chlorinating agent such as thionyl chloride, for example. This may then be reacted with an amino acid ester derivative in the presence of an auxiliary base such as triethylamine or diisopropylethylamine in a suitable solvent to obtain the corresponding bis-phosphonamide. Examples of suitable amino acid ester derivatives include for example alanine alkyl esters or glycine alkyl esters.

Reactions of this kind are described by way of example in Example 4.

Alternatively compounds of general formula (I) may also be prepared according to the process shown in Scheme 2 according to the invention, starting from a compound of general formula (VI), wherein X denotes halogen or trifluoromethylsulphonate.

Scheme 2

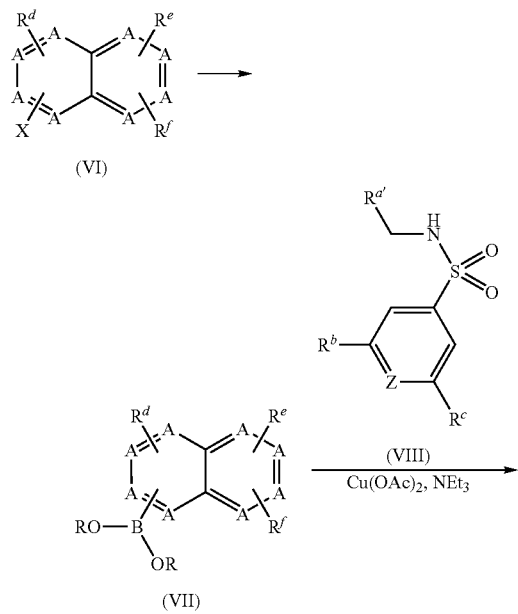

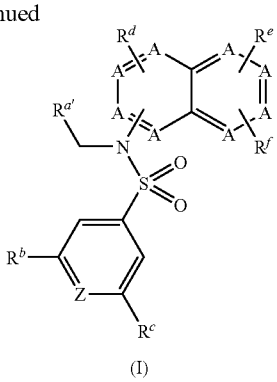

Compounds of general formula (VI) wherein X is halogen, preferably bromine or iodine, may be converted intermediately by metal-halogen exchange with a suitable reagent such as n-butyllithium, tert.-butyllithium or phenylmagnesium bromide, into the corresponding organometallic compounds, which are then reacted with trialkylborates (cf. also *Boronic Acids; Preparation and Applications in Organic Synthesis and Medicine*, D. G. Hall (ed)., WILEY-VCH 2005, p. 28 ff). Reactions of this kind are described by way of example in Example V. Alternatively compounds of formula (VI) wherein X is halogen or trifluoromethylsulphonate may be reacted with tetraalkoxydiboron compounds (RO)$_2$B—B(OR)$_2$ or dialkoxyboranes HB(OR)$_2$ in the presence of a suitable catalyst, for example PdCl$_2$(dppf), and a base to form the corresponding boron esters (VII) (cf. T. Ishiyama et al., *J. Org. Chem.* 1995, 60, 7508; M. Murata et al., *J. Org. Chem.* 1997; 62, 6458; N. Miyaura et al., *Tetrahedron Lett.* 1997, 38, 3447; M. Murata et al., *J. Org. Chem.* 2000; 65, 164).

The boric acid ester (VII) thus obtained may then be reacted after hydrolytic cleaving to form the free boric acid with sulphonamides of general formula (VIII), wherein R$^{a'}$ denotes a phosphonic acid group which is protected for example in the form of the ethyl or benzyl ester, to obtain the compounds of general formula (I). This reaction is conveniently carried out in the presence of copper(II)acetate and a tertiary amino base such as triethylamine or pyridine in a suitable solvent such as tetrahydrofuran or dichloromethane (D. M. T. Chan et al., *Tetrahedron Lett.* 1998, 39, 2933). Reactions of this kind are described by way of example in Example I.

If the phosphonic acid unit is introduced in the form of the benzyl ester, the cleaving to form the free phosphonic acid is preferably carried out hydrogenolytically, e.g. with hydrogen in the presence of a catalyst such as palladium on charcoal in a suitable solvent such as methanol, ethanol, ethyl acetate or glacial acetic acid, optionally with the addition of an acid such as hydrochloric acid, at temperatures between 0 and 100° C., but preferably at temperatures between 20 and 60° C., and under a hydrogen pressure of 1 to 7 bar, but preferably 1 to 3 bar. Reactions of this kind are described by way of example in Example 1.

The compounds of general formulae (III) to (VIII) used as starting materials are known from the literature in some cases or may be obtained by methods known from the literature (cf. Examples I to XXIV) or the processes described hereinbefore, optionally with the additional introduction of protective groups.

In the reactions described hereinbefore, any reactive groups present such as carboxy, hydroxy, amino or alkylamino groups may be protected during the reaction by conventional protecting groups which are cleaved again after the reaction.

For example, a protecting group for a carboxy group may be a methyl, ethyl, tert.butyl or benzyl group.

For example, a protecting group for a hydroxy group may be an acetyl, benzyl or tetrahydropyranyl group.

Protecting groups for an amino or alkylamino may be a formyl, acetyl, trifluoroacetyl, ethoxycarbonyl, tert.butoxycarbonyl, benzyloxycarbonyl, benzyl, methoxybenzyl or 2,4-dimethoxybenzyl group.

A carboxymethyl or carboxyethyl unit is cleaved for example by hydrolysis in an aqueous solvent, e.g. in water, methanol/water, isopropanol/water, acetic acid/water, tetrahydrofuran/water or dioxane/water, but preferably in methanol/water, in the presence of an acid such as trifluoroacetic acid, hydrochloric acid or sulphuric acid or in the presence of an alkali metal base such as lithium hydroxide, sodium hydroxide or potassium hydroxide, but preferably sodium hydroxide, or aprotically, e.g. In the presence of iodotrimethylsilane, at temperatures between 0 and 120° C., preferably at temperatures between 10 and 100° C.

A benzyl, methoxybenzyl or benzyloxycarbonyl group is advantageously cleaved by hydrogenolysis, e.g. with hydrogen in the presence of a catalyst such as palladium on charcoal in a suitable solvent such as methanol, ethanol, ethyl acetate or glacial acetic acid, optionally with the addition of an acid such as hydrochloric acid, at temperatures between 0 and 100° C., but preferably at temperatures between 20 and 60° C., and under a hydrogen pressure of 1 to 7 bar, but preferably 1 to 3 bar. However, a 2,4-dimethoxybenzyl group is preferably cleaved in trifluoroacetic acid in the presence of anisole.

A tert.-butyl or tert.-butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethyl ether.

Moreover, the compounds of general formula (I) obtained, or intermediate products from the synthesis of compounds of general formula (I), as already mentioned hereinbefore, may be resolved into their enantiomers and/or diastereomers. Thus, for example, cis/trans mixtures may be resolved into their cis and trans isomers, and compounds with at least one stereocentre may be resolved into their enantiomers.

Thus, for example, compounds of general formula (I) obtained, or intermediate products from the synthesis of compounds of general formula (I), which occur as racemates, may be separated by methods known per se (cf. Allinger N. L. and Eliel E. L. in "Topics in Stereochemistry", Vol. 6, Wiley Interscience, 1971) into their optical antipodes. Compounds of general formula (I), or intermediate products from the synthesis of compounds of general formula (I), with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by chromatography on chiral phases or by recrystallisation from an optically active solvent or by reacting with an optically active substance which forms salts or derivatives such as e.g. esters or amides with the racemic compound and separating the diastereomeric mixture of salts or derivatives thus obtained, e.g. on the basis of their differences in solubility, whilst the free antipodes may be released from the pure diastereomeric salts or derivatives by the action of suitable agents. The optically active substances that may be used include for example optically active acids and the activated derivatives or optically active alcohols thereof. Optically active acids in common use are e.g. the D- and L-forms of tartaric acid or dibenzoyltartaric acid, di-O-p-toluoyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula (I) obtained, or intermediate products from the synthesis of compounds of general formula (I), may be converted into the salts thereof, particularly, for pharmaceutical use, into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, the new compounds of general formula (I) obtained, or intermediate products from the synthesis of compounds of general formula (I), if they contain a carboxy group, may subsequently, if desired, be converted into the salts thereof with inorganic or organic bases, particularly, for pharmaceutical use, into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formula (I) are inhibitors of the interaction between human liver glycogen phosphorylase (HLGP) and protein PPP1R3 ($G_L$-subunit of glycogen-associated protein phosphatase 1 (PP1)). The effect of the compounds on the binding of the protein PPP1R3 and the glycogen phosphorylase activated by phosphorylation is determined in a binding test based on SPA technology (Amersham Pharmacia). The binding of the substances inhibits the interaction of the glycogen phosphorylase with the protein PPP1R3B. All measurements were made in triplicate in the 384-well format (Optiplate, Perkin Elmer).

Human glycogen phosphorylase is recombinantly expressed in *E. Coli* and purified. The isolated non-phosphorylated HLGP is radioactively labelled in a marking reaction with phosphorylase kinase (200-500 U/mg, P2014, Sigma) and $^{33}$P-gamma ATP (110 TBq/mmol, Hartmann Analytic) (Ref.: Cohen et al., Methods Enzymol. 1988, Vol 159 pp 390). In a binding test, in a volume of 100 µl (test buffer: 50 mM Tris/HCl pH 7.0, 0.1 mM EGTA, 0.1% mercapto-ethanol), different amounts of a test substance (final concentration: 1 nM to 30 µM) are incubated at ambient temperature for 16 hours with 100000 cpm of labelled HLGP, 375 µg streptavidin-SPA Beads (RPNQ 0007, Amersham Pharmacia), 0.1 µg GL-peptide (Biotin-FPEWPSYLGYEKLGPYY). After centrifuging for 5 minutes at 500 g the plate is measured (Topcount, Packard). The cpm values measured are used to calculate the $IC_{50}$ values specified. The basal value is determined in the absence of the peptide and the maximum value is determined in the absence of the test substance.

The compounds of general formula (I) described in the Examples have $IC_{50}$ values in the range from 30 nM to 10 µM.

Ranges of Indications

In view of their ability to suppress the interaction of glycogen phosphorylase a with the GL-subunit of glycogen-associated protein phosphatase 1 (PP1), the compounds of general formula (I) according to the invention and the corresponding pharmaceutically acceptable salts thereof are theoretically suitable for treating and/or preventatively treating all those conditions or diseases that can be influenced by inhibiting the interaction of glycogen phosphorylase a with the GL-subunit of glycogen-associated protein phosphatase 1 (PP1). Therefore the compounds according to the invention are particularly suitable for the prevention or treatment of diseases, particularly metabolic disorders, or conditions such as type 1 and type 2 diabetes mellitus, complications of diabetes (such as e.g. retinopathy, nephropathy or neuropathies, diabetic foot, ulcers, macroangiopathies), metabolic acidosis or ketosis, reactive hypoglycaemia, hyperinsulinaemia, glucose metabolic disorder, insulin resistance, metabolic syndrome, dyslipidaemias of different origins, atherosclerosis and related diseases, obesity, high blood pressure, chronic heart failure, oedema and hyperuricaemia. These substances are also suitable for preventing beta-cell degeneration such as e.g. apoptosis or necrosis of pancreatic beta cells. The substances are also suitable for improving or restoring the functionality of pancreatic cells, and also for increasing the number and size of pancreatic beta cells. The compounds according to the invention may also be used as diuretics or antihypertensives and are suitable for the prevention and treatment of acute renal failure.

In particular, the compounds according to the invention, including the physiologically acceptable salts thereof, are suitable for the prevention or treatment of diabetes, particularly type 1 and type 2 diabetes mellitus, and/or diabetic complications.

The dosage required to achieve the corresponding activity for treatment or prevention usually depends on the compound which is to be administered, the patient, the nature and gravity of the illness or condition and the method and frequency of administration and is for the patient's doctor to decide.

Expediently, the dosage may be from 0.1 to 1000 mg, preferably 0.5 to 500 mg, by intravenous route, and 1 to 1000 mg, preferably 10 to 500 mg, by oral route, in each case administered 1 to 4 times a day. For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The compounds according to the invention may also be used in conjunction with other active substances, particularly for the treatment and/or prevention of the diseases and conditions mentioned above. Other active substances which are suitable for such combinations include in particular those which potentiate the therapeutic effect of an inhibitor of the interaction of glycogen phosphorylase a with the $G_L$ subunit of glycogen-associated protein phosphatase 1 (PP1) according to the invention with respect to one of the indications mentioned and/or which allow the dosage of an inhibitor of the interaction of glycogen phosphorylase a with the GL subunit of glycogen-associated protein phosphatase 1 (PP1) according to the invention to be reduced. Suitable therapeutic agents belonging to such a combination include, for example, antidiabetic agents such as metformin, sulphonylureas (e.g. glibenclamide, tolbutamide, glimepiride), nateglinide, repaglinide, thiazolidine-diones (e.g. rosiglitazone, pioglitazone), PPAR-gamma-agonists (e.g. GI 262570) and antagonists, PPAR-gamma/alpha modulators (e.g. KRP 297), alpha-glucosidase inhibitors (e.g. miglitol, acarbose, voglibose), DPPIV inhibitors (e.g. sitagliptine, vildagliptine), SGLT2-inhibitors, alpha2-antagonists, insulin and insulin analogues, GLP-1 and GLP-1 analogues (e.g. Exendin-4) or amylin. Other active substances suitable as combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, lipid lowering agents such as for example HMG-CoA-reductase inhibitors (e.g. simvastatin, atorvastatin), fibrates (e.g. bezafibrate, fenofibrate), nicotinic acid and the derivatives thereof, PPAR-alpha agonists, PPAR-delta agonists, ACAT inhibitors (e.g. avasimibe) or cholesterol absorption inhibitors such as, for example, ezetimibe, bile acid-binding substances such as, for example, cholestyramine, inhibitors of ileac bile acid transport, HDL-raising compounds such as CETP inhibitors or ABC1 regulators or active substances for treating obesity, such as sibutramine or tetrahydrolipostatin, dexfenfluramine, axokine, antagonists of the cannabinoid1 receptor, MCH-1 receptor antagonists, MC4 receptor agonists, NPY5 or NPY2 antagonists or β3-agonists such as SB-418790 or AD-9677 and agonists of the 5HT2c receptor.

Moreover, combinations with drugs for influencing high blood pressure, chronic heart failure or atherosclerosis such as e.g. A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Examples of angiotensin II receptor antagonists are candesartan cilexetil, potassium losartan, eprosartan mesylate, valsartan, telmisartan, irbesartan, EXP-3174, L-158809, EXP-3312, olmesartan, medoxomil, tasosartan, KT-3-671, GA-0113, RU-64276, EMD-90423, BR-9701, etc. Angiotensin II receptor antagonists are preferably used for the treatment or prevention of high blood pressure and complications of diabetes, often combined with a diuretic such as hydrochlorothiazide.

A combination with uric acid synthesis inhibitors or uricosurics is suitable for the treatment or prevention of gout.

A combination with GABA-receptor antagonists, Na-channel blockers, topiramat, protein-kinase C inhibitors, advanced glycation end product inhibitors or aldose reductase inhibitors may be used for the treatment or prevention of complications of diabetes.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt of such a compound combined with at least one of the active substances described above as a combination partner, for preparing a pharmaceutical composition which is suitable for the treatment or prevention of diseases or conditions which can be affected by inhibiting the interaction of glycogen phosphorylase a with the $G_L$ subunit of glycogen-associated protein phosphatase 1 (PP1). These are preferably metabolic diseases, particularly one of the diseases or conditions listed above, most particularly diabetes or diabetic complications.

The use of the compound according to the invention, or a physiologically acceptable salt thereof, in combination with another active substance may take place simultaneously or at staggered times, but particularly within a short space of time.

If they are administered simultaneously, the two active substances are given to the patient together; if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

Thus, for example, a pharmaceutical composition according to the invention comprises a combination of a compound of formula (I) according to the invention or a physiologically acceptable salt of such a compound and at least one angiotensin II receptor antagonist optionally together with one or more inert carriers and/or diluents.

The compound according to the invention, or one of the physiologically acceptable salts thereof, and the additional active substance to be combined therewith may both be present together in one formulation, for example a tablet or capsule, or separately in two identical or different formulations, for example as a so-called kit-of-parts.

The Examples that follow are intended to illustrate the present invention without restricting it:

PREPARATION OF THE STARTING COMPOUNDS

Example I

Dibenzyl {[(3,5-dichloro-phenylsulphonyl)-naphthalen-2-yl-amino]-methyl}-phosphonate

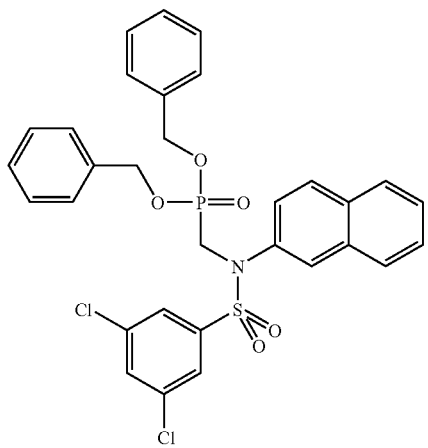

89 mg 2-naphthaleneboronic acid are added to a mixture of 130 mg dibenzyl [(3,5-dichloro-phenylsulphonylamino)-methyl]-phosphonate and 100 mg molecular sieve (4 Å) in 8 ml of tetrahydrofuran. Then 47 mg copper-II-acetate and 72 μl triethylamine are added and the reaction mixture is stirred for 24 hours at ambient temperature. For working up the reaction mixture is filtered. The filter cake is washed with tetrahydrofuran and the filtrate is evaporated down in vacuo. The flask residue is divided between concentrated aqueous ammonia solution and methylene chloride. The aqueous phase is extracted with methylene chloride and the combined organic phases are washed with 1 N sodium hydroxide solution, dried on magnesium sulphate and evaporated down. The crude product is purified by chromatography through a silica gel column.

Yield: 72 mg (44% of theory)

Mass spectrum (ESI$^+$): m/z=626 [M+H]$^+$

The following compounds are obtained analogously to Example I:

(1) diethyl ({(3,5-dichloro-phenylsulphonyl)-[6-(5-methyl-[1,2,4]oxadiazol-3-yl)-naphthalen-2-yl]amino}-methyl)-phosphonate

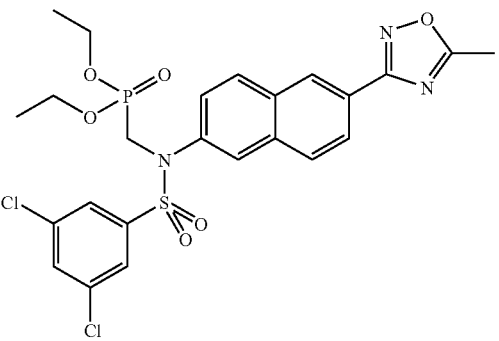

Mass spectrum (ESI$^+$): m/z=584, 586, 588 [M+H]$^+$ (2) diethyl {[(6-tert.-butoxycarbonylamino-naphthalen-2-yl)-(3,5-dichloro-phenylsulphonyl)-amino]-methyl}-phosphonate

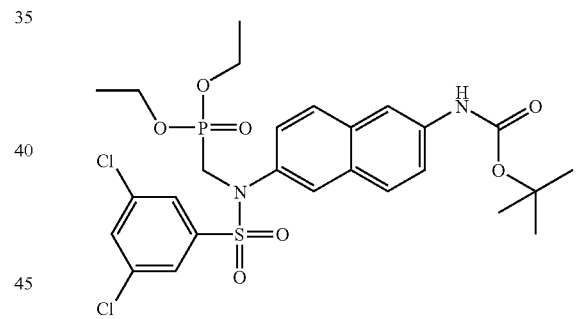

$R_f$ value: 0.48 (silica gel, methylene chloride/methanol=95:5)

(3) 3,5-dichloro-N-[6-(5-methyl-[1,2,4]oxadiazol-3-yl)-naphthalen-1-yl]-phenylsulphonamide

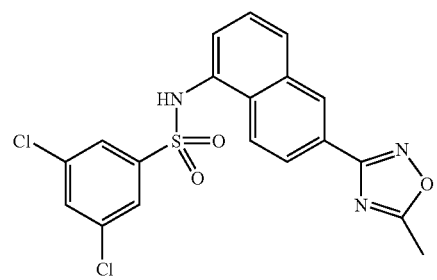

(The reaction is carried out in methylene chloride.)

Example II

Dibenzyl [(3,5-dichloro-phenylsulphonylamino)-methyl]-phosphonate

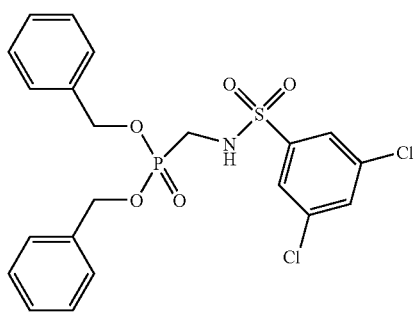

A mixture of 2.00 g dibenzyl [(trityl-amino)-methyl]-phosphonate in 10 ml of tetrahydrofuran is combined with 1.87 ml 4 N hydrochloric acid in dioxane and stirred for three hours at ambient temperature. Then the solvent is distilled off in vacuo using the rotary evaporator. The flask residue is stirred with ethyl acetate, suction filtered and taken up in 20 ml of tetrahydrofuran. Then 9.37 ml 1 N sodium hydroxide solution are added and while cooling with an ice bath a solution of 1.10 g of 3,5-dichloro-phenylsulphonyl chloride in 10 ml of tetrahydrofuran is added dropwise. The reaction mixture is stirred for another two hours at 0° C., then heated to ambient temperature and evaporated down in vacuo. The flask residue is divided between dilute hydrochloric acid and ethyl acetate. The aqueous phase is extracted with ethyl acetate and the combined organic phases are washed with saturated sodium chloride solution, dried on magnesium sulphate and evaporated down. The crude product is purified by chromatography through a silica gel column.

Yield: 130 mg (7% of theory)
Mass spectrum (ESI⁻): m/z=498, 500, 502 [M−H]⁻

Example III

Dibenzyl [(trityl-amino)-methyl]-phosphonate

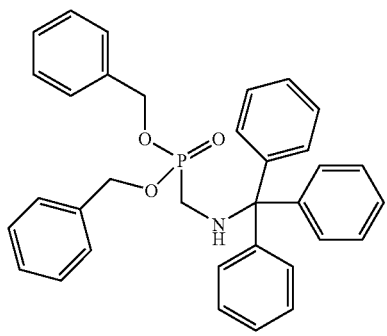

A mixture of 1.00 g tritylamin in 20 ml of toluene is combined with 127 mg paraformaldehyde and 50 μl acetic acid and stirred for one hour at 80° C. Then 0.85 ml dibenzylphosphite are added and the reaction mixture is refluxed for three hours. Then 200 μl triethylamine are added and the reaction mixture is evaporated down in vacuo using the rotary evaporator. The flask residue is chromatographed through a silica gel column.

Yield: 2.00 g (97% of theory)
Mass spectrum (ESI⁺): m/z=534 [M+H]⁺

Example IV

Diethyl [(3,5-dichloro-phenylsulphonylamino)-methyl]-phosphonate

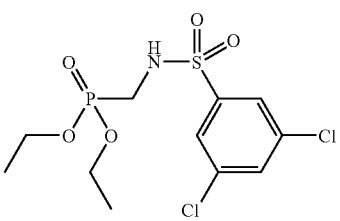

58.33 ml 1 N sodium hydroxide solution are added to 5.00 g diethyl(aminomethyl)phosphonate-monooxalate in 80 ml of tetrahydrofuran while cooling with an ice bath. Then a solution of 5.73 g of 3,5-dichloro-phenylsulphonyl chloride in 100 ml of tetrahydrofuran is added dropwise within one hour. The reaction mixture is stirred for another two hours at 0° C., then heated to ambient temperature and adjusted to pH 4 with dilute hydrochloric acid. The solvent is distilled off in vacuo using the rotary evaporator and the flask residue is extracted with ethyl acetate. The combined organic extracts are dried on magnesium sulphate and evaporated down. The crude product is purified by chromatography through a silica gel column.

Yield: 3.10 g (42% of theory)
Mass spectrum (ESI⁺): m/z=376, 378, 380 [M+H]⁺

Example V

[6-(5-methyl-[1,2,4]oxadiazol-3-yl)-naphthalen-2-yl]-boronic acid

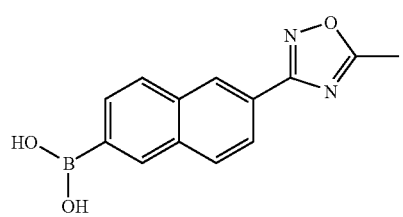

4.76 ml n-butyllithium solution (1.6 M in hexane) are added dropwise to 1.00 g 3-(6-bromo-naphthalen-2-yl)-5-methyl-[1,2,4]oxadiazole in 15 ml of tetrahydrofuran at −78° C. The reaction mixture is stirred for another hour at −78° C., then 1.94 ml trimethylborate are added dropwise. Then the reaction mixture is left to heat up to ambient temperature and stirred overnight at this temperature. Then 9 ml 1 N hydrochloric acid are added while cooling with an ice bath. After 10 minutes at ambient temperature the tetrahydrofuran is distilled off in vacuo using the rotary evaporator and the flask residue is extracted with ethyl acetate. The combined organic extracts are dried on magnesium sulphate and evaporated down. The crude product is stirred with diisopropylether, suction filtered and dried.

Yield: 510 mg (58% of theory)
Mass spectrum (ESI⁻): m/z=253 [M−H]⁻

The following compounds are obtained analogously to Example V:

(1) [6-(tert.-butoxycarbonylamino)-naphthalen-2-yl]-boronic acid

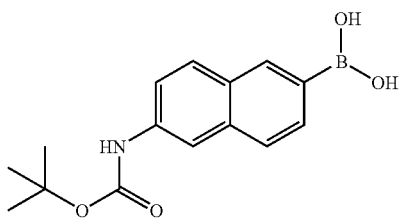

(prepared using triisopropylborate.)
Mass spectrum (ESI⁻): m/z=286 [M−H]⁻

(2) 6-(5-methyl-[1,2,4]oxadiazol-3-yl)naphthalene-1-boronic acid

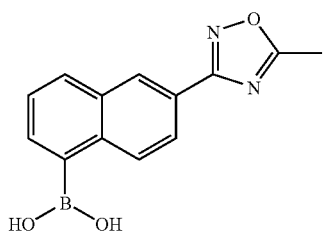

(prepared using tert.-butyllithium)

Example VI 3-(6-bromo-naphthalen-2-yl)-5-methyl-[1,2,4]oxadiazole

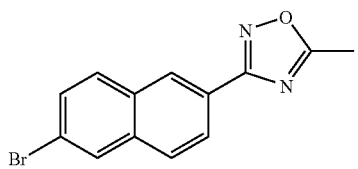

6.11 ml acetic anhydride are added to 4.40 g 6-bromo-N-hydroxy-naphthalene-2-carboxamidine in 30 ml 2,4,6-trimethylpyridine. The reaction mixture is stirred for one hour at ambient temperature and then heated to 130° C. for four hours. After the reaction has ended the mixture is evaporated down in vacuo and the flask residue is stirred with ethyl acetate and petroleum ether, suction filtered and dried.

Yield: 3.80 g (79% of theory)
Mass spectrum (EI): m/z=288, 290 [M]⁺

The following compounds are obtained analogously to Example VI:

(1) diethyl {[(3,5-dichloro-phenylsulphonyl)-[5-(5-methyl-[1,2,4]oxadiazol-3-yl)-naphthalen-1-yl]-amino}-methyl)-phosphonate

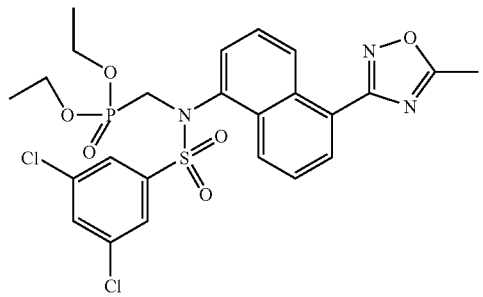

$R_f$ value: 0.52 (silica gel, ethyl acetate)
Mass spectrum (ESI⁺): m/z=584, 586, 588 [M+H]⁺

(2) 3-(5-bromo-naphthalen-2-yl)-5-methyl-[1,2,4] oxadiazole

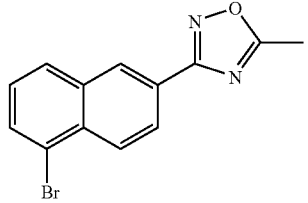

$R_f$ value: 0.75 (silica gel, cyclohexane/ethyl acetate=1:1)
Mass spectrum (ESI⁺): m/z=289, 291 [M+H]⁺

(3) diethyl ({(3,5-dichloro-phenylsulphonyl)-[2-(5-methyl-[1,2,4]oxadiazol-3-yl)-naphthalen-1-yl]-amino}-methyl)-phosphonate

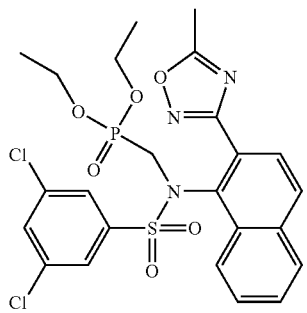

$R_f$ value: 0.50 (silica gel, petroleum ether/ethyl acetate=1:2)
Mass spectrum (ESI⁺): m/z=584, 586, 588 [M+H]⁺

Example VII

6-bromo-N-hydroxy-naphthalene-2-carboxamidine

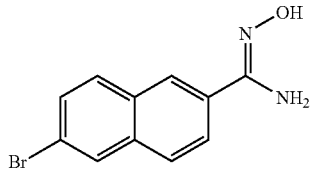

2.48 g hydroxylamine-hydrochloride and 5.68 ml triethylamine are added to 4.10 g of 6-bromo-2-cyano-naphthalene in 100 ml of ethanol and the reaction mixture is refluxed for four hours. After cooling to ambient temperature the solvent is distilled off in vacuo using the rotary evaporator and the flask residue is divided between water and ethyl acetate. The aqueous phase is extracted with ethyl acetate and the combined organic phases are dried on magnesium sulphate and evaporated down.

Yield: 4.40 g (94% of theory)

Mass spectrum (ESI$^+$): m/z=265, 267 [M+H]$^+$

The following compounds are obtained analogously to Example VII:

(1) diethyl ({(3,5-dichloro-phenylsulphonyl)-[5-(N-hydroxycarbamimidoyl)-naphthalen-1-yl]-amino}-methyl)-phosphonate

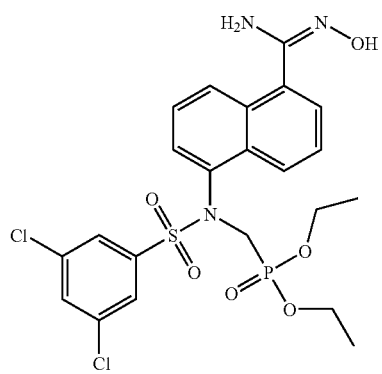

$R_f$ value: 0.25 (silica gel, methylene chloride/methanol=95:5)

Mass spectrum (ESI$^+$): m/z=560, 562, 564 [M+H]$^+$

(2) 5-bromo-N-hydroxy-naphthalene-2-carboxamidine

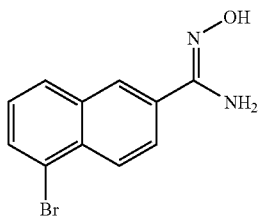

$R_f$ value: 0.54 (silica gel, cyclohexane/ethyl acetate=1:1)

Mass spectrum (ESI$^+$): m/z=265, 267 [M+H]$^+$

(3) diethyl ({(3,5-dichloro-phenylsulphonyl)-[2-(N-hydroxycarbamimidoyl)-naphthalen-1-yl]-amino}-methyl)-phosphonate

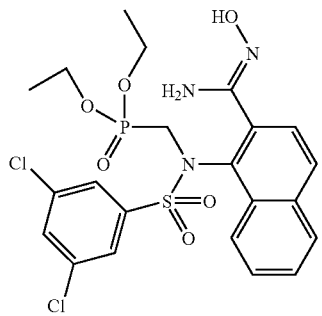

$R_f$ value: 0.30 (silica gel, petroleum ether/ethyl acetate=1:2)

(4) diethyl {[(2-aminocarbonyl-naphthalen-1-yl)-(3,5-dichloro-phenylsulphonyl)-amino]-methyl}-phosphonate

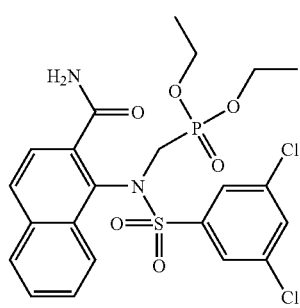

$R_f$ value: 0.16 (silica gel, petroleum ether/ethyl acetate=1:2)

Mass spectrum (ESI$^+$): m/z=545, 547, 549 [M+H]$^+$

Example VIII

Diethyl {[(5-benzylaminocarbonyl-naphthalen-2-yl)-(3,5-dichloro-phenylsulphonyl)-amino]-methyl}-phosphonate

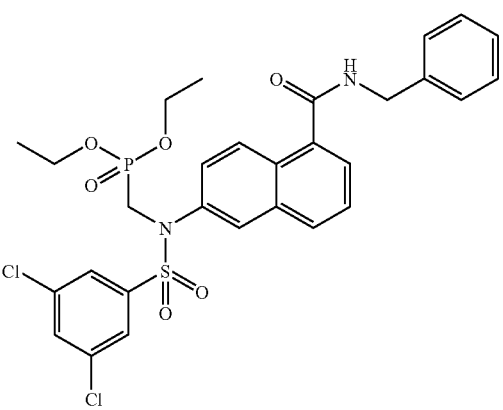

A mixture of 200 mg 6-(3,5-dichloro-phenylsulphonylamino)-naphthalene-1-carboxylic acid-benzylamide, 180 mg diethylphosphonomethyltriflate (prepared analogously to *Tetrahedron Letters* 1986, 27, 1477) and 100 mg potassium carbonate in 4 ml N,N-dimethylformamide is stirred for three hours at ambient temperature. Then it is combined with ethyl acetate, washed with water and saturated sodium chloride solution, dried on magnesium sulphate and evaporated down. The flask residue is chromatographed through a silica gel column with cyclohexane/ethyl acetate (40:60 to 0:100) as eluant.

Yield: 200 mg (76% of theory)

$R_f$ value: 0.20 (silica gel, petroleum ether/ethyl acetate=1:2)

Mass spectrum (ESI$^+$): m/z=635, 637, 639 [M+H]$^+$

The following compounds are obtained analogously to Example VIII:

(1) diethyl {[(5-benzylaminocarbonyl-naphthalen-1-yl)-(3,5-dichloro-phenylsulphonyl)-amino]-methyl}-phosphonate

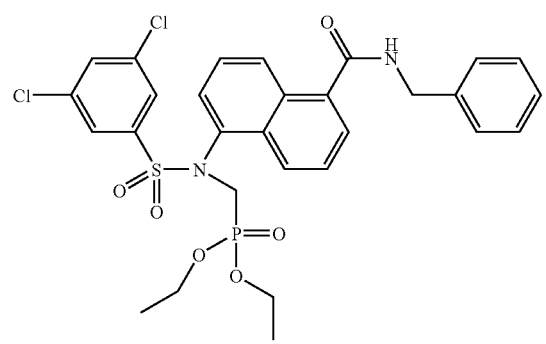

$R_f$ value: 0.55 (silica gel, ethyl acetate)
Mass spectrum (ESI$^+$): m/z=652, 654, 656 [M+NH$_4$]$^+$ (2) diethyl {[(3,5-dichloro-phenylsulphonyl)-naphthalen-1-yl-amino]-methyl}-phosphonate

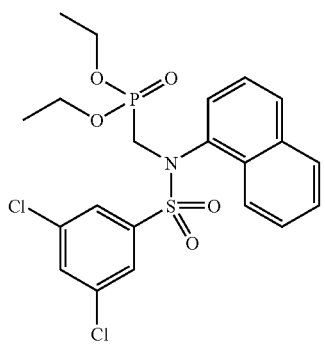

$R_f$ value: 0.28 (silica gel, petroleum ether/ethyl acetate=1:1)
Mass spectrum (ESI$^+$): m/z=502, 504, 506 [M+H]$^+$ (3) diethyl {[[5-(N-benzyl-N-methyl-aminocarbonyl)-naphthalen-1-yl]-(3,5-dichloro-phenylsulphonyl)-amino]-methyl}-phosphonate

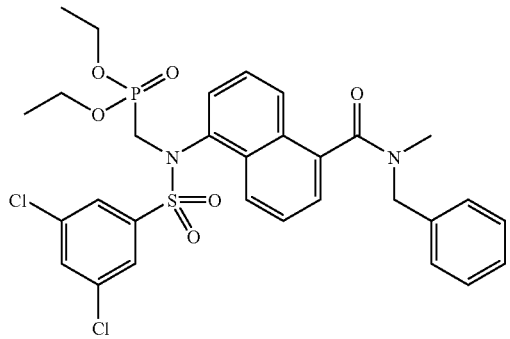

Mass spectrum (ESI$^+$): m/z=649, 651, 653 [M+H]$^+$ (4) diethyl {[(3,5-dichloro-phenylsulphonyl)-(5-phenylethylaminocarbonyl-naphthalen-1-yl)-amino]-methyl}-phosphonate

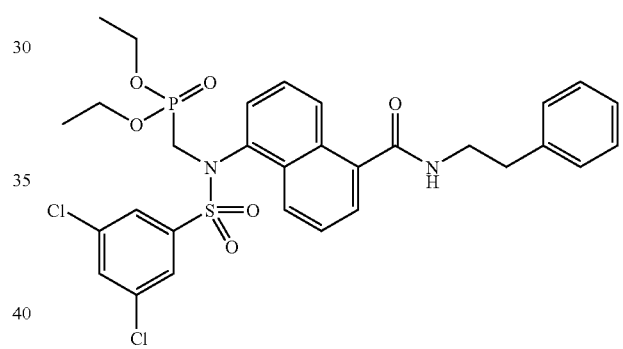

Mass spectrum (ESI$^+$): m/z=649, 651, 653 [M+H]$^+$ (5) diethyl {[(3,5-dichloro-phenylsulphonyl)-(5-methylaminocarbonyl-naphthalen-2-yl)-amino]-methyl}-phosphonate

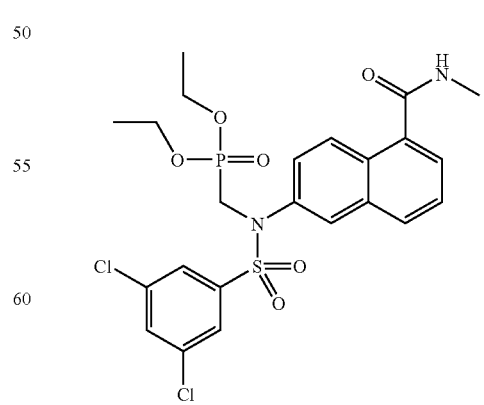

$R_f$ value: 0.20 (silica gel, ethyl acetate)
Mass spectrum (ESI$^+$): m/z=659, 661, 663 [M+H]$^+$ (6) diethyl ({(3,5-dichloro-phenylsulphonyl)-[5-(phenylaminocarbonylamino)-naphthalen-1-yl]-amino}-methyl)-phosphonate

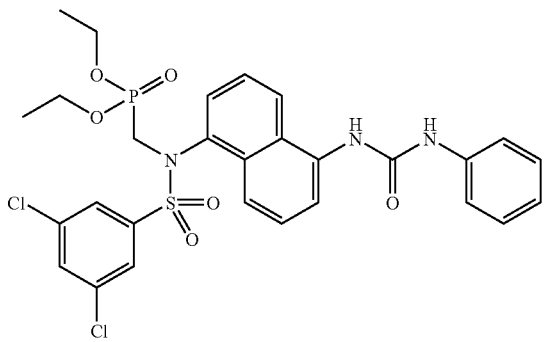

R$_f$ value: 0.50 (silica gel, ethyl acetate)
Mass spectrum (ESI$^+$): m/z=636, 638, 640 [M+H]$^+$ (7) diethyl {[(3,5-dichloro-phenylsulphonyl)-(6-pyrimidin-2-yl-naphthalen-2-yl)-amino]-methyl}-phosphonate

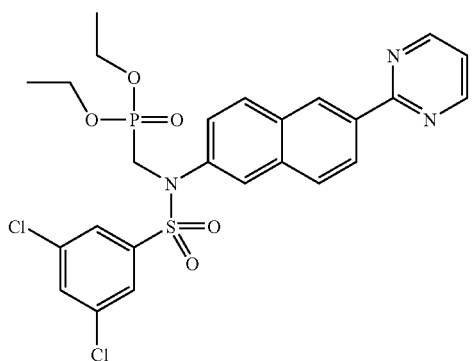

R$_f$ value: 0.20 (silica gel, petroleum ether/ethyl acetate=1:2)
Mass spectrum (ESI$^+$): m/z=580, 582, 584 [M+H]$^+$ (8) diethyl ({[5-(4-cyano-benzylaminocarbonyl)-naphthalen-2-yl]-(3,5-dichloro-phenylsulphonyl)-amino}-methyl)-phosphonate

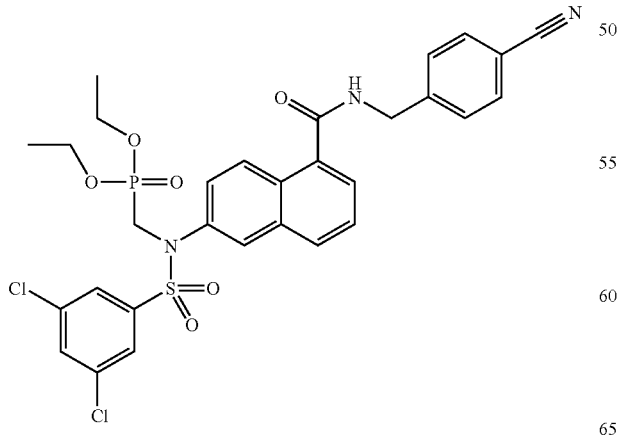

R$_f$ value: 0.40 (silica gel, ethyl acetate)
Mass spectrum (ESI$^+$): m/z=660, 662, 664 [M+H]$^+$ (9) diethyl {[(5-cyano-naphthalen-1-yl)-(3,5-dichloro-phenylsulphonyl)-amino]-methyl}-phosphonate

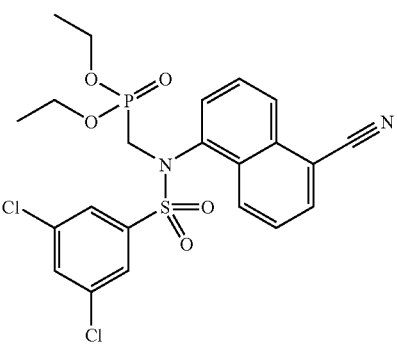

R$_f$ value: 0.40 (silica gel, petroleum ether/ethyl acetate=1:2)
Mass spectrum (ESI$^+$): m/z=527, 529, 531 [M+H]$^+$

(10) diethyl {[(3,5-dichloro-phenylsulphonyl)-(2-methyl-naphthalen-1-yl)-amino]-methyl}-phosphonate

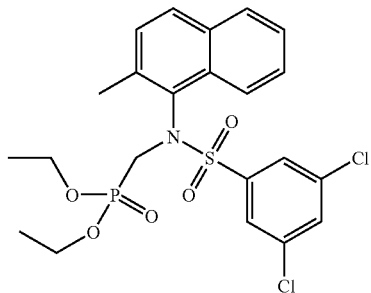

R$_f$ value: 0.30 (silica gel, cyclohexane/ethyl acetate=1:1)
Mass spectrum (ESI$^+$): m/z=516, 518, 520 [M+H]$^+$

(11) diethyl {[(3,5-dimethyl-phenylsulphonyl)-(5-methylaminocarbonyl-naphthalen-2-yl)-amino]-methyl}-phosphonate

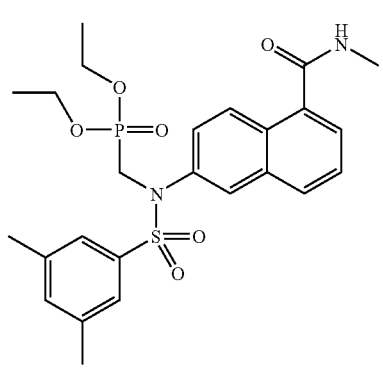

R$_f$ value: 0.10 (silica gel, ethyl acetate)
Mass spectrum (ESI$^+$): m/z=519 [M+H]$^+$

(12) diethyl {[(3,5-dibromo-phenylsulphonyl)-naphthalen-1-yl-amino]-methyl}-phosphonate

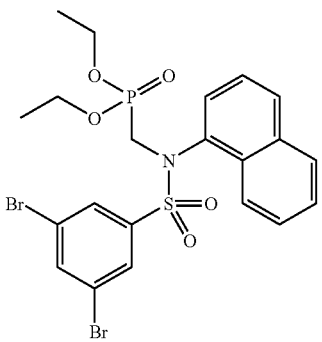

$R_f$ value: 0.52 (silica gel, petroleum ether/ethyl acetate=1:2)
Mass spectrum (ESI⁺): m/z=590, 592, 594 [M+H]⁺

(13) diethyl {[(3,5-dichloro-phenylsulphonyl)-(5-dimethylaminosulphonyl-naphthalen-1-yl)-amino]-methyl}-phosphonate

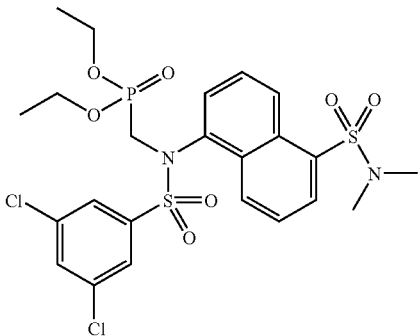

$R_f$ value: 0.30 (silica gel, petroleum ether/ethyl acetate=1:2)
Mass spectrum (ESI⁺): m/z=609, 611, 613 [M+H]⁺

(14) diethyl {[(3,5-dichloro-phenylsulphonyl)-quinolin-8-yl-amino]-methyl}-phosphonate

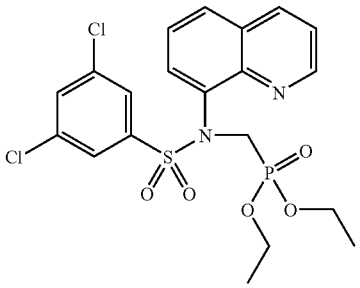

$R_f$ value: 0.54 (silica gel, ethyl acetate)
Mass spectrum (ESI⁺): m/z=503, 505, 507 [M+H]⁺

(15) diethyl ({(3,5-dichloro-phenylsulphonyl)-[6-(5-methyl-[1,2,4]oxadiazol-3-yl)-naphthalen-1-yl]-amino}-methyl)-phosphonate

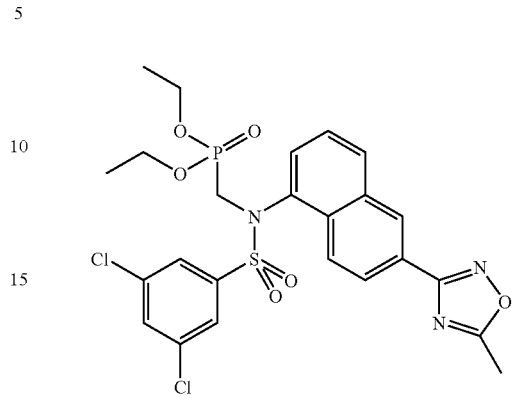

(16) diethyl {[(3,5-dichloro-phenylsulphonyl)-quinolin-5-yl-amino]-methyl}-phosphonate

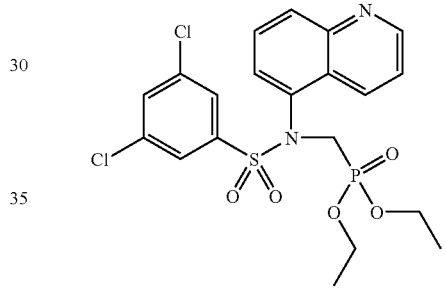

$R_f$ value: 0.32 (silica gel, ethyl acetate)
Mass spectrum (ESI⁺): m/z=503, 505, 507 [M+H]⁺

(17) diethyl {[(3-chloro-5-methyl-phenylsulphonyl)-naphthalen-1-yl-amino]-methyl}-phosphonate

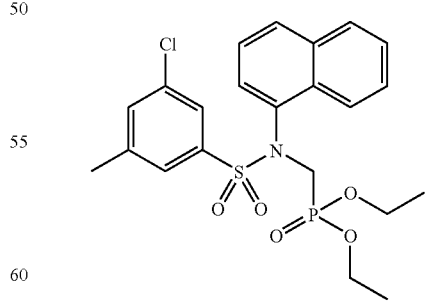

$R_f$ value: 0.43 (silica gel, petroleum ether/ethyl acetate=1:2)
Mass spectrum (ESI⁺): m/z=482, 484 [M+H]⁺

(18) diethyl {[(3,5-dimethyl-phenylsulphonyl)-naphthalen-1-yl-amino]-methyl}-phosphonate

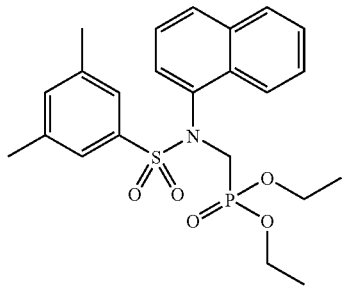

R_f value: 0.35 (silica gel, petroleum ether/ethyl acetate=1:2)
Mass spectrum (ESI+): m/z=462 [M+H]+

(19) diethyl {[(3-bromo-5-chloro-phenylsulphonyl)-naphthalen-1-yl-amino]-methyl}-phosphonate

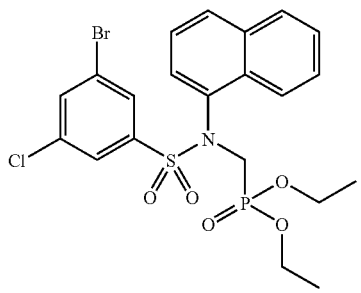

Mass spectrum (ESI+): m/z=546, 548, 540 [M+H]+

(20) diethyl {[(3-chloro-5-fluoro-phenylsulphonyl)-naphthalen-1-yl-amino]-methyl}-phosphonate

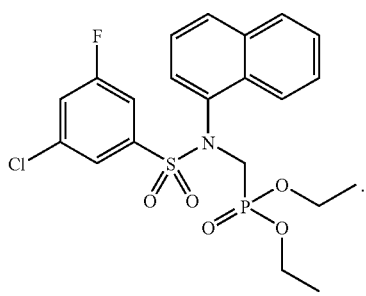

R_f value: 0.30 (silica gel, petroleum ether/ethyl acetate=1:1)
Mass spectrum (ESI+): m/z=486, 488 [M+H]+

(21) diethyl {[(3,5-dichloro-phenylsulphonyl)-(3-methyl-naphthalen-2-yl)-amino]-methyl}-phosphonate

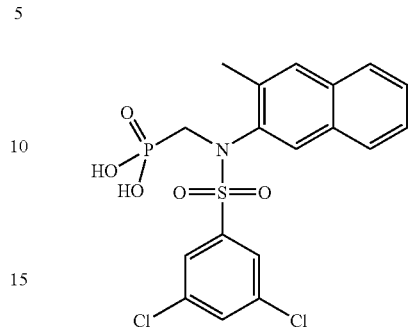

R_f value: 0.40 (silica gel, cyclohexane/ethyl acetate=1:1)
Mass spectrum (ESI+): m/z=516, 518, 520 [M+H]+

(22) diethyl {[(3,5-dichloro-phenylsulphonyl)-quinoxalin-6-yl-amino]-methyl}-phosphonate

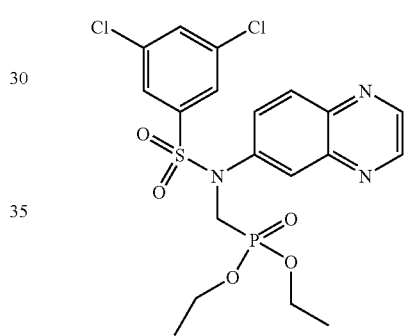

R_f value: 0.67 (silica gel, ethyl acetate/methanol=9:1)
Mass spectrum (ESI+): m/z=504, 506, 508 [M+H]+

(23) diethyl {[(3,5-dichloro-phenylsulphonyl)-quinolin-3-yl-amino]-methyl}-phosphonate

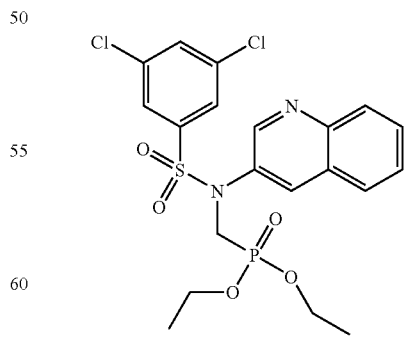

R_f value: 0.58 (silica gel, ethyl acetate)
Mass spectrum (ESI+): m/z=503, 505, 507 [M+H]+

(24) diethyl {[(3,5-dichloro-phenylsulphonyl)-quinolin-6-yl-amino]-methyl}-phosphonate

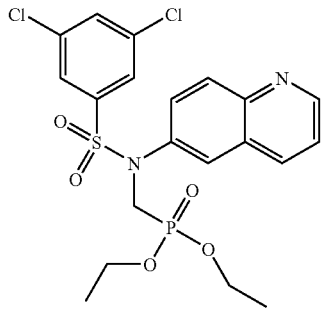

R_f value: 0.61 (silica gel, ethyl acetate/methanol=9:1)

(25) diethyl {[(3,5-dichloro-phenylsulphonyl)-(2-cyano-naphthalen-1-yl)-amino]-methyl}-phosphonate

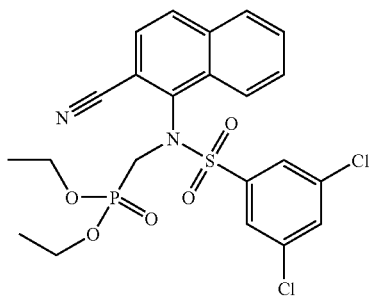

R_f value: 0.22 (silica gel, petroleum ether/ethyl acetate=1:1)
Mass spectrum (ESI+): m/z=527, 529, 531 [M+H]+

(26) diethyl {[(3-bromo-5-methyl-phenylsulphonyl)-naphthalen-1-yl-amino]-methyl}-phosphonate

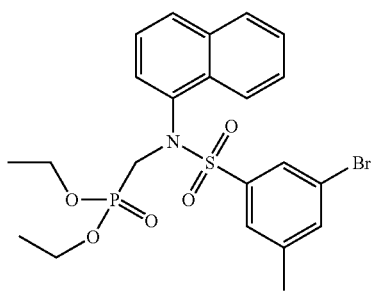

R_f value: 0.22 (silica gel, petroleum ether/ethyl acetate=1:1)
Mass spectrum (ESI+): m/z=526, 528 [M+H]+

(27) diethyl {[(3,5-dichloro-phenylsulphonyl)-(2-chloro-naphthalen-1-yl)-amino]-methyl}-phosphonate

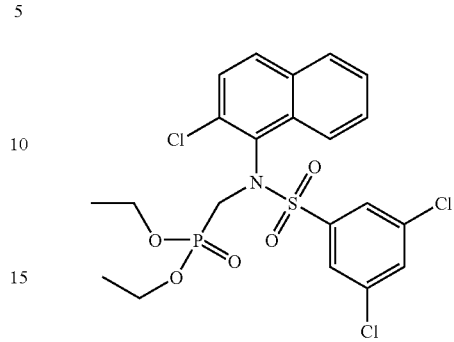

R_f value: 0.33 (silica gel, petroleum ether/ethyl acetate=1:1)
Mass spectrum (ESI+): m/z=536, 538, 540, 542 [M+H]+

(28) diethyl {[(3,5-dichloro-phenylsulphonyl)-(5-methoxy-naphthalen-1-yl)-amino]-methyl}-phosphonate

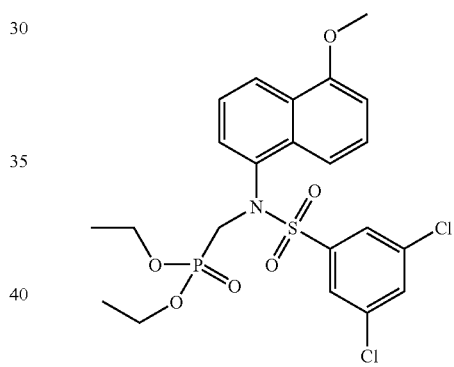

R_f value: 0.30 (silica gel, cyclohexane/ethyl acetate=1:1)
Mass spectrum (ESI+): m/z=532, 534, 536 [M+H]+

(29) diethyl {[(3-chloro-5-trifluoromethyl-phenylsulphonyl)-naphthalen-1-yl-amino]-methyl}-phosphonate

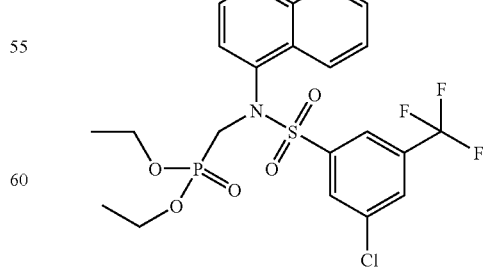

R_f value: 0.30 (silica gel, petroleum ether/ethyl acetate=1:1)
Mass spectrum (ESI+): m/z=536, 538 [M+H]+

(30) diethyl {[(3,5-dichloro-phenylsulphonyl)-(4-methoxy-naphthalen-1-yl)-amino]-methyl}-phosphonate

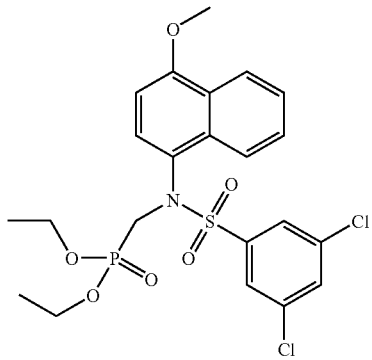

R$_f$ value: 0.78 (silica gel, ethyl acetate)
Mass spectrum (ESI$^+$): m/z=532, 534, 536 [M+H]$^+$

(31) diethyl {[(3,5-dichloro-phenylsulphonyl)-(2-bromo-naphthalen-1-yl)-amino]-methyl}-phosphonate

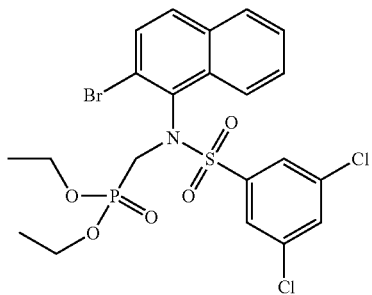

R$_f$ value: 0.40 (silica gel, petroleum ether/ethyl acetate=5:1)
Mass spectrum (ESI$^+$): m/z=580, 582, 584, 586 [M+H]$^+$

(32) diethyl {[(3,5-dichloro-phenylsulphonyl)-(7-methyl-quinolin-8-yl)-amino]-methyl}-phosphonate

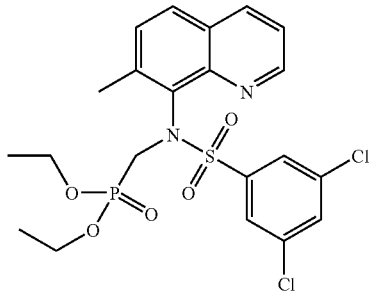

R$_f$ value: 0.78 (silica gel, ethyl acetate)
Mass spectrum (ESI$^+$): m/z=517, 519, 521 [M+H]$^+$

(33) diethyl {[(3,5-dichloro-phenylsulphonyl)-(2-methyl-quinolin-8-yl)-amino]-methyl}-phosphonate

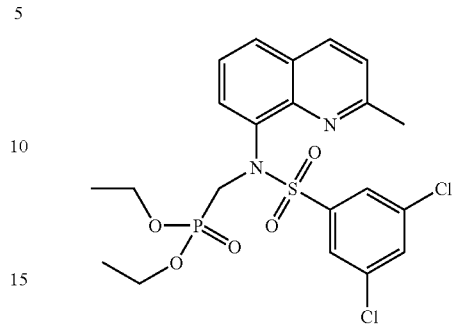

R$_f$ value: 0.75 (silica gel, ethyl acetate)
Mass spectrum (ESI$^+$): m/z=517, 519, 521 [M+H]$^+$

(34) diethyl {[(3,5-dichloro-phenylsulphonyl)-(2-methoxy-naphthalen-1-yl)-amino]-methyl}-phosphonate

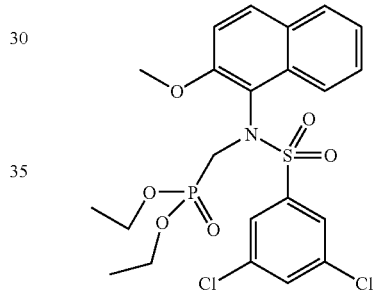

Mass spectrum (ESI$^+$): m/z=532, 534, 536 [M+H]$^+$

(35) diethyl {[(3,5-dichloro-phenylsulphonyl)-(2-trimethylsilanylethynyl-naphthalen-1-yl)-amino]-methyl}-phosphonate

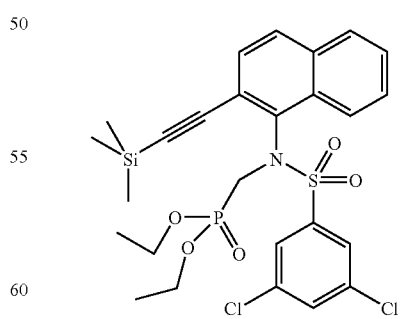

R$_f$ value: 0.50 (silica gel, petroleum ether/ethyl acetate=1:1)
Mass spectrum (ESI$^+$): m/z=598, 600, 602 [M+H]$^+$

(36) diethyl {[(3,5-dichloro-phenylsulphonyl)-(2-phenylethynyl-naphthalen-1-yl)-amino]-methyl}-phosphonate

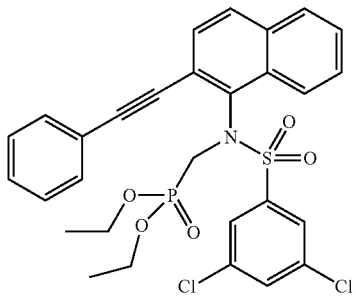

R$_f$ value: 0.64 (silica gel, petroleum ether/ethyl acetate=1:2)

Mass spectrum (ESI$^+$): m/z=602, 604, 606 [M+H]$^+$

(37) diethyl {[(3-chloro-5-cyano-phenylsulphonyl)-naphthalen-1-yl-amino]-methyl}-phosphonate

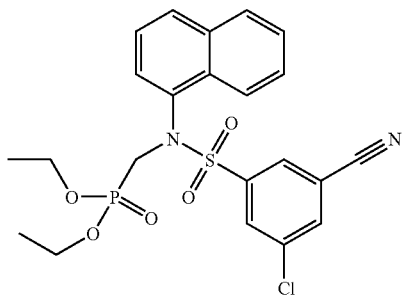

R$_f$ value: 0.20 (silica gel, petroleum ether/ethyl acetate=1:1)

Mass spectrum (ESI$^+$): m/z=493, 495 [M+H]$^+$

(38) diethyl {[(2-benzothiazol-2-yl-naphthalen-1-yl)-(3,5-dichloro-phenylsulphonyl)-amino]-methyl}-phosphonate

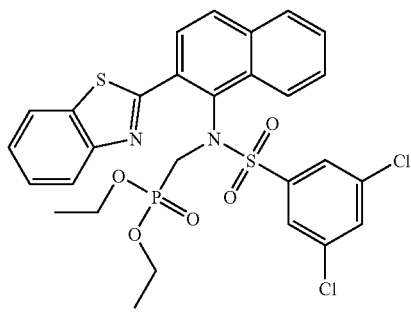

R$_f$ value: 0.35 (silica gel, cyclohexane/ethyl acetate=1:1)

(39) diethyl {[(3,5-dichloro-4-fluoro-phenylsulphonyl)-naphthalen-1-yl-amino]-methyl}-phosphonate

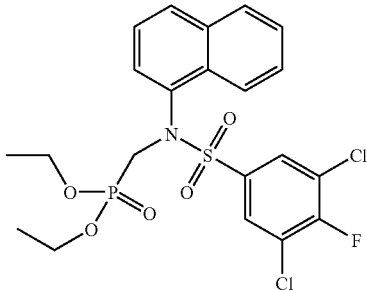

R$_f$ value: 0.28 (silica gel, petroleum ether/ethyl acetate=1:1)

Mass spectrum (ESI$^+$): m/z=520, 522, 524 [M+H]$^+$

(40) diethyl {[(2-benzylaminocarbonyl-naphthalen-1-yl)-(3,5-dichloro-phenylsulphonyl)-amino]-methyl}-phosphonate

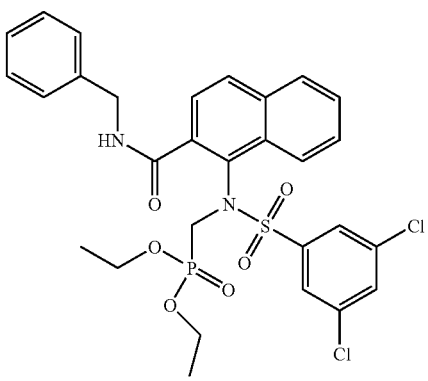

R$_f$ value: 0.25 (silica gel, cyclohexane/ethyl acetate=1:1)

(41) diethyl {[(2-pyrrolidin-1-ylcarbonyl-naphthalen-1-yl)-(3,5-dichloro-phenylsulphonyl)-amino]-methyl}-phosphonate

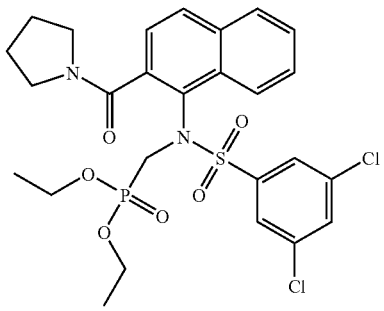

R$_f$ value: 0.10 (silica gel, cyclohexane/ethyl acetate=1:1)
Mass spectrum (ESI$^+$): m/z=599, 601, 603 [M+H]$^+$

(42) diethyl {[(2-benzoxazol-2-yl-naphthalen-1-yl)-(3,5-dichloro-phenylsulphonyl)-amino]-methyl}-phosphonate

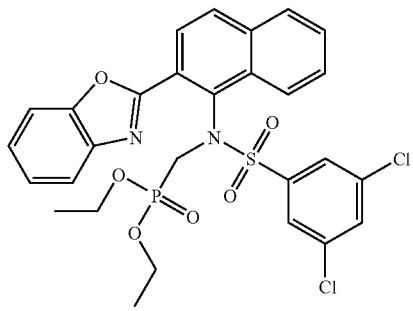

$R_f$ value: 0.40 (silica gel, methylene chloride/methanol=98:2)

Mass spectrum (ESI$^+$): m/z=619, 621, 623 [M+H]$^+$

(43) diethyl {[(2-dimethylaminocarbonyl-naphthalen-1-yl)-(3,5-dichloro-phenylsulphonyl)-amino]-methyl}-phosphonate

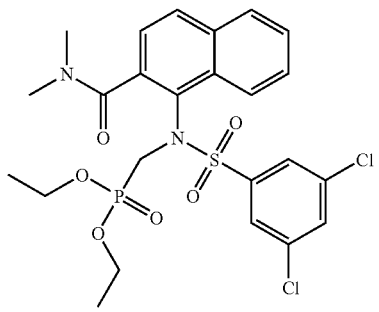

$R_f$ value: 0.45 (silica gel, methylene chloride/methanol=95:5)

Mass spectrum (ESI$^+$): m/z=573, 575, 577 [M+H]$^+$

(44) diethyl {[(2-phenylcarbonyl-naphthalen-1-yl)-(3,5-dichloro-phenylsulphonyl)-amino]-methyl}-phosphonate

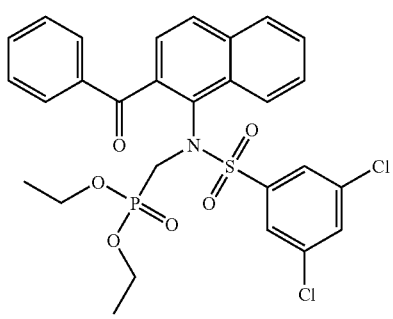

$R_f$ value: 0.35 (silica gel, methylene chloride/methanol=98:2)

Mass spectrum (ESI$^+$): m/z=606, 608, 610 [M+H]$^+$

(45) diethyl {[(3-chloro-5-nitro-phenylsulphonyl)-naphthalen-1-yl-amino]-methyl}-phosphonate

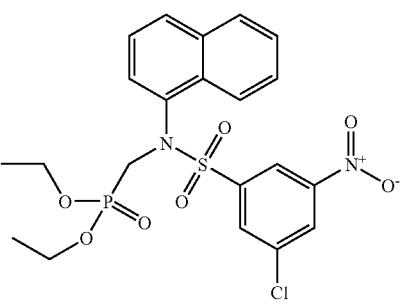

$R_f$ value: 0.20 (silica gel, cyclohexane/ethyl acetate=1:1)

Mass spectrum (ESI$^+$): m/z=513, 515 [M+H]$^+$

(46) diethyl {[(3,5-dichloro-phenylsulphonyl)-(3-methyl-cinnolin-5-yl)-amino]-methyl}-phosphonate

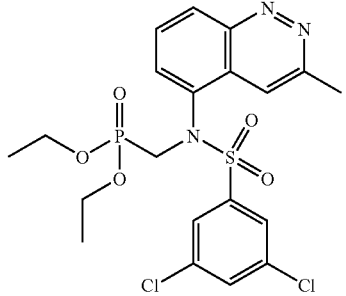

$R_f$ value: 0.18 (silica gel, ethyl acetate/methanol=98:2)

(47) diethyl {[(3,5-dichloro-phenylsulphonyl)-(3-methyl-isoquinolin-5-yl)-amino]-methyl}-phosphonate

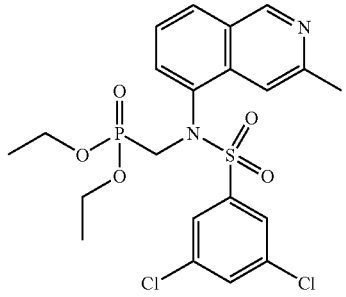

$R_f$ value: 0.35 (silica gel, methylene chloride/methanol=9:1)

Mass spectrum (ESI$^+$): m/z=517, 519, 521 [M+H]$^+$

(48) diethyl {[(3,5-dichloro-phenylsulphonyl)-qui-noxalin-5-yl-amino]-methyl}-phosphonate

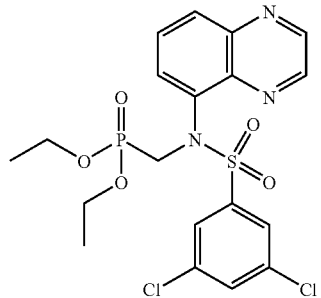

R$_f$ value: 0.75 (silica gel, methylene chloride/methanol=9:1)

Mass spectrum (ESI$^+$): m/z=504, 506, 508 [M+H]$^+$

(49) diethyl {[(3,5-dichloro-phenylsulphonyl)-quino-line-7-yl-amino]-methyl}-phosphonate

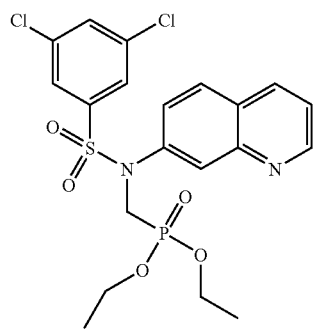

R$_f$ value: 0.30 (silica gel, ethyl acetate/methanol=98:2)
Mass spectrum (ESI$^+$): m/z=503, 505, 507 [M+H]$^+$

(50) diethyl {[(3,5-dichloro-phenylsulphonyl)-(3-methyl-quinolin-5-yl)-amino]-methyl}-phosphonate

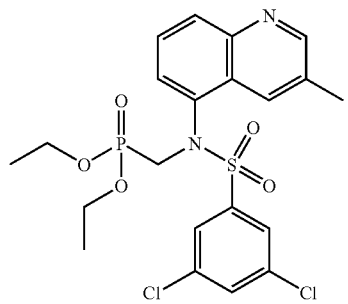

R$_f$ value: 0.50 (silica gel, ethyl acetate/methanol=98:2)
Mass spectrum (ESI$^+$): m/z=517, 519, 521 [M+H]$^+$

(51) diethyl {[(3,5-dichloro-phenylsulphonyl)-(4-dimethylamino-quinazolin-8-yl)-amino]-methyl}-phosphonate

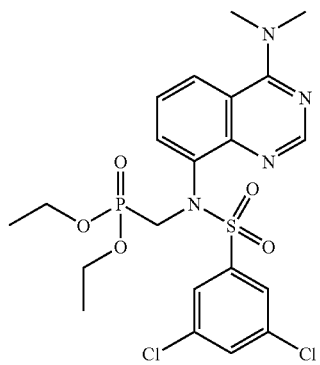

R$_f$ value: 0.73 (silica gel, methylene chloride/methanol=9:1)

(52) diethyl {[(3,5-dichloro-phenylsulphonyl)-quinazolin-8-yl-amino]-methyl}-phosphonate

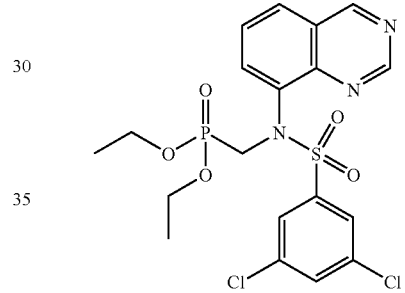

R$_f$ value: 0.47 (silica gel, methylene chloride/methanol=95:5)
Mass spectrum (ESI$^+$): m/z=504, 506, 508 [M+H]$^+$ Example IX 6-(3,5-dichloro-phenylsulphonylamino)-naphthalene-1-carboxylic acid-benzylamide

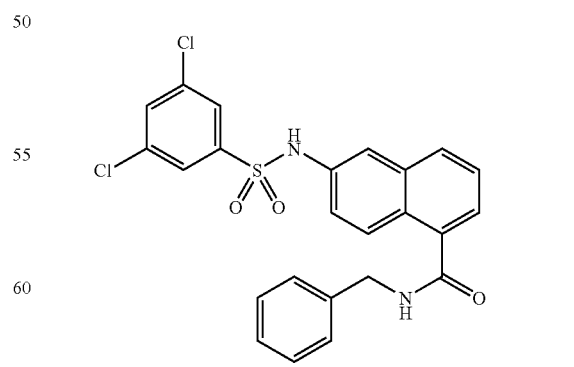

1.50 ml diisopropylethylamine and 2.81 g O-(benzotriazol-1-yl)-1,1,3,3-tetramethyluronium-tetrafluoroborate are added to 3.47 g 6-(3,5-dichloro-phenylsulphonylamino)- naphthalene-1-carboxylic acid in 15 ml N,N-dimethylformamide. The reaction mixture is stirred for 15 minutes at ambient temperature, then 0.97 ml benzylamine and 1.50 ml diisopropylethylamine are added and the mixture is stirred for a further two hours at ambient temperature. For working up the reaction mixture is mixed with water and extracted with ethyl acetate. The combined organic extracts are washed with 1N hydrochloric acid, 1N sodium hydroxide solution and saturated sodium chloride solution, dried on magnesium sulphate and evaporated down. The foam-like flask residue is stirred overnight with cyclohexane/ethyl acetate and the resulting crystalline precipitate is suction filtered, washed with cyclohexane and dried.

Yield: 3.75 g (88% of theory)

$R_f$ value: 0.64 (silica gel, petroleum ether/ethyl acetate=1:1)

Mass spectrum (ESI$^+$): m/z=485, 487, 489 [M+H]$^+$

The following compounds are obtained analogously to Example IX:

(1) 5-(3,5-dichloro-phenylsulphonylamino)-naphthalene-1-carboxylic acid-benzylamide

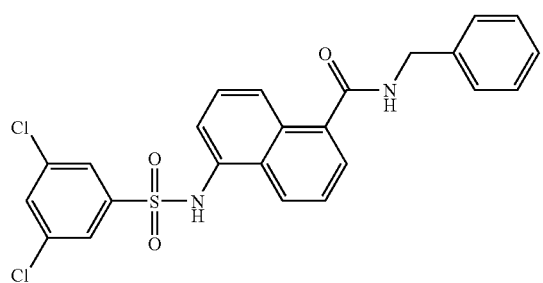

$R_f$ value: 0.58 (silica gel, methylene chloride/methanol=95:5)

Mass spectrum (ESI$^-$): m/z=483, 485, 487 [M−H]$^-$ (2) 5-(3,5-dichloro-phenylsulphonylamino)-naphthalene-1-carboxylic acid-N-methyl-benzylamide

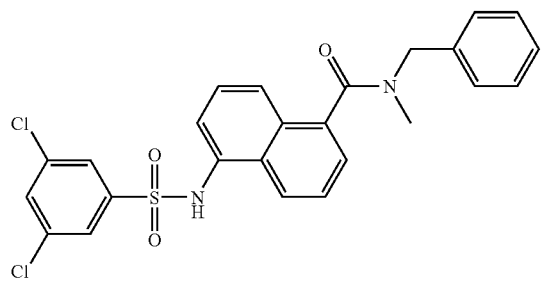

$R_f$ value: 0.33 (silica gel, methylene chloride/methanol=95:5)

Mass spectrum (EI): m/z=498, 500, 502 [M]$^+$ (3) 5-(3,5-dichloro-phenylsulphonylamino)-naphthalene-1-carboxylic acid-phenylethylamide

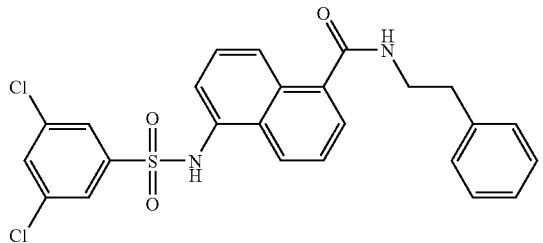

$R_f$ value: 0.27 (silica gel, methylene chloride/methanol=95:5)

Mass spectrum (ESI$^+$): m/z=499, 501, 503 [M+H]$^+$ (4) 6-(3,5-dichloro-phenylsulphonylamino)-naphthalen-1-carboxylic acid-methylamide

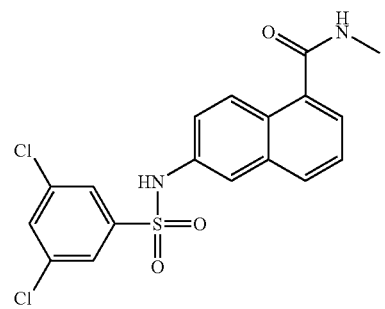

$R_f$ value: 0.22 (silica gel, petroleum ether/ethyl acetate=1:1)

Mass spectrum (ESI$^+$): m/z=409, 411, 413 [M+H]$^+$ (5) 6-(3,5-dichloro-phenylsulphonylamino)-naphthalene-1-carboxylic acid-4-cyano-benzylamide

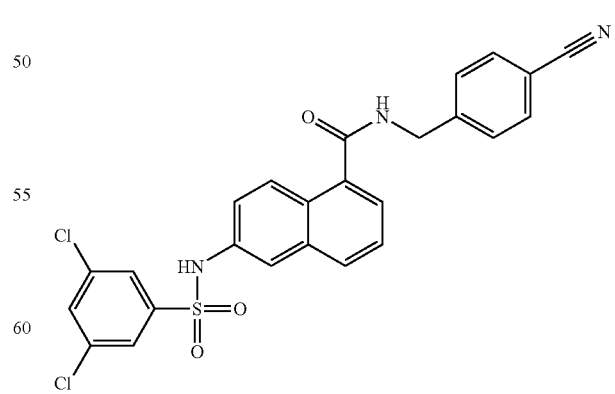

$R_f$ value: 0.37 (silica gel, petroleum ether/ethyl acetate=1:1)

Mass spectrum (ESI$^-$): m/z=508, 510, 512 [M−H]$^-$ (6) 6-amino-naphthalene-1-carboxylic acid-methylamide

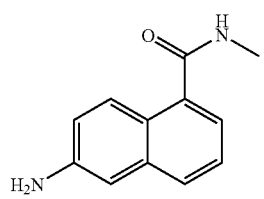

R$_f$ value: 0.40 (silica gel, ethyl acetate)

(7) 1-amino-2-[(pyrrolidin-1-yl)carbonyl]-naphthalene

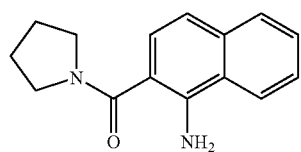

R$_f$ value: 0.15 (silica gel, cyclohexane/ethyl acetate=1:1)
Mass spectrum (ESI$^+$): m/z=241 [M+H]$^+$ (8) 1-amino-naphthalene-2-carboxylic acid-dimethylamide

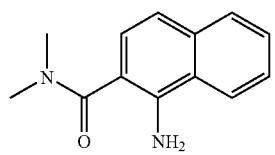

R$_f$ value: 0.13 (silica gel, cyclohexane/ethyl acetate=1:1)
Mass spectrum (ESI$^+$): m/z=215 [M+H]$^+$ Example X 6-(3,5-dichloro-phenylsulphonylamino)-naphthalene-1-carboxylic acid

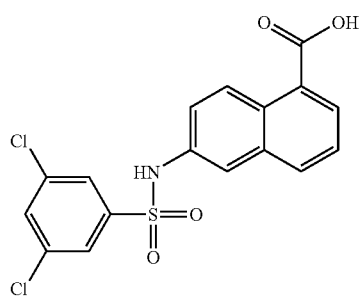

2.68 g 3,5-dichloro-phenylsulphonyl chloride are added to 2.00 g of 6-amino-naphthalene-1-carboxylic acid in 10 ml of pyridine while cooling with an ice bath. The reaction mixture is left overnight to come up to ambient temperature and then the pyridine is distilled off in vacuo using the rotary evaporator. The flask residue is acidified with 3 N hydrochloric acid and extracted with ethyl acetate/methanol. The combined extracts are washed with water, dried on magnesium sulphate and evaporated down. The crude product is purified by chromatography through a silica gel column with cyclohexane/ethyl acetate (65:35 to 0:100) as eluant.

Yield: 3.49 g (82% of theory)
R$_f$ value: 0.55 (silica gel, petroleum ether/ethyl acetate=1:1)
Mass spectrum (ESI$^-$): m/z=394, 396, 398 [M–H]$^-$ The following compounds are obtained analogously to Example X:

(1) 5-(3,5-dichloro-phenylsulphonylamino)-naphthalene-1-carboxylic acid

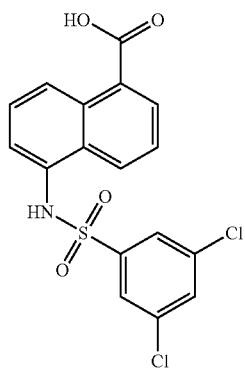

Mass spectrum (ESI$^-$): m/z=394, 396, 398 [M–H]$^-$ (2) 3,5-dichloro-N-(naphthalen-1-yl)-phenylsulphonamide

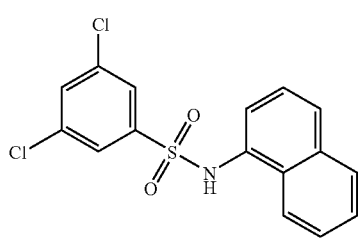

R$_f$ value: 0.40 (silica gel, petroleum ether/ethyl acetate=5:1)
Mass spectrum (ESI$^-$): m/z=350, 352, 354 [M–H]$^-$ (3) 3,5-dichloro-N-[5-(phenylaminocarbonylamino)-naphthalen-1-yl]-phenylsulphonamide

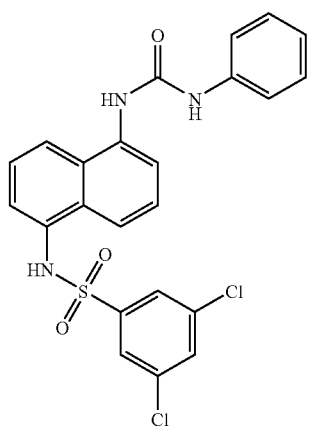

R$_f$ value: 0.68 (silica gel, petroleum ether/ethyl acetate=1:1)
Mass spectrum (ESI$^+$): m/z=486, 488, 490 [M+H]$^+$ (4) 3,5-dichloro-N-(6-pyrimidin-2-yl-naphthalen-2-yl)-phenylsulphonamide

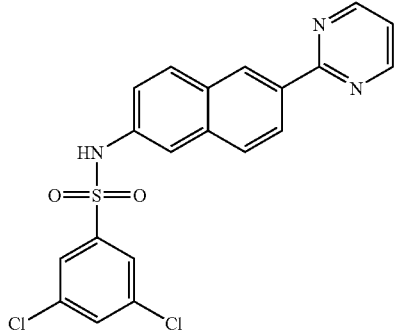

R$_f$ value: 0.57 (silica gel, petroleum ether/ethyl acetate=1:1)

(5) 3,5-dichloro-N-(2-methyl-naphthalen-1-yl)-phenylsulphonamide

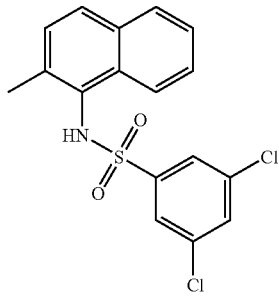

R$_f$ value: 0.80 (silica gel, cyclohexane/ethyl acetate=1:1)
Mass spectrum (ESI$^-$): m/z=364, 366, 368 [M–H]$^-$ (6) 6-(3,5-dimethyl-phenylsulphonylamino)-naphthalene-1-carboxylic acid-methylamide

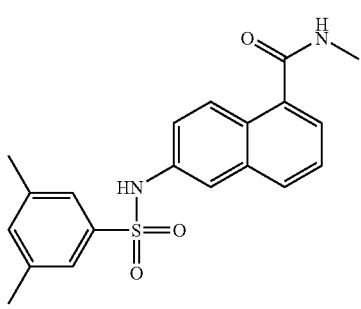

R$_f$ value: 0.58 (silica gel, ethyl acetate)
Mass spectrum (ESI$^+$): m/z=369 [M+H]$^+$ (7) 3,5-dibromo-N-(naphthalen-1-yl)-phenylsulphonamide

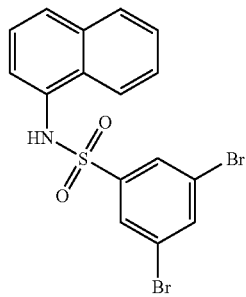

R$_f$ value: 0.47 (silica gel, petroleum ether/ethyl acetate=5:1)
Mass spectrum (ESI$^-$): m/z=438, 440, 442 [M–H]$^-$ (8) 5-(3,5-dichloro-phenylsulphonylamino)-naphthalene-1-sulphonic acid-dimethylamide

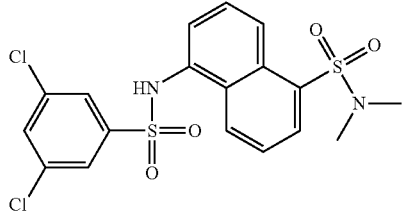

R$_f$ value: 0.40 (silica gel, petroleum ether/ethyl acetate=2:1)
Mass spectrum (ESI$^+$): m/z=459, 461, 463 [M+H]$^+$ (9) 3,5-dichloro-N-(quinolin-8-yl)-phenylsulphonamide

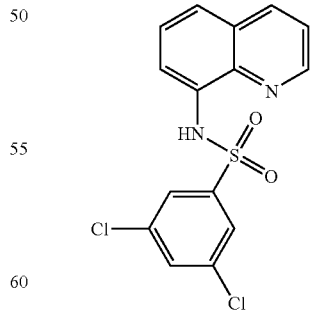

R$_f$ value: 0.47 (silica gel, petroleum ether/ethyl acetate=2:3)
Mass spectrum (ESI$^+$): m/z=353, 355, 357 [M+H]$^+$

(10) 3,5-dichloro-N-(quinolin-5-yl)-phenylsulphonamide

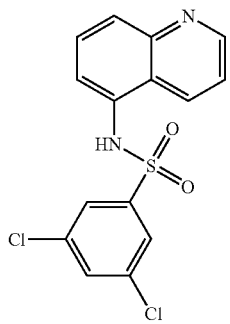

$R_f$ value: 0.44 (silica gel, petroleum ether/ethyl acetate=2:3)
Mass spectrum (ESI$^+$): m/z=353, 355, 357 [M+H]$^+$

(11) 3-chloro-5-methyl-N-(naphthalen-1-yl)-phenyl-sulphonamide

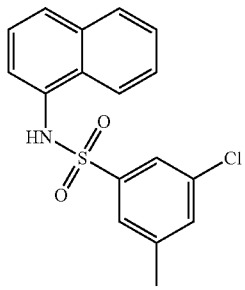

$R_f$ value: 0.70 (silica gel, methylene chloride)
Mass spectrum (ESI$^-$): m/z=330, 332 [M−H]$^-$

(12) 3,5-dimethyl-N-(naphthalen-1-yl)-phenylsulphonamide

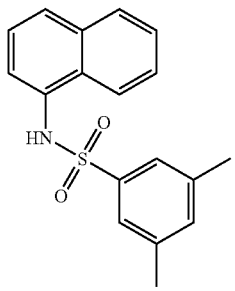

$R_f$ value: 0.63 (silica gel, methylene chloride)
Mass spectrum (ESI$^+$): m/z=329 [M+NH$_4$]$^+$

(13) 3-bromo-5-chloro-N-(naphthalen-1-yl)-phenyl-sulphonamide

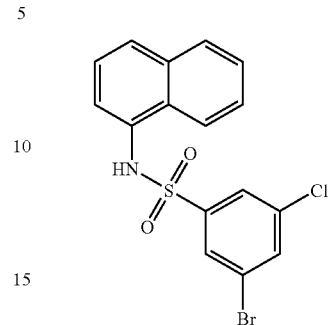

$R_f$ value: 0.42 (silica gel, petroleum ether/ethyl acetate=5:1)
Mass spectrum (ESI$^-$): m/z=394, 396, 398 [M−H]$^-$

(14) 3-chloro-5-fluoro-N-(naphthalen-1-yl)phenyl-sulphonamide

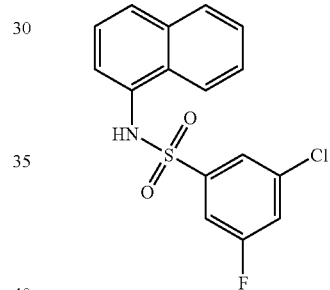

$R_f$ value: 0.40 (silica gel, petroleum ether/ethyl acetate=5:1)
Mass spectrum (ESI$^-$): m/z=334, 336 [M−H]$^-$

(15) 3,5-dichloro-N-(3-methyl-naphthalen-2-yl)-phenylsulphonamide

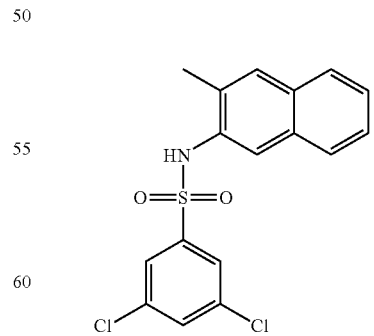

$R_f$ value: 0.85 (silica gel, cyclohexane/ethyl acetate=1:1)
Mass spectrum (ESI$^-$): m/z=364, 366, 368 [M−H]$^-$

(16) 3,5-dichloro-N-(quinoxalin-6-yl)-phenylsulphonamide

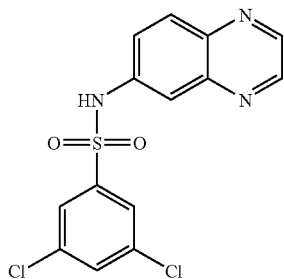

R$_f$ value: 0.56 (silica gel, petroleum ether/ethyl acetate=2:3)

Mass spectrum (ESI$^-$): m/z=352, 354, 356 [M−H]$^-$

(17) 3,5-dichloro-N-(quinolin-3-yl)-phenylsulphonamide

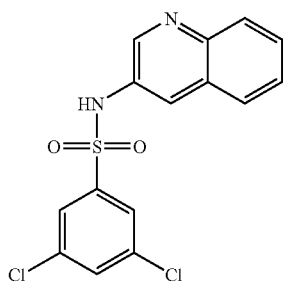

R$_f$ value: 0.72 (silica gel, petroleum ether/ethyl acetate=2:3)

Mass spectrum (ESI$^+$): m/z=353, 355, 357 [M+H]$^+$

(18) 3,5-dichloro-N-(quinolin-6-yl)-phenylsulphonamide

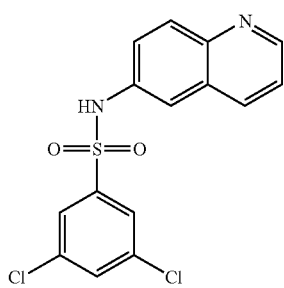

R$_f$ value: 0.72 (silica gel, petroleum ether/ethyl acetate=2:3)

Mass spectrum (ESI$^+$): m/z=353, 355, 357 [M+H]$^+$

(19) 3,5-dichloro-N-(2-cyano-naphthalen-1-yl)-phenylsulphonamide

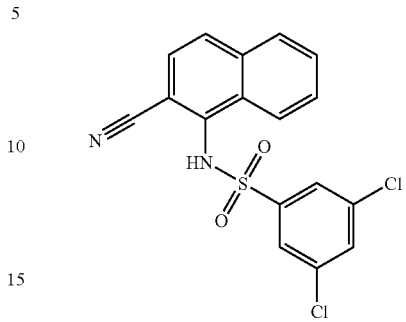

R$_f$ value: 0.22 (silica gel, petroleum ether/ethyl acetate=5:1)

Mass spectrum (ESI$^-$): m/z=375, 377, 379 [M−H]$^-$

(20) 3-bromo-5-methyl-N-(naphthalen-1-yl)-phenylsulphonamide

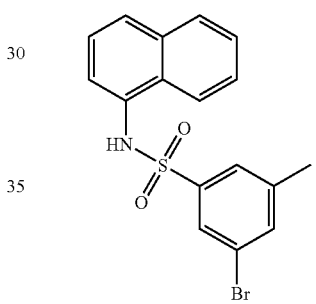

R$_f$ value: 0.35 (silica gel, petroleum ether/ethyl acetate=5:1)

Mass spectrum (ESI$^-$): m/z=374, 376 [M−H]$^-$

(21) 3,5-dichloro-N-(2-chloro-naphthalen-1-yl)-phenylsulphonamide

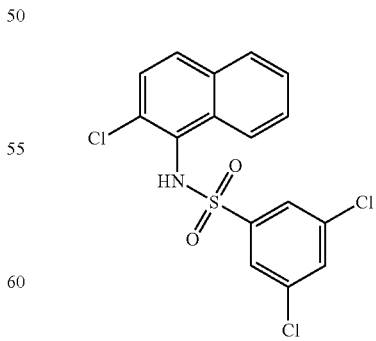

R$_f$ value: 0.45 (silica gel, petroleum ether/ethyl acetate=5:1)

Mass spectrum (EI): m/z=385, 387, 389, 391 [M]$^+$

(22) 3,5-dichloro-N-(5-methoxy-naphthalen-1-yl)-phenylsulphonamide

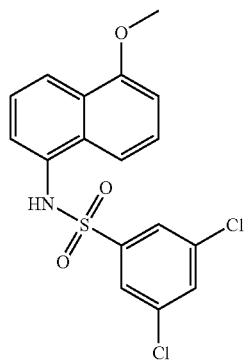

R$_f$ value: 0.80 (silica gel, cyclohexane/ethyl acetate=1:1)
Mass spectrum (ESI⁻): m/z=380, 382, 384 [M–H]⁻

(23) 3-chloro-N-(naphthalen-1-yl)-5-trifluoromethyl-phenylsulphonamide

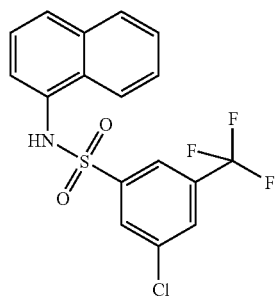

R$_f$ value: 0.50 (silica gel, petroleum ether/ethyl acetate=5:1)
Mass spectrum (ESI⁻): m/z=384, 386 [M–H]⁻

(24) 3,5-dichloro-N-(4-methoxy-naphthalen-1-yl)-phenylsulphonamide

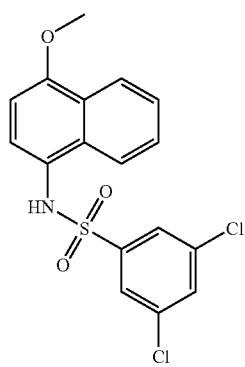

R$_f$ value: 0.79 (silica gel, petroleum ether/ethyl acetate=3:2)
Mass spectrum (ESI⁻): m/z=380, 382, 384 [M–H]⁻

(25) 3,5-dichloro-N-(2-bromo-naphthalen-1-yl)-phenylsulphonamide

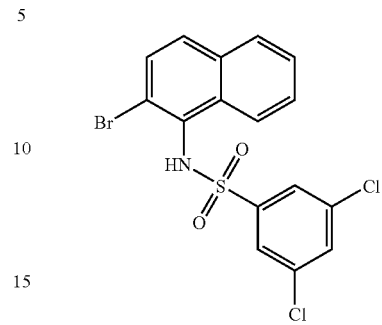

Mass spectrum (EI): m/z=429, 431, 433, 435 [M]⁺

(26) 3,5-dichloro-N-(7-methyl-quinolin-8-yl)-phenylsulphonamide

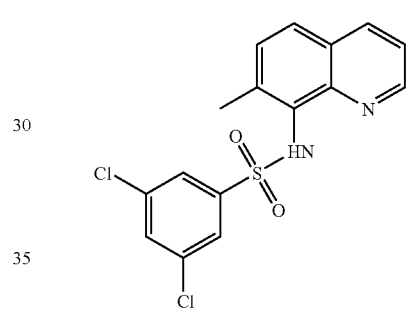

R$_f$ value: 0.75 (silica gel, petroleum ether/ethyl acetate=3:2)
Mass spectrum (ESI⁺): m/z=367, 369, 371 [M+H]⁺

(27) 3,5-dichloro-N-(2-methyl-quinolin-8-yl)-phenylsulphonamide

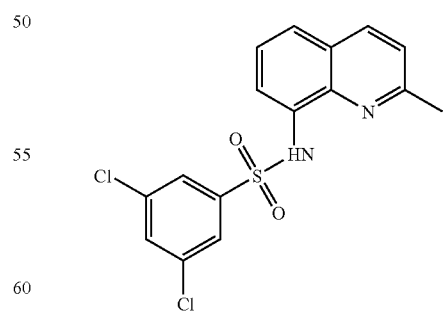

R$_f$ value: 0.86 (silica gel, petroleum ether/ethyl acetate=1:4)
Mass spectrum (ESI⁺): m/z=367, 369, 371 [M+H]⁺

(28) 3,5-dichloro-N-(2-methoxy-naphthalen-1-yl)-phenylsulphonamide

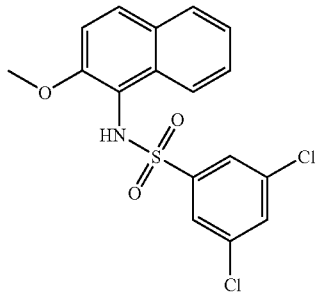

$R_f$ value: 0.81 (silica gel, petroleum ether/ethyl acetate=1:1)

Mass spectrum (ESI⁻): m/z=380, 382, 384 [M−H]⁻

(29) 3,5-dichloro-N-(2-trimethylsilanylethynyl-naphthalen-1-yl)-phenylsulphonamide

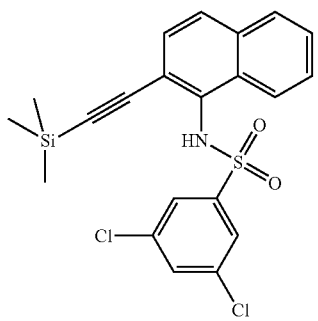

$R_f$ value: 0.46 (silica gel, petroleum ether/ethyl acetate=9:1)

Mass spectrum (ESI⁻): m/z=446, 448, 450 [M−H]⁻

(30) 3,5-dichloro-N-(2-phenylethynyl-naphthalen-1-yl)-phenylsulphonamide

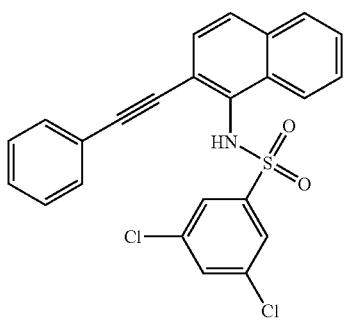

$R_f$ value: 0.18 (silica gel, petroleum ether/methylene chloride=7:3)

(31) 3-chloro-5-cyano-N-(naphthalen-1-yl)-phenylsulphonamide

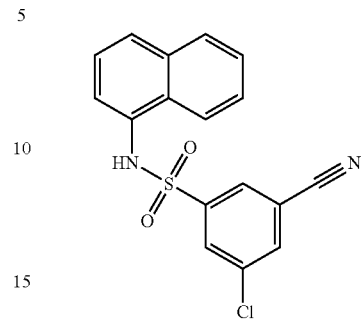

$R_f$ value: 0.62 (silica gel, petroleum ether/ethyl acetate=2:1)

Mass spectrum (ESI⁻): m/z=341, 343 [M−H]⁻

(32) N-(2-benzothiazol-2-yl-naphthalen-1-yl)-3,5-dichloro-phenylsulphonamide

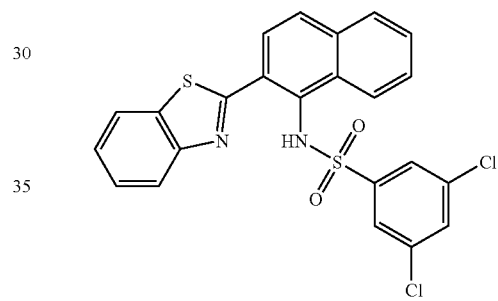

$R_f$ value: 0.50 (silica gel, petroleum ether/methylene chloride=3:7)

Mass spectrum (ESI⁺): m/z=485, 487, 489 [M+H]⁺

(33) 3,5-dichloro-4-fluoro-N-(naphthalen-1-yl)phenylsulphonamide

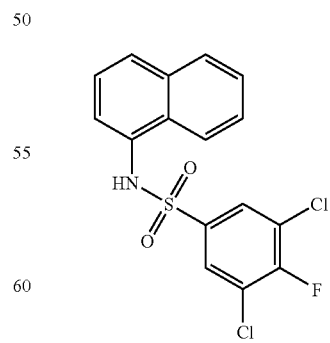

$R_f$ value: 0.36 (silica gel, petroleum ether/ethyl acetate=5:1)

Mass spectrum (ESI⁻): m/z=368, 370, 372 [M−H]⁻

(34) 1-(3,5-dichloro-phenylsulphonylamino)-naphthalene-2-carboxylic acid-benzylamide

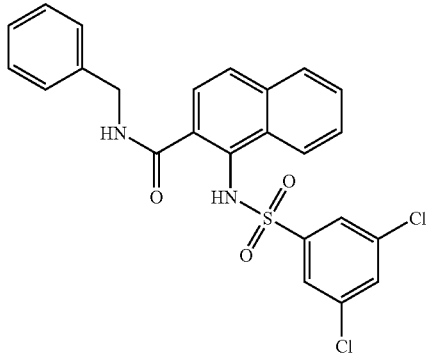

$R_f$ value: 0.93 (silica gel, methylene chloride/methanol=95:5)
Mass spectrum (ESI⁺): m/z=485, 487, 489 [M+H]⁺

(35) 3,5-dichloro-N-[2-(pyrrolidin-1-carbonyl)-naphthalen-1-yl]-phenylsulphonamide

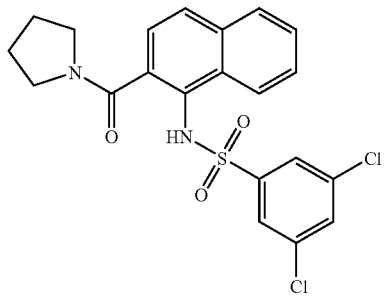

$R_f$ value: 0.50 (silica gel, methylene chloride/methanol=98:2)
Mass spectrum (ESI⁺): m/z=449, 451, 453 [M+H]⁺

(36) (2-benzoxazol-2-yl-naphthalen-1-yl)-bis(3,5-dichloro-phenylsulphonyl)-amine

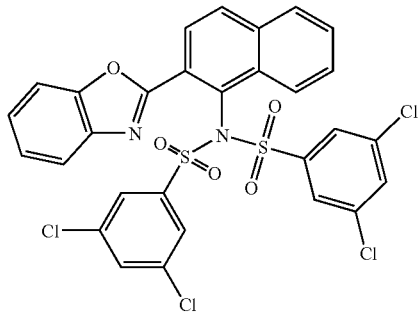

$R_f$ value: 0.55 (silica gel, methylene chloride)
Mass spectrum (ESI⁺): m/z=677, 679, 681 [M+H]⁺

(37) 1-(3,5-dichloro-phenylsulphonylamino)-naphthalene-2-carboxylic acid-dimethylamide

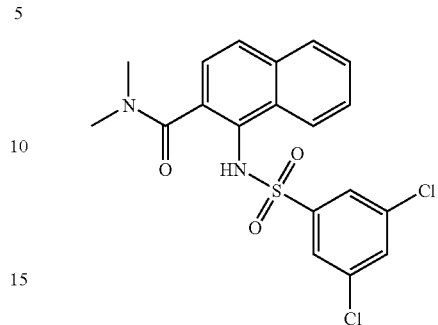

$R_f$ value: 0.35 (silica gel, methylene chloride/methanol=98:2)
Mass spectrum (ESI⁺): m/z=423, 425, 427 [M+H]⁺

(38) 3-chloro-N-(naphthalen-1-yl)-5-nitro-phenylsulphonamide

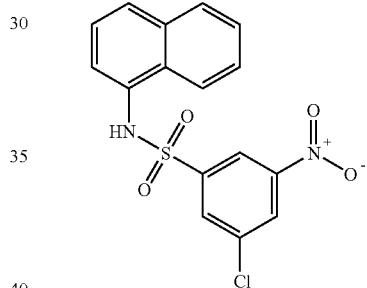

$R_f$ value: 0.80 (silica gel, cyclohexane/ethyl acetate=1:1)
Mass spectrum (ESI⁻): m/z=361, 363 [M−H]⁻

(39) 3,5-dichloro-N-(3-methyl-cinnolin-5-yl)-phenylsulphonamide

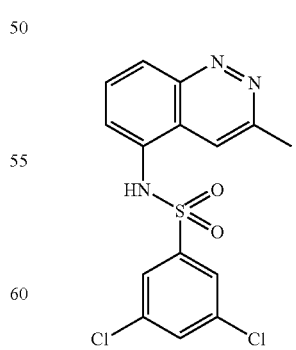

$R_f$ value: 0.66 (silica gel, ethyl acetate)
Mass spectrum (ESI⁺): m/z=368, 370, 372 [M+H]⁺

63

(40) 3,5-dichloro-N-(3-methyl-isoquinolin-5-yl)-phenylsulphonamide

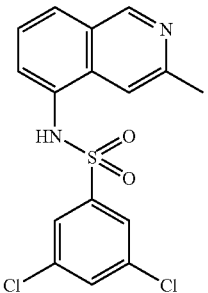

R$_f$ value: 0.48 (silica gel, petroleum ether/ethyl acetate=1:2)

Mass spectrum (ESI$^+$): m/z=367, 369, 371 [M+H]$^+$

(41) 3,5-dichloro-N-(quinoxalin-5-yl)-phenylsulphonamide

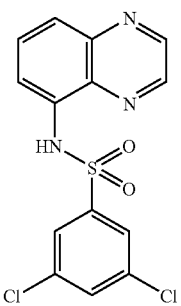

R$_f$ value: 0.37 (silica gel, petroleum ether/ethyl acetate=1:2)

Mass spectrum (ESI$^-$): m/z=352, 354, 356 [M−H]$^-$

(42) 3,5-dichloro-N-(quinoline-7-yl)-phenylsulphonamide

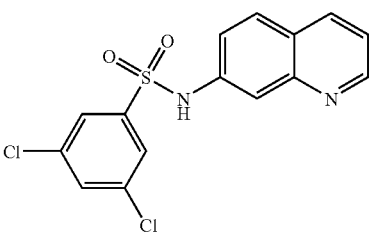

R$_f$ value: 0.53 (silica gel, methylene chloride/methanol=95:5)

Mass spectrum (ESI$^+$): m/z=353, 355, 357 [M+H]$^+$

64

(43) 3,5-dichloro-N-(3-methyl-quinolin-5-yl)-phenylsulphonamide

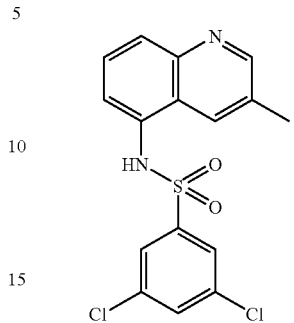

R$_f$ value: 0.58 (silica gel, petroleum ether/ethyl acetate=1:2)

Mass spectrum (ESI$^+$): m/z=367, 369, 371 [M+H]$^+$

(44) 3,5-dichloro-N-(4-dimethylamino-quinazolin-8-yl)-phenylsulphonamide

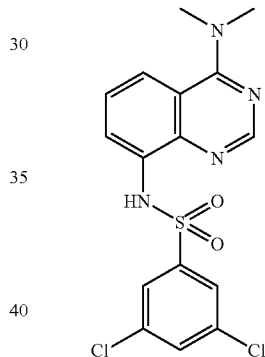

Mass spectrum (ESI$^+$): m/z=397, 399, 401 [M+H]$^+$

(45) 3,5-dichloro-N-(quinazolin-8-yl)-phenylsulphonamide

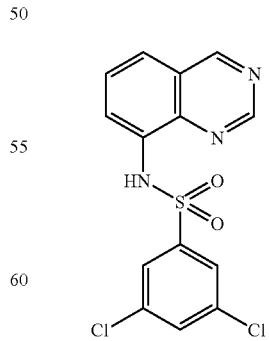

R$_f$ value: 0.50 (silica gel, methylene chloride/methanol=9:1)

Mass spectrum (ESI$^-$): m/z=352, 354, 356 [M−H]$^-$

(46) (2-phenylcarbonyl-naphthalen-1-yl)-bis(3,5-dichloro-phenylsulphonyl)-amine

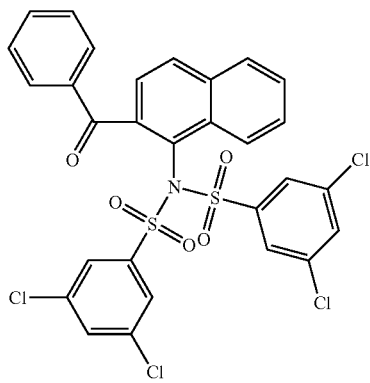

$R_f$ value: 0.27 (silica gel, petroleum ether/ethyl acetate=9:1)

Mass spectrum (ESI$^+$): m/z=664, 666, 668 [M+H]$^+$

Example XI

Diethyl ({(3,5-dichloro-phenylsulphonyl)-[6-(phenylaminocarbonylamino)-naphthalen-2-yl]-amino}-methyl)-phosphonate

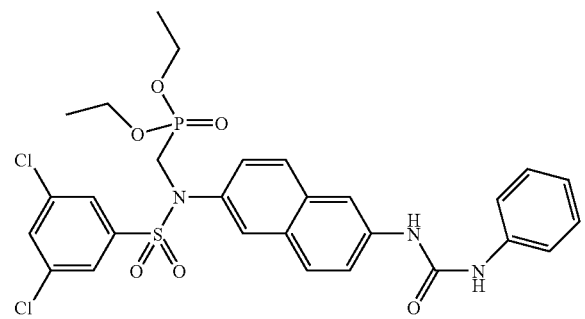

A mixture of 25 mg diethyl {[(6-amino-naphthalen-2-yl)-(3,5-dichloro-phenylsulphonyl)-amino]-methyl}-phosphonate and 7 µl phenylisocyanate in 2 ml of tetrahydrofuran is refluxed for three and a half hours. Then another 4 µl phenylisocyanate are added. After a further two hours the reaction is complete and the reaction mixture is evaporated down. The flask residue is chromatographed through a silica gel column with cyclohexane/ethyl acetate (30:70 to 0:100) as eluant.

Yield: 30 mg (98% of theory)

$R_f$ value: 0.30 (silica gel, methylene chloride/methanol=95:5)

Mass spectrum (ESI$^+$): m/z=636, 638, 640 [M+H]$^+$

The following compounds are obtained analogously to Example XI:

(1) 1-(5-amino-naphthalen-1-yl)-3-phenyl-urea

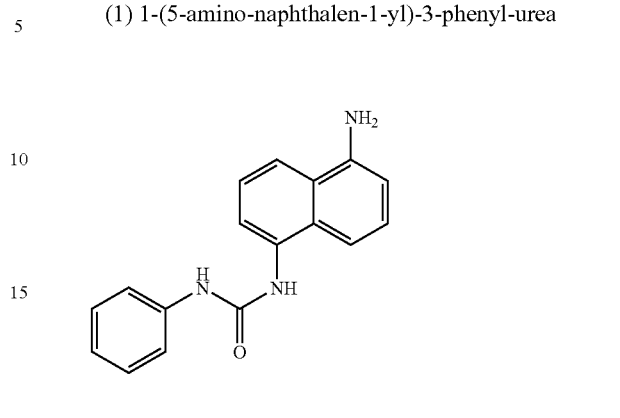

$R_f$ value: 0.36 (silica gel, petroleum ether/ethyl acetate=1:1)

Mass spectrum (ESI$^+$): m/z=278 [M+H]$^+$

Example XII

Diethyl {[(6-amino-naphthalen-2-yl)-(3,5-dichloro-phenylsulphonyl)-amino]-methyl}-phosphonate

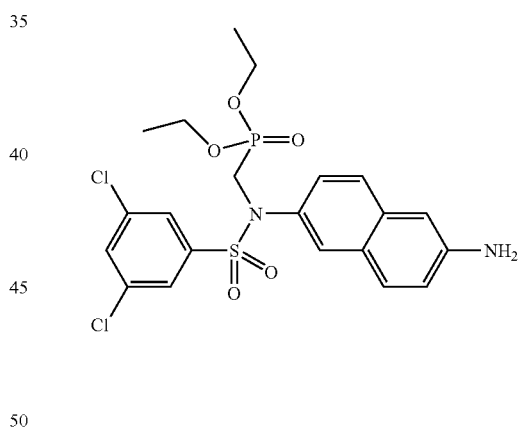

1 ml trifluoroacetic acid is pipetted into 130 mg diethyl {[(6-tert.-butoxycarbonylamino-naphthalen-2-yl)-(3,5-dichloro-phenylsulphonyl)-amino]-methyl}-phosphonate in 3 ml methylene chloride. The reaction mixture is stirred for two and a half hours at ambient temperature, then made alkaline with 1 N sodium hydroxide solution and extracted with methylene chloride. The combined organic phases are washed with saturated sodium chloride solution, dried on magnesium sulphate and evaporated down. The flask residue is chromatographed through a silica gel column with cyclohexane/ethyl acetate (40:60 to 0:100).

Yield: 60 mg (55% of theory)

$R_f$ value: 0.22 (silica gel, petroleum ether/ethyl acetate=1:2)

Mass spectrum (ESI$^+$): m/z=517, 519, 521 [M+H]$^+$

The following compounds are obtained analogously to Example XII:

(1) 6-(pyrimidin-2-yl)-naphthalen-2-ylamine

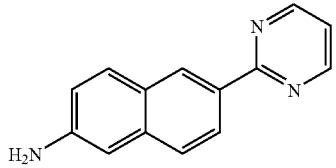

R$_f$ value: 0.20 (silica gel, petroleum ether/ethyl acetate=2:1)

Example XIII

Diethyl {[(6-benzylcarbonylamino-naphthalen-2-yl)-(3,5-dichloro-phenylsulphonyl)-amino]-methyl}-phosphonate

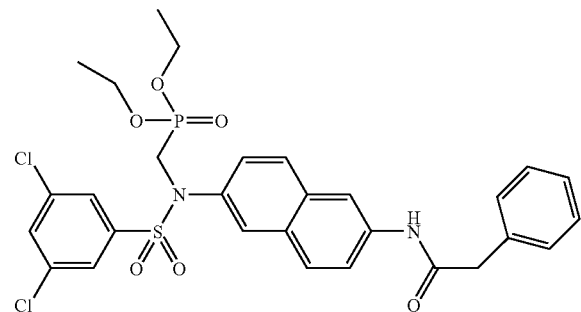

A mixture of 30 mg diethyl {[(6-amino-naphthalen-2-yl)-(3,5-dichloro-phenylsulphonyl)-amino]-methyl}-phosphonate and 12 µl triethylamine in 3 ml methylene chloride is combined with 8.5 µl phenylacetyl chloride and stirred overnight at ambient temperature. The crude mixture is applied to silica gel and chromatographed through a silica gel column with cyclohexane/ethyl acetate (40:60 to 0:100) as eluant.
Yield: 30 mg (81% of theory)
R$_f$ value: 0.56 (silica gel, ethyl acetate)
Mass spectrum (ESI$^+$): m/z=635, 637, 639 [M+H]$^+$

Example XIV 2-(tert.-butoxycarbonylamino)-6-(pyrimidin-2-yl)-naphthalene

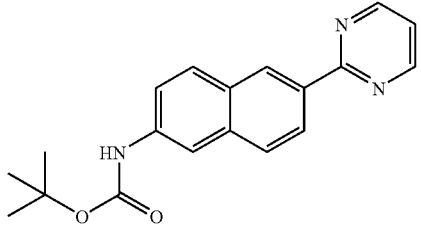

A mixture of 400 mg 6-tert.-butoxycarbonylamino-naphthalene-2-boronic acid, 258 mg 2-bromo-pyrimidine, 100 mg tetrakis(triphenylphosphine)palladium and 4 ml 1 M sodium carbonate solution in 15 ml dioxane and 5 ml of methanol is refluxed for four hours in an argon atmosphere. After cooling to ambient temperature the reaction mixture is divided between ethyl acetate and water. The organic phase is dried on magnesium sulphate and evaporated down. The flask residue is chromatographed through a silica gel column with cyclohexane/ethyl acetate (75:25 to 50:50) as eluant.
Yield: 280 mg (63% of theory)
R$_f$ value: 0.63 (silica gel, petroleum ether/ethyl acetate=1:1)
Mass spectrum (ESI$^+$): m/z=322 [M+H]$^+$

Example XV 3,5-dichloro-N-(5-cyano-naphthalen-1-yl)-phenyl-sulphonamide

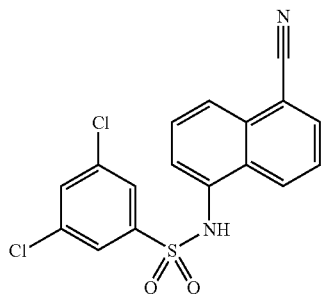

0.49 ml trifluoroacetic anhydride are added dropwise to a mixture of 1.13 g 5-(3,5-dichloro-phenylsulphonylamino)-naphthalene-1-carboxylic acid amide and 1.07 ml triethylamine in 50 ml methylene chloride while cooling with an ice bath. Then the ice bath is removed and the reaction mixture is stirred for one hour at ambient temperature. In all, another 1.00 ml triethylamine and 0.70 ml trifluoroacetic anhydride are added successively and the reaction mixture is stirred overnight at ambient temperature. For working up the mixture is combined with 50 ml of water. The organic phase is washed with 2 N citric acid solution and saturated sodium hydrogen carbonate solution, dried on magnesium sulphate and evaporated down. The flask residue is chromatographed through a silica gel column with cyclohexane/ethyl acetate (85:15 to 65:35).
Yield: 395 mg (37% of theory)
R$_f$ value: 0.82 (silica gel, petroleum ether/ethyl acetate=1:1)

Example XVI 5-(3,5-dichloro-phenylsulphonylamino)-naphthalene-1-carboxylic acid amide

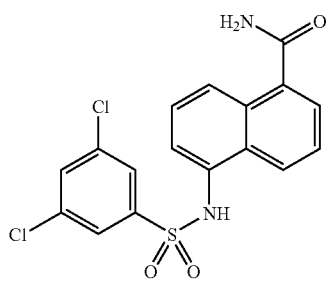

N,N'-carbonyldiimidazole are added to 1.13 g 5-(3,5-dichloro-phenylsulphonylamino)-naphthalene-1-carboxylic acid in 15 ml of tetrahydrofuran and the reaction mixture is stirred for 45 minutes at 60° C. Then ammonia gas is piped in at ambient temperature over a period of 25 minutes. The dark reaction solution is evaporated down using the rotary evaporator and the solid residue is stirred with water. Then it is acidified with 1 N hydrochloric acid and the precipitate formed is suction filtered, washed with water and dried in vacuo in the desiccator.

Yield: 1.13 g (100% of theory)

$R_f$ value: 0.17 (silica gel, petroleum ether/ethyl acetate=1:1)

Mass spectrum (ESI$^+$): m/z=395, 397, 399 [M+H]$^+$

Example XVII 3-chloro-5-methyl-phenylsulphonyl chloride

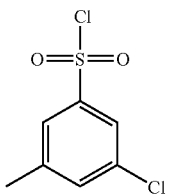

A solution of 400 mg of sodium nitrite in 0.6 ml of water is added dropwise to 708 mg 3-chloro-5-methyl-aniline in 2 ml concentrated hydrochloric acid while being cooled in a bath of ice and common salt. The reaction mixture is stirred for 15 minutes at 0° C. and then added to a mixture of 4 ml of a saturated solution of sulphur dioxide in glacial acetic acid (approx. 30%) and 200 mg copper(II)chloride-dihydrate in 0.4 ml of water while being cooled. The cooling bath is removed and the reaction mixture is stirred for 15 minutes at ambient temperature, then at 40° C., until no further development of gas can be detected. Then some ice water is added while cooling with an ice bath. After 5 minutes the precipitate formed is suction filtered, washed with some ice water and dried in the desiccator. The sulphonyl chloride obtained is reacted further without any further purification.

Yield: 760 mg (68% of theory)

The following compounds are obtained analogously to Example XVII:

(1) 3-bromo-5-chloro-phenylsulphonyl chloride

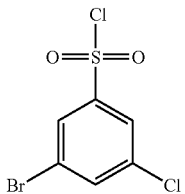

(2) 3-chloro-5-fluoro-phenylsulphonyl chloride

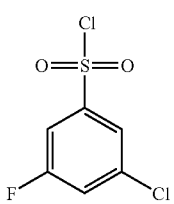

(3) 3-bromo-5-methyl-phenylsulphonyl chloride

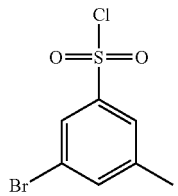

(4) 3-chloro-5-trifluoromethyl-phenylsulphonyl chloride

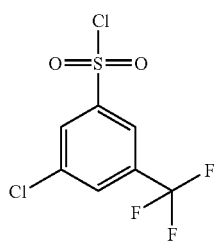

(5) 3-chloro-5-cyano-phenylsulphonyl chloride

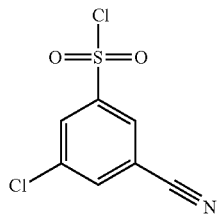

(6) 3,5-dichloro-4-fluoro-phenylsulphonyl chloride

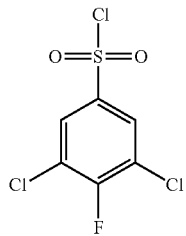

(7) 3-chloro-5-nitro-phenylsulphonyl chloride

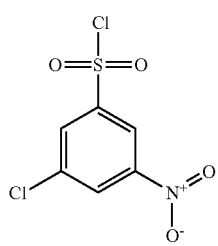

$R_f$ value: 0.40 (silica gel, petroleum ether/ethyl acetate=9:1)

Example XVIII

Diethyl {[(3,5-dichloro-phenylsulphonyl)-(2-ethynyl-naphthalen-1-yl)-amino]-methyl}-phosphonate

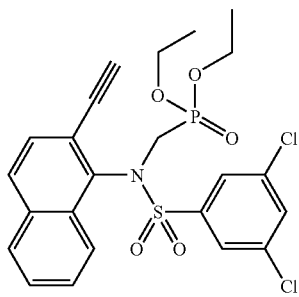

115 mg tetrabutylammonium fluoridetrihydrate are added to 155 mg diethyl {[(3,5-dichloro-phenylsulphonyl)-(2-trimethylsilanylethynyl-naphthalen-1-yl)-amino]-methyl}-phosphonate in 4 ml of tetrahydrofuran at ambient temperature. The reaction mixture is stirred for 15 minutes at ambient temperature, then it is mixed with water and extracted with ethyl acetate. The combined extracts are dried on magnesium sulphate and evaporated down. The flask residue is chromatographed through a silica gel column with cyclohexane/ethyl acetate (50:50) as eluant.

Yield: 90 mg (66% of theory)
$R_f$ value: 0.25 (silica gel, petroleum ether/ethyl acetate=1:1)
Mass spectrum (ESI$^+$): m/z=526, 528, 530 [M+H]$^+$

Example XIX

2-Trimethylsilanylethynyl-naphthalen-1-ylamine

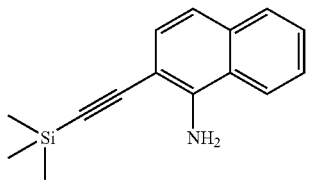

10 mg copper(I)iodide are added to 250 mg 2-iodo-naphthalen-1-ylamine in triethylamine under an argon atmosphere. The mixture is stirred vigorously for 10 minutes at 50° C., then 30 mg of bis(triphenylphosphine)palladium(II)chloride and 0.20 ml trimethylsilylacetylene are added. The reaction mixture is stirred for one hour at 50° C., then mixed with water and extracted with ethyl acetate. The combined extracts are washed with saturated sodium chloride solution, dried and evaporated down. The flask residue is chromatographed through a silica gel column with cyclohexane/ethyl acetate (98:2) as eluant.

Yield: 200 mg (90% of theory)
$R_f$ value: 0.65 (silica gel, petroleum ether/ethyl acetate=5:1)
Mass spectrum (ESI$^+$): m/z=479 [2M+H]$^+$ The following compound is obtained analogously to Example XIX:

(1) 2-phenylethynyl-naphthalen-1-ylamine

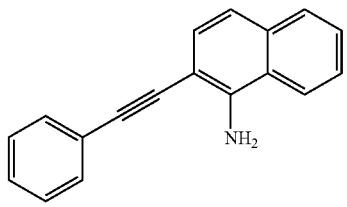

$R_f$ value: 0.44 (silica gel, petroleum ether/ethyl acetate=5:1)
Mass spectrum (ESI$^+$): m/z=244 [M+H]$^+$

Example XX 1-amino-naphthalene-2-carboxylic acid-benzylamide

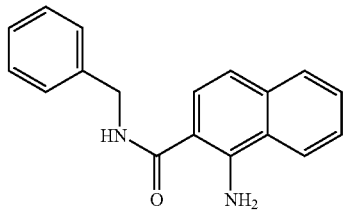

A mixture of 200 mg 1H-naphtho[1,2-d][1,3]oxazin-2,4-dione in 6 ml dioxane is heated in a warm oil bath at 90° C., then 0.41 ml benzylamine are added. First of all a clear solution is obtained from which a thick precipitate settles out after a few minutes. The reaction mixture is stirred for another 1.5 hours at 80° C. and then cooled to ambient temperature.

The precipitate formed is suction filtered, washed with a little dioxane and dried. 167 mg of 1-(3-benzyl-ureido)-naphthalene-2-carboxylate-benzyl-ammonium salt are obtained as colourless crystals.

The combined dioxane filtrates are evaporated down. The flask residue is stirred with water and a little methanol and made weakly acidic with citric acid. The precipitate formed is suction filtered, washed with water and a very little methanol and dried.

Yield: 129 mg (50% of theory)
$R_f$ value: 0.80 (silica gel, methylene chloride/methanol=95:5)
Mass spectrum (ESI$^+$): m/z=277 [M+H]$^+$

Example XXI

N-(2-benzoxazol-2-yl-naphthalen-1-yl)-3,5-dichloro-phenylsulphonamide

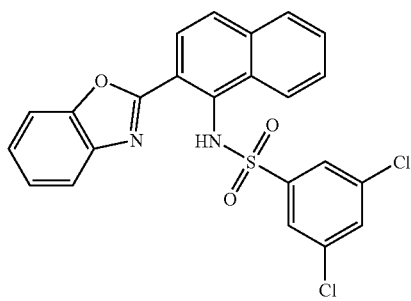

0.5 ml Tetrabutylammonium fluoride solution (1 M in tetrahydrofuran) are added to 220 mg (2-benzoxazol-2-yl-naphthalen-1-yl)-bis(3,5-dichloro-phenylsulphonyl)-amine in 6 ml of tetrahydrofuran under an argon atmosphere and the reaction mixture is stirred for one hour at ambient temperature. For working up the reaction solution is combined with water and tert.-butylmethylether. The organic phase is washed with water and saturated sodium chloride solution, dried on magnesium sulphate and evaporated down.

Yield: 122 mg (99% of theory)

$R_f$ value: 0.70 (silica gel, methylene chloride)

Mass spectrum (ESI$^+$): m/z=469, 471, 473 [M+H]$^+$

The following compounds are obtained analogously to Example XXI:

(1) N-(2-phenylcarbonyl-naphthalen-1-yl)-3,5-dichloro-phenylsulphonamide

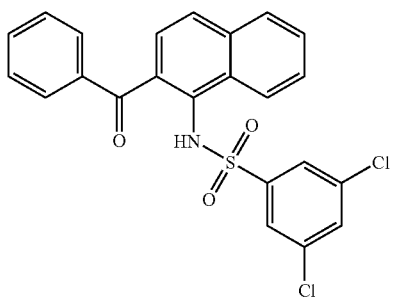

$R_f$ value: 0.65 (silica gel, methylene chloride)

Mass spectrum (ESI$^-$): m/z=454, 456, 458 [M−H]$^-$

Example XXII

Diethyl {[(3-amino-5-chloro-phenylsulphonyl)-naphthalen-1-yl-amino]-methyl}-phosphonate

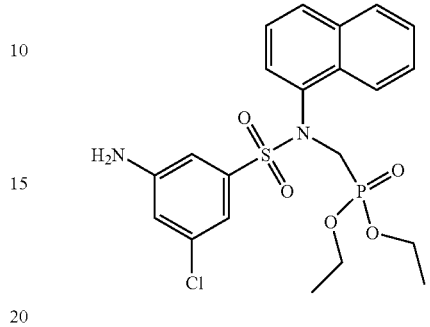

290 mg diethyl {[(3-chloro-5-nitro-phenylsulphonyl)-naphthalen-1-yl-amino]-methyl}-phosphonate in 25 ml of tetrahydrofuran and 15 ml of water are combined with 1.16 g sodium dithionite and stirred overnight at ambient temperature. For working up the reaction mixture is diluted with ethyl acetate, washed with saturated sodium hydrogen carbonate solution, water and saturated sodium chloride solution, dried on magnesium sulphate and evaporated down. The flask residue is chromatographed through a silica gel column with methylene chloride/methanol (97:3) as eluant.

Yield: 197 mg (72% of theory)

$R_f$ value: 0.45 (silica gel, methylene chloride/methanol=97:3)

Mass spectrum (ESI$^+$): m/z=483, 485 [M+H]$^+$

Example XXIII 8-amino-4-dimethylamino-quinazoline

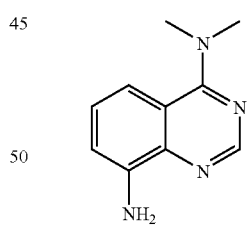

360 mg 8-nitro-4-dimethylamino-quinazolin in ethanol are hydrogenated in the presence of 50 mg palladium on charcoal (10%) at ambient temperature and 1 bar hydrogen pressure, until the calculated amount of hydrogen has been taken up. Then the catalyst is suction filtered and the filtrate is evaporated down in vacuo. The flask residue is chromatographed through a silica gel column with methylene chloride/methanol (98:2 to 90:10) as eluant.

Yield: 100 mg (32% of theory)

$R_f$ value: 0.48 (silica gel, methylene chloride/methanol=95:5)

Mass spectrum (ESI$^+$): m/z=189 [M+H]$^+$

Example XXIV 8-nitro-4-dimethylamino-quinazoline

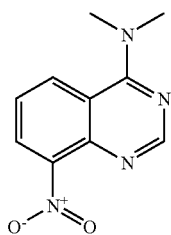

2.40 ml of a solution of dimethylamine in tetrahydrofuran (2 M) are added to 500 mg 4-chloro-8-nitro-quinazoline in 3 ml dioxane and the reaction mixture is stirred for one hour at ambient temperature, then another 1 ml of a solution of dimethylamine in tetrahydrofuran (2 M) is added. The reaction mixture is stirred overnight and then evaporated down in vacuo. The flask residue is chromatographed through a silica gel column with cyclohexane/ethyl acetate (65:35 to 40:60).

Yield: 360 mg (69% of theory)

$R_f$ value: 0.48 (silica gel, petroleum ether/ethyl acetate=1:2)

Mass spectrum (ESI$^+$): m/z=219 [M+H]$^+$

PREPARATION OF THE END COMPOUNDS

Example 1

{[(3,5-dichloro-phenylsulphonyl)-naphthalen-2-yl-amino]-methyl}-phosphonic acid

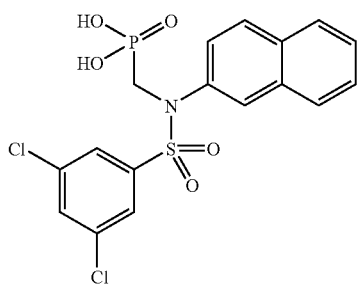

72 mg dibenzyl {[(3,5-dichloro-phenylsulphonyl)-naphthalen-2-yl-amino]-methyl}-phosphonate in 6 ml of methanol are hydrogenated in the presence of 3 mg palladium on activated charcoal (10% Pd). The catalyst is filtered through kieselguhr and the filtrate is evaporated down in vacuo. The flask residue is stirred with diisopropylether, suction filtered and dried.

Yield: 31 mg (60% of theory)

Mass spectrum (ESI): m/z=444, 446, 448 [M−H]$^-$

Example 2

({(3,5-dichloro-phenylsulphonyl)-[6-(5-methyl-[1,2,4]oxadiazol-3-yl)-naphthalen-2-yl]-amino}-methyl)-phosphonic acid

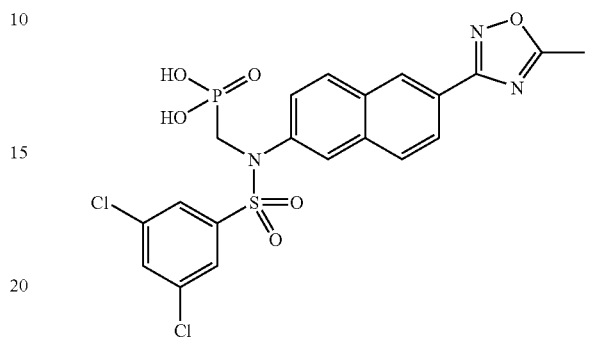

68 μl trimethylsilylbromide are added to 30 mg diethyl ({(3,5-dichloro-phenylsulphonyl)-[6-(5-methyl-[1,2,4]oxadiazol-3-yl)-naphthalen-2-yl]-amino}-methylphosphonate in 2 ml methylene chloride under an argon atmosphere. The reaction mixture is refluxed for three hours, combined with 5 ml of methanol and stirred for a further hour at ambient temperature. Then the mixture is evaporated down using the rotary evaporator and the flask residue is dried at 80° C. under a high vacuum.

Yield: 25 mg (92% of theory)

Mass spectrum (ESI$^-$): m/z=526, 528, 530 [M−H]$^-$

The following compounds are obtained analogously to Example 2:

(1) {[(5-benzylaminocarbonyl-naphthalen-2-yl)-(3,5-dichloro-phenylsulphonyl)-amino]-methyl}-phosphonic acid

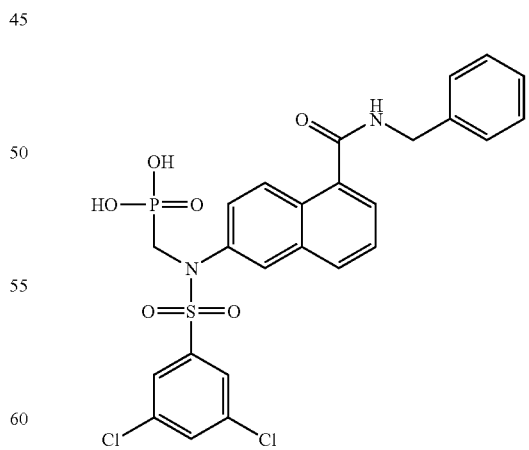

$R_f$ value: 0.36 (Reversed phase ready-made TLC plate (E. Merck), acetonitrile/water/trifluoroacetic acid=50:50:1)

(2) {[(5-benzylaminocarbonyl-naphthalen-1-yl)-(3,5-dichloro-phenylsulphonyl)-amino]-methyl}-phosphonic acid

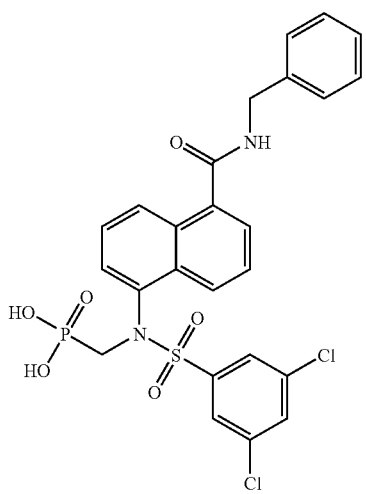

$R_f$ value: 0.55 (Reversed phase ready-made TLC plate (E. Merck), acetonitrile/water/trifluoroacetic acid=60:40:1)

Mass spectrum (ESI$^-$): m/z=577, 579, 581 [M−H]$^-$ (3) ({(3,5-dichloro-phenylsulphonyl)-[6-(phenylaminocarbonylamino)-naphthalen-2-yl]-amino}-methyl)-phosphonic acid

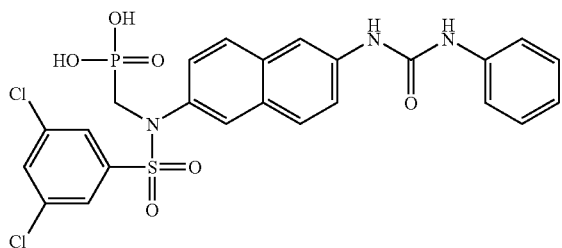

$R_f$ value: 0.50 (Reversed phase ready-made TLC plate (E. Merck), acetonitrile/water/trifluoroacetic acid=60:40:1)

Mass spectrum (ESI$^+$): m/z=580, 582, 584 [M+H]$^+$ (4) {[(6-benzylcarbonylamino-naphthalen-2-yl)-(3,5-dichloro-phenylsulphonyl)-amino]-methyl}-phosphonic acid

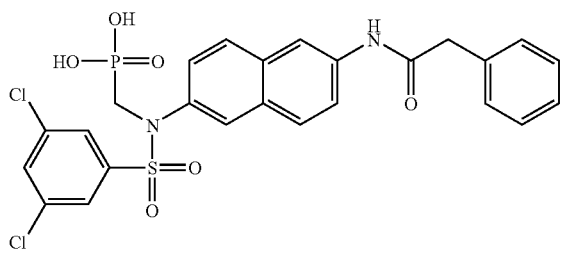

$R_f$ value: 0.60 (Reversed phase ready-made TLC plate (E. Merck), acetonitrile/water/trifluoroacetic acid=60:40:1)

(5) {[(3,5-dichloro-phenylsulphonyl)-naphthalen-1-yl-amino]-methyl}-phosphonic acid

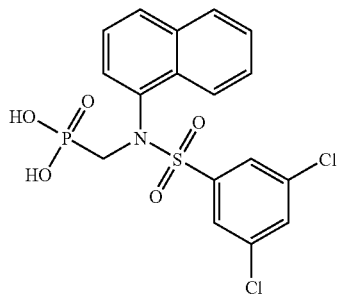

$R_f$ value: 0.63 (Reversed phase ready-made TLC plate (E. Merck), acetonitrile/water/trifluoroacetic acid=60:40:1)

(6) {[[5-(N-benzyl-N-methyl-aminocarbonyl)-naphthalen-1-yl]-(3,5-dichloro-phenylsulphonyl)-amino]-methyl}-phosphonic acid

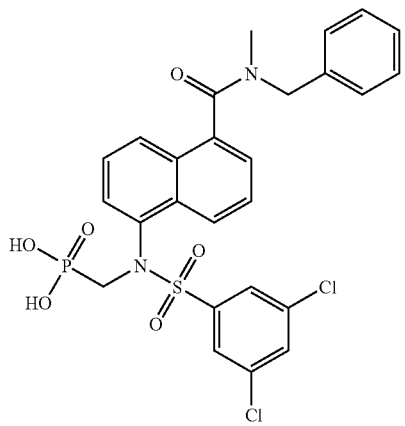

Mass spectrum (ESI$^-$): m/z=591, 593, 595 [M−H]$^-$ (7) ({(3,5-dichloro-phenylsulphonyl)-[5-(2-phenylethyl)aminocarbonyl-naphthalen-1-yl]-amino}-methyl)-phosphonic acid

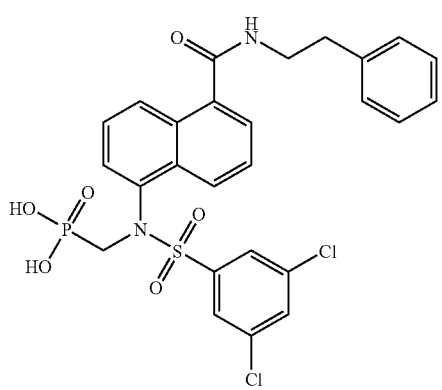

Mass spectrum (ESI$^+$): m/z=610, 612, 614 [M+NH$_4$]$^+$ (8) {[(3,5-dichloro-phenylsulphonyl)-(5-methylaminocarbonyl-naphthalen-2-yl)-amino]-methyl}-phosphonic acid

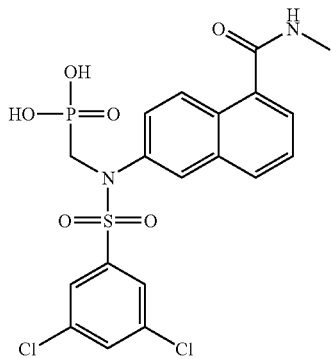

R_f value: 0.65 (Reversed phase ready-made TLC plate (E. Merck), acetonitrile/water/trifluoroacetic acid=60:40:1)
Mass spectrum (ESI⁻): m/z=501, 503, 505 [M−H]⁻

(9) ({(3,5-dichloro-phenylsulphonyl)-[5-(phenylaminocarbonylamino)-naphthalen-1-yl]-amino}-methyl)-phosphonic acid

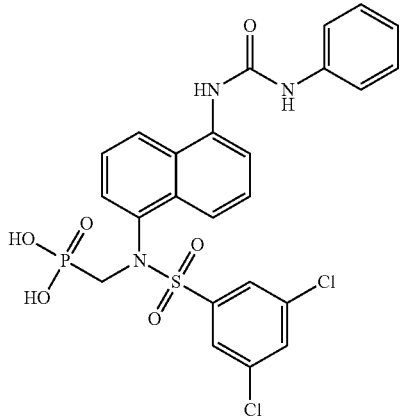

R_f value: 0.60 (Reversed phase ready-made TLC plate (E. Merck), acetonitrile/water/trifluoroacetic acid=60:40:1)
Mass spectrum (ESI⁻): m/z=578, 580, 582 [M−H]⁻

(10) {[(3,5-dichloro-phenylsulphonyl)-(6-pyrimidin-2-yl-naphthalen-2-yl)-amino]-methyl}-phosphonic acid

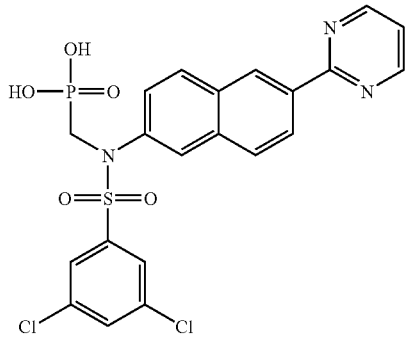

R_f value: 0.58 (Reversed phase ready-made TLC plate (E. Merck), acetonitrile/water/trifluoroacetic acid=60:40:1)
Mass spectrum (ESI⁻): m/z=522, 524, 526 [M−H]⁻

(11) ({[5-(4-cyano-benzylaminocarbonyl)-naphthalen-2-yl]-(3,5-dichloro-phenyl-sulphonyl)-amino}-methyl)-phosphonic acid

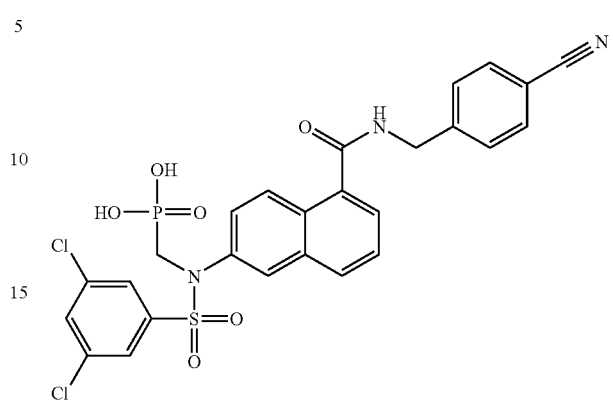

R_f value: 0.65 (Reversed phase ready-made TLC plate (E. Merck), acetonitrile/water/trifluoroacetic acid=60:40:1)
Mass spectrum (ESI⁺): m/z=604, 606, 608 [M+H]⁺

(12) {[(5-cyano-naphthalen-1-yl)-(3,5-dichloro-phenylsulphonyl)-amino]-methyl}-phosphonic acid

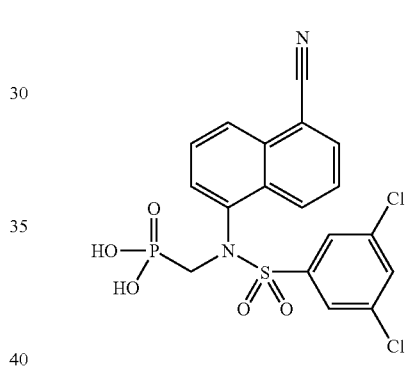

R_f value: 0.65 (Reversed phase ready-made TLC plate (E. Merck), acetonitrile/water/trifluoroacetic acid=60:40:1)
Mass spectrum (ESI⁺): m/z=471, 473, 475 [M+H]⁺

(13) {[(3,5-dichloro-phenylsulphonyl)-[5-(5-methyl-[1,2,4]oxadiazol-3-yl)-naphthalen-1-yl]-amino}-methyl)-phosphonic acid

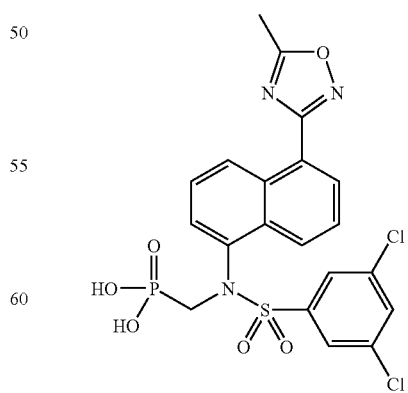

R_f value: 0.62 (Reversed phase ready-made TLC plate (E. Merck), acetonitrile/water/trifluoroacetic acid=60:40:1)
Mass spectrum (ESI⁺): m/z=528, 530, 532 [M+H]⁺

(14) {[(3,5-dichloro-phenylsulphonyl)-(2-methyl-naphthalen-1-yl)-amino]-methyl}-phosphonic acid

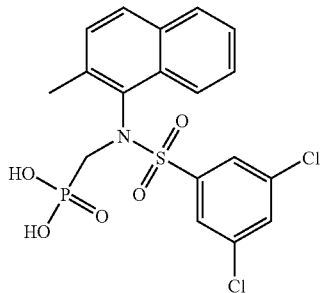

$R_f$ value: 0.55 (Reversed phase ready-made TLC plate (E. Merck), acetonitrile/water/trifluoroacetic acid=60:40:1)

(15) {[(3,5-dimethyl-phenylsulphonyl)-(5-methylaminocarbonyl-naphthalen-2-yl)-amino]-methyl}-phosphonic acid

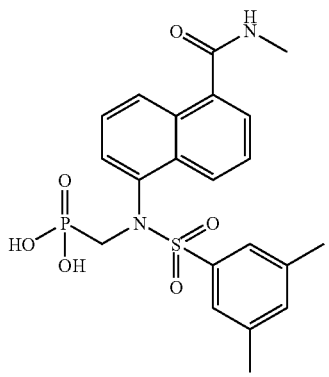

$R_f$ value: 0.75 (Reversed phase ready-made TLC plate (E. Merck), acetonitrile/water/trifluoroacetic acid=60:40:1)

Mass spectrum (ESI$^-$): m/z=461 [M−H]$^-$

(16) {[(3,5-dibromo-phenylsulphonyl)-naphthalen-1-yl-amino]-methyl}-phosphonic acid

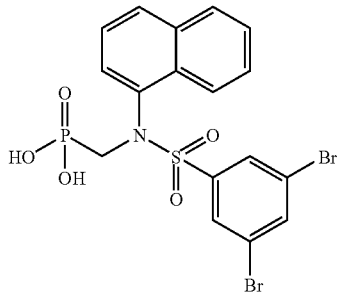

$R_f$ value: 0.60 (Reversed phase ready-made TLC plate (E. Merck), acetonitrile/water/trifluoroacetic acid=60:40:1)

Mass spectrum (ESI$^-$): m/z=532, 534, 536 [M−H]$^-$

(17) {[(3,5-dichloro-phenylsulphonyl)-(5-dimethylaminosulphonyl-naphthalen-1-yl)-amino]-methyl}-phosphonic acid

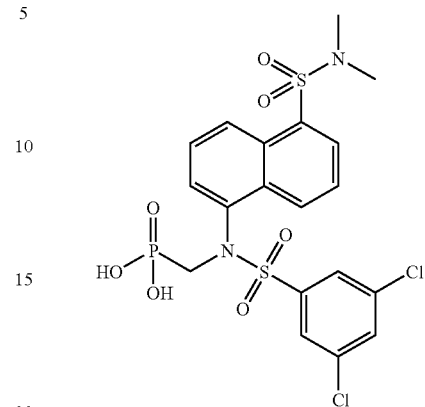

$R_f$ value: 0.63 (Reversed phase ready-made TLC plate (E. Merck), acetonitrile/water/trifluoroacetic acid=60:40:1)

Mass spectrum (ESI$^+$): m/z=553, 555, 557 [M+H]$^+$

(18) {[(3,5-dichloro-phenylsulphonyl)-quinolin-8-yl-amino]-methyl}-phosphonic acid

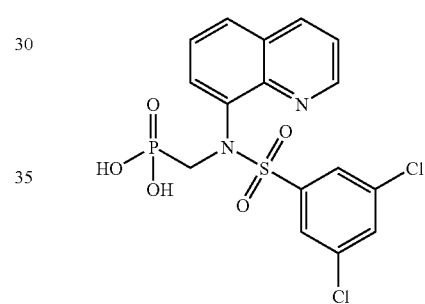

$R_f$ value: 0.40 (Reversed phase ready-made TLC plate (E. Merck), acetonitrile/water/trifluoroacetic acid=60:40:1)

Mass spectrum (ESI$^-$): m/z=445, 447, 449 [M−H]$^-$

(19) ({(3,5-dichloro-phenylsulphonyl)-[6-(5-methyl-[1,2,4]oxadiazol-3-yl)-naphthalen-1-yl]-amino}methyl)-phosphonic acid

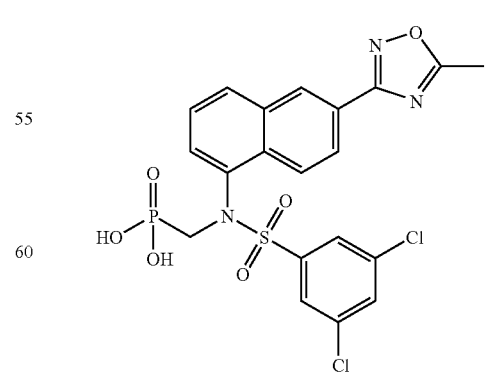

Mass spectrum (ESI$^-$): m/z=526, 528, 530 [M−H]$^-$

(20) {[(3,5-dichloro-phenylsulphonyl)-quinolin-5-yl-amino]-methyl}-phosphonic acid

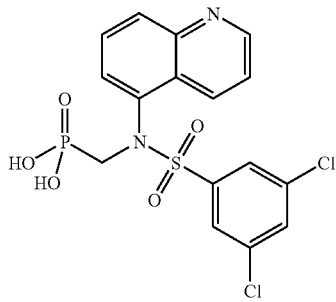

R$_f$ value: 0.38 (Reversed phase ready-made TLC plate (E. Merck), acetonitrile/water/trifluoroacetic acid=60:40:1)

Mass spectrum (ESI⁻): m/z=445, 447, 449 [M−H]⁻

(21) {[(3-chloro-5-methyl-phenylsulphonyl)-naphthalen-1-yl-amino]-methyl}-phosphonic acid

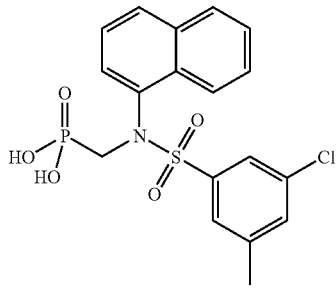

R$_f$ value: 0.62 (Reversed phase ready-made TLC plate (E. Merck), acetonitrile/water/trifluoroacetic acid=60:40:1)

Mass spectrum (ESI⁻): m/z=424, 426 [M−H]⁻

(22) {[(3,5-dimethyl-phenylsulphonyl)-naphthalen-1-yl-amino]-methyl}-phosphonic acid

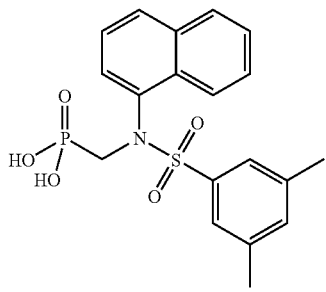

R$_f$ value: 0.62 (Reversed phase ready-made TLC plate (E. Merck), acetonitrile/water/trifluoroacetic acid=60:40:1)

Mass spectrum (ESI⁻): m/z=404 [M−H]⁻

(23) {[(3-bromo-5-chloro-phenylsulphonyl)-naphthalen-1-yl-amino]-methyl}-phosphonic acid

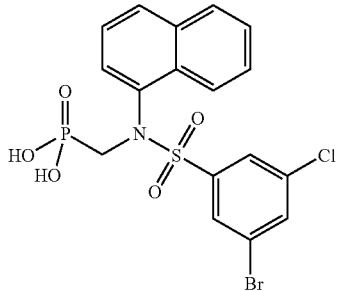

R$_f$ value: 0.60 (Reversed phase ready-made TLC plate (E. Merck), acetonitrile/water/trifluoroacetic acid=60:40:1)

Mass spectrum (ESI⁻): m/z=488, 490, 492 [M−H]⁻

(24) {[(3-chloro-5-fluoro-phenylsulphonyl)-naphthalen-1-yl-amino]-methyl}-phosphonic acid

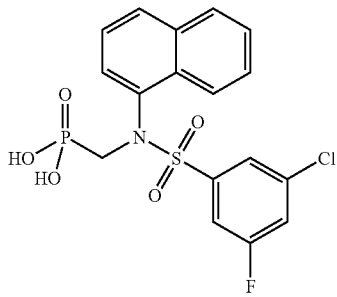

R$_f$ value: 0.58 (Reversed phase ready-made TLC plate (E. Merck), acetonitrile/water/trifluoroacetic acid=60:40:1)

Mass spectrum (ESI⁻): m/z=428, 430 [M−H]⁻

(25) {[(3,5-dichloro-phenylsulphonyl)-(3-methyl-naphthalen-2-yl)-amino]-methyl}-phosphonic acid

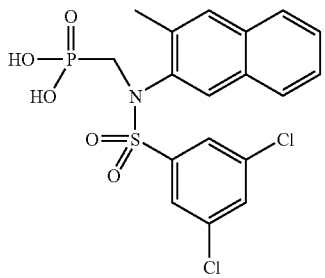

R$_f$ value: 0.50 (Reversed phase ready-made TLC plate (E. Merck), acetonitrile/water/trifluoroacetic acid=60:40:1)

Mass spectrum (ESI⁻): m/z=458, 460, 462 [M−H]⁻

(26) {[(3,5-dichloro-phenylsulphonyl)-quinoxalin-6-yl-amino]-methyl}-phosphonic acid

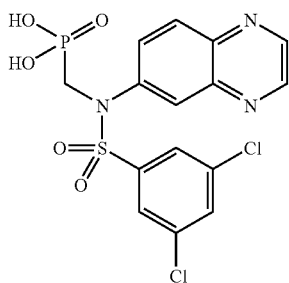

$R_f$ value: 0.78 (Reversed phase ready-made TLC plate (E. Merck), acetonitrile/water/trifluoroacetic acid=60:40:1)
Mass spectrum (ESI⁻): m/z=446, 448, 450 [M−H]⁻

(27) {[(3,5-dichloro-phenylsulphonyl)-quinolin-3-yl-amino]-methyl}-phosphonic acid

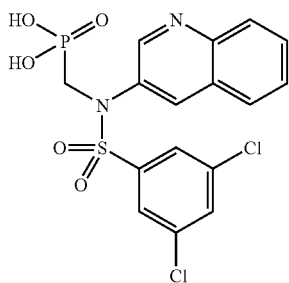

$R_f$ value: 0.74 (Reversed phase ready-made TLC plate (E. Merck), acetonitrile/water/trifluoroacetic acid=60:40:1)
Mass spectrum (ESI⁻): m/z=445, 447, 459 [M−H]⁻

(28) {[(3,5-dichloro-phenylsulphonyl)-quinolin-6-yl-amino]-methyl}-phosphonic acid

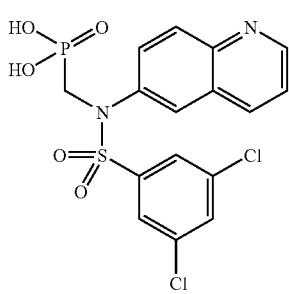

$R_f$ value: 0.76 (Reversed phase ready-made TLC plate (E. Merck), acetonitrile/water/trifluoroacetic acid=60:40:1)

(29) {[(3,5-dichloro-phenylsulphonyl)-(2-cyano-naphthalen-1-yl)-amino]-methyl}-phosphonic acid

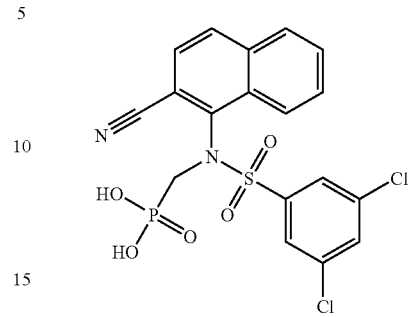

$R_f$ value: 0.60 (Reversed phase ready-made TLC plate (E. Merck), acetonitrile/water/trifluoroacetic acid=60:40:1)
Mass spectrum (ESI⁺): m/z=471, 473, 475 [M+H]⁺

(30) {[(3-bromo-5-methyl-phenylsulphonyl)-naphthalen-1-yl-amino]-methyl}-phosphonic acid

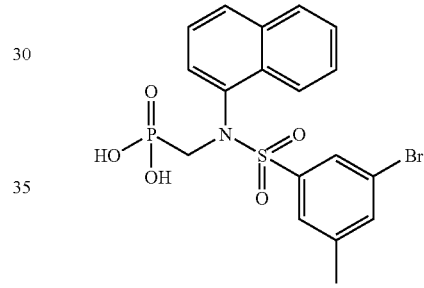

$R_f$ value: 0.60 (Reversed phase ready-made TLC plate (E. Merck), acetonitrile/water/trifluoroacetic acid=60:40:1)

(31) {[(3,5-dichloro-phenylsulphonyl)-(2-chloro-naphthalen-1-yl)-amino]-methyl}-phosphonic acid

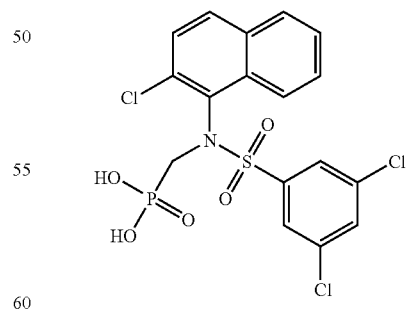

$R_f$ value: 0.50 (Reversed phase ready-made TLC plate (E. Merck), acetonitrile/water/trifluoroacetic acid=60:40:1)
Mass spectrum (ESI⁻): m/z=478, 480, 482, 484 [M−H]⁻

(32) {[(3,5-dichloro-phenylsulphonyl)-(5-methoxy-naphthalen-1-yl)-amino]-methyl}-phosphonic acid

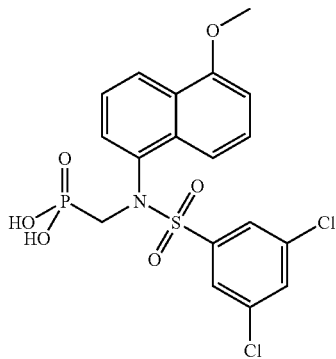

$R_f$ value: 0.53 (Reversed phase ready-made TLC plate (E. Merck), acetonitrile/water/trifluoroacetic acid=60:40:1)

Mass spectrum (ESI$^-$): m/z=474, 476, 478 [M−H]$^-$

(33) {[(3-chloro-5-trifluoromethyl-phenylsulphonyl)-naphthalen-1-yl-amino]-methyl}-phosphonic acid

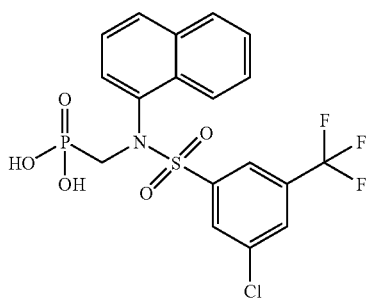

$R_f$ value: 0.60 (Reversed phase ready-made TLC plate (E. Merck), acetonitrile/water/trifluoroacetic acid=60:40:1)

Mass spectrum (ESI$^-$): m/z=478, 480 [M−H]$^-$

(34) {[(3,5-dichloro-phenylsulphonyl)-(4-methoxy-naphthalen-1-yl)-amino]-methyl}-phosphonic acid

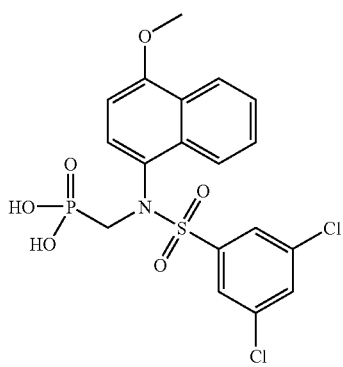

$R_f$ value: 0.62 (Reversed phase ready-made TLC plate (E. Merck), acetonitrile/water/trifluoroacetic acid=60:40:1)

Mass spectrum (ESI$^-$): m/z=474, 476, 478 [M−H]$^-$

(35) {[(3,5-dichloro-phenylsulphonyl)-(2-bromo-naphthalen-1-yl)-amino]-methyl}-phosphonic acid

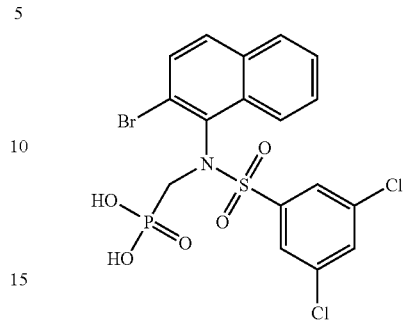

$R_f$ value: 0.54 (Reversed phase ready-made TLC plate (E. Merck), acetonitrile/water/trifluoroacetic acid=60:40:1)

Mass spectrum (ESI$^+$): m/z=524, 526, 528, 530 [M+H]$^+$

(36) {[(3,5-dichloro-phenylsulphonyl)-(7-methyl-quinolin-8-yl)-amino]-methyl}-phosphonic acid

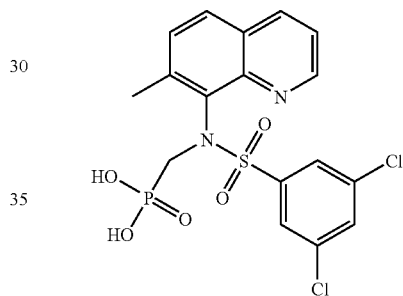

$R_f$ value: 0.45 (Reversed phase ready-made TLC plate (E. Merck), acetonitrile/water/trifluoroacetic acid=60:40:1)

Mass spectrum (ESI$^+$): m/z=461, 463, 465 [M+H]$^+$

(37) {[(3,5-dichloro-phenylsulphonyl)-(2-methyl-quinolin-8-yl)-amino]-methyl}-phosphonic acid

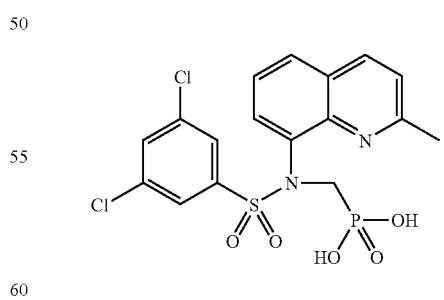

$^1$H-NMR (400 MHz, DMSO-d6) δ: 2.35 (s, 3H), 4.37 (d, 2H, J=10.6 Hz), 7.38 (d, 1H, J=8.3 Hz), 7.41 (d, 2H, J=1.9 Hz), 7.60 (t, 1H, J=7.8 Hz), 7.80 (dd, 1H, J=7.4 Hz, J=1.2 Hz), 7.87 (t, 1H, J=1.9 Hz), 8.00 (dd, 1H, J=8.1 Hz, J=1.2 Hz), 8.32 (d, 1H, J=8.3 Hz).

(38) ({(3,5-dichloro-phenylsulphonyl)-[2-(5-methyl-[1,2,4]oxadiazol-3-yl)-naphthalen-1-yl]-amino}methyl)-phosphonic acid

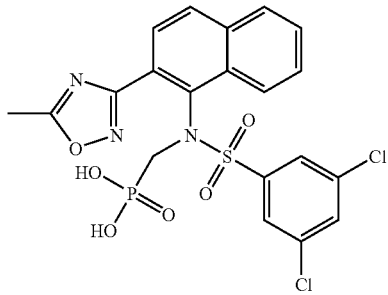

$R_f$ value: 0.55 (Reversed phase ready-made TLC plate (E. Merck), acetonitrile/water/trifluoroacetic acid=60:40:1)

Mass spectrum (ESI⁺): m/z=528, 530, 532 [M+H]⁺

(39) {[(2-aminocarbonyl-naphthalen-1-yl)-(3,5-dichloro-phenylsulphonyl)-amino]-methyl}-phosphonic acid

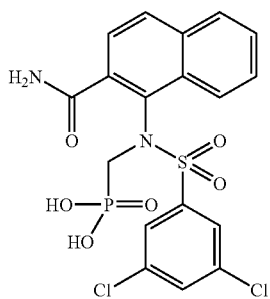

$R_f$ value: 0.65 (Reversed phase ready-made TLC plate (E. Merck), acetonitrile/water/trifluoroacetic acid=60:40:1)

Mass spectrum (ESI⁺): m/z=489, 491, 493 [M+H]⁺

(40) {[(3,5-dichloro-phenylsulphonyl)-(2-methoxy-naphthalen-1-yl)-amino]-methyl}-phosphonic acid

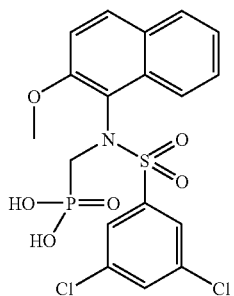

Mass spectrum (EI): m/z=475, 477, 479 [M+H]⁺

(41) {[(3,5-dichloro-phenylsulphonyl)-(2-ethynyl-naphthalen-1-yl)-amino]-methyl}-phosphonic acid

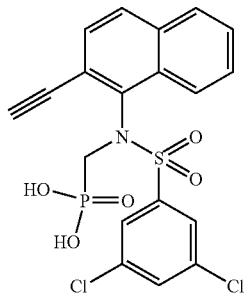

$R_f$ value: 0.60 (Reversed phase ready-made TLC plate (E. Merck), acetonitrile/water/trifluoroacetic acid=60:40:1)

Mass spectrum (ESI⁻): m/z=468, 470, 472 [M−H]⁻

(42) {[(3,5-dichloro-phenylsulphonyl)-(2-phenyl-ethynyl-naphthalen-1-yl)-amino]-methyl}-phosphonic acid

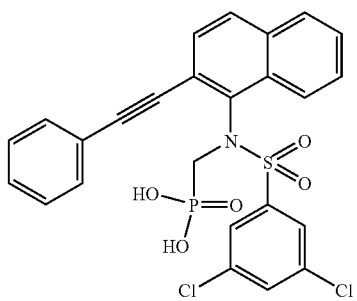

$R_f$ value: 0.45 (Reversed phase ready-made TLC plate (E. Merck), acetonitrile/water/trifluoroacetic acid=60:40:1)

Mass spectrum (ESI⁻): m/z=544, 546, 548 [M−H]⁻

(43) {[(3-chloro-5-cyano-phenylsulphonyl)-naphthalen-1-yl-amino]-methyl}-phosphonic acid

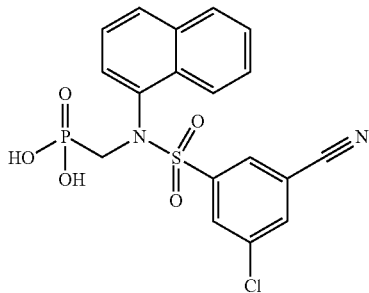

$R_f$ value: 0.65 (Reversed phase ready-made TLC plate (E. Merck), acetonitrile/water/trifluoroacetic acid=60:40:1)

(44) {[(2-benzothiazol-2-yl-naphthalen-1-yl)-(3,5-dichloro-phenylsulphonyl)-amino]-methyl}-phosphonic acid

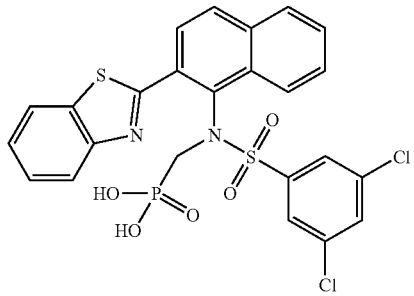

R*f* value: 0.40 (Reversed phase ready-made TLC plate (E. Merck), acetonitrile/water/trifluoroacetic acid=60:40:1)

(45) {[(3,5-dichloro-4-fluoro-phenylsulphonyl)-naphthalen-1-yl-amino]-methyl}-phosphonic acid

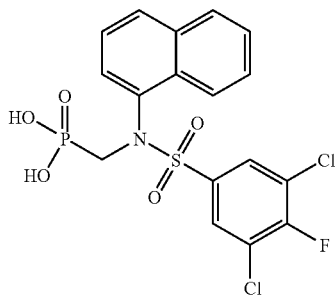

R*f* value: 0.62 (Reversed phase ready-made TLC plate (E. Merck), acetonitrile/water/trifluoroacetic acid=60:40:1)
Mass spectrum (ESI⁻): m/z=462, 464, 466 [M−H]⁻

(46) {[(2-benzylaminocarbonyl-naphthalen-1-yl)-(3,5-dichloro-phenylsulphonyl)-amino]-methyl}-phosphonic acid

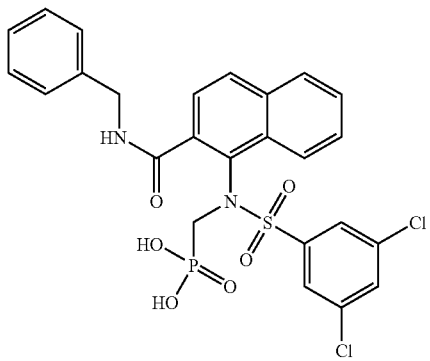

R*f* value: 0.38 (Reversed phase ready-made TLC plate (E. Merck), acetonitrile/water/trifluoroacetic acid=60:40:1)
Mass spectrum (ESI⁺): m/z=579, 581, 583 [M+H]⁺

(47) {[(2-pyrrolidin-1-ylcarbonyl-naphthalen-1-yl)-(3,5-dichloro-phenylsulphonyl)-amino]-methyl}-phosphonic acid

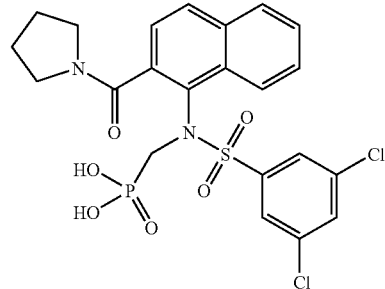

R*f* value: 0.45 (Reversed phase ready-made TLC plate (E. Merck), acetonitrile/water/trifluoroacetic acid=60:40:1)
Mass spectrum (ESI⁺): m/z=543, 545, 547 [M+H]⁺

(48) {[(2-benzoxazol-2-yl-naphthalen-1-yl)-(3,5-dichloro-phenylsulphonyl)-amino]-methyl}-phosphonic acid

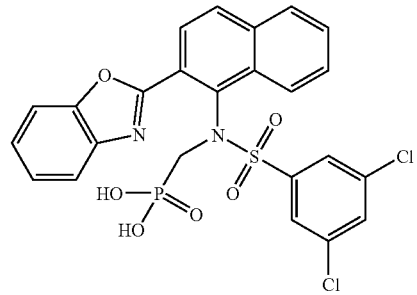

R*f* value: 0.45 (Reversed phase ready-made TLC plate (E. Merck), acetonitrile/water/trifluoroacetic acid=60:40:1)
Mass spectrum (ESI⁺): m/z=563, 565, 567 [M+H]⁺

(49) {[(2-dimethylaminocarbonyl-naphthalen-1-yl)-(3,5-dichloro-phenylsulphonyl)-amino]-methyl}-phosphonic acid

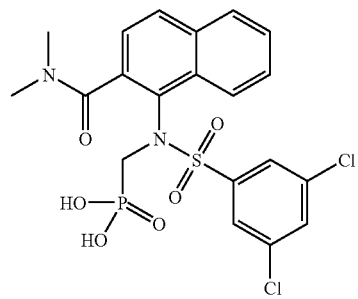

R*f* value: 0.50 (Reversed phase ready-made TLC plate (E. Merck), acetonitrile/water/trifluoroacetic acid=60:40:1)
Mass spectrum (ESI⁺): m/z=517, 519, 521 [M+H]⁺

(50) {[(2-phenylcarbonyl-naphthalen-1-yl)-(3,5-dichloro-phenylsulphonyl)-amino]-methyl}-phosphonic acid

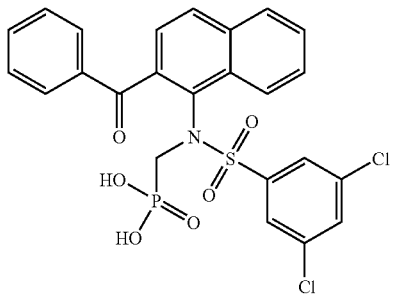

$R_f$ value: 0.45 (Reversed phase ready-made TLC plate (E. Merck), acetonitrile/water/trifluoroacetic acid=60:40:1)

Mass spectrum (ESI$^+$): m/z=550, 552, 554 [M+H]$^+$

(51) {[(3-chloro-5-nitro-phenylsulphonyl)-naphthalen-1-yl-amino]-methyl}-phosphonic acid

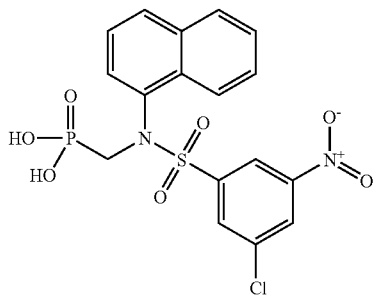

$R_f$ value: 0.55 (Reversed phase ready-made TLC plate (E. Merck), acetonitrile/water/trifluoroacetic acid=60:40:1)

Mass spectrum (ESI$^+$): m/z=457, 459 [M+H]$^+$

(52) {[(3-amino-5-chloro-phenylsulphonyl)-naphthalen-1-yl-amino]-methyl}-phosphonic acid

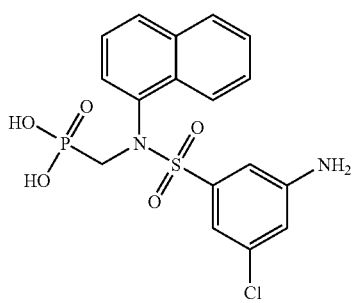

$R_f$ value: 0.65 (Reversed phase ready-made TLC plate (E. Merck), acetonitrile/water/trifluoroacetic acid=60:40:1)

Mass spectrum (ESI$^-$): m/z=425, 427 [M−H]$^-$

(53) {[(3,5-dichloro-phenylsulphonyl)-(3-methyl-cinnolin-5-yl)-amino]-methyl}-phosphonic acid

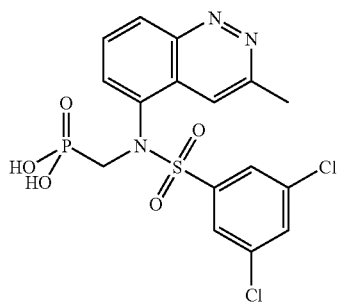

Mass spectrum (ESI$^+$): m/z=462, 464, 466 [M+H]$^+$

(54) {[(3,5-dichloro-phenylsulphonyl)-(3-methyl-isoquinolin-5-yl)-amino]-methyl}-phosphonic acid

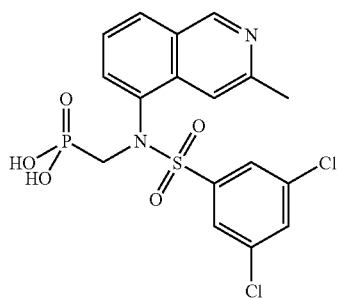

Mass spectrum (ESI$^+$): m/z=461, 463, 465 [M+H]$^+$

(55) {[(3,5-dichloro-phenylsulphonyl)-quinoxalin-5-yl-amino]-methyl}-phosphonic acid

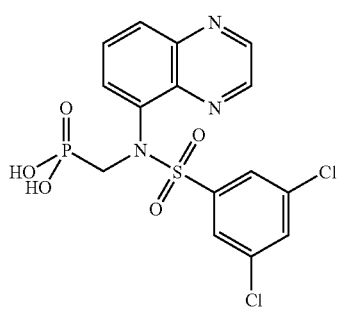

$R_f$ value: 0.25 (silica gel, methylene chloride/methanol=9:1)

Mass spectrum (ESI$^+$): m/z=448, 450, 452 [M+H]$^+$

(56) {[(3,5-dichloro-phenylsulphonyl)-quinoline-7-yl-amino]-methyl}-phosphonic acid

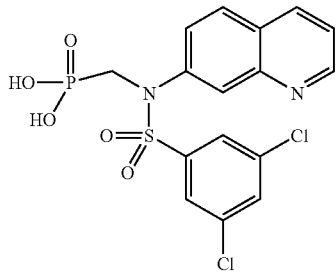

Mass spectrum (ESI⁺): m/z=447, 449, 451 [M+H]⁺

(57) {[(3,5-dichloro-phenylsulphonyl)-(3-methyl-quinolin-5-yl)-amino]-methyl}-phosphonic acid

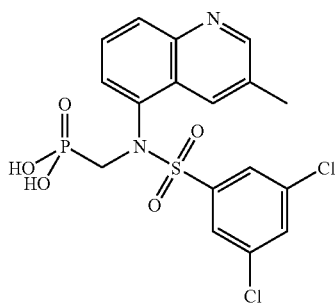

Mass spectrum (ESI⁺): m/z=461, 463, 465 [M+H]⁺

(58) {[(3,5-dichloro-phenylsulphonyl)-(4-dimethylamino-quinazolin-8-yl)-amino]-methyl}-phosphonic acid

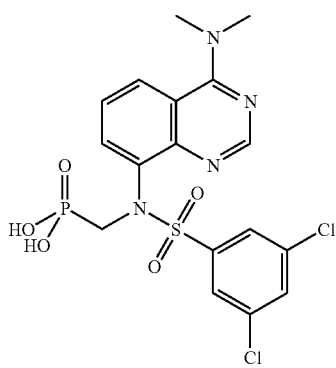

$R_f$ value: 0.47 (silica gel, methylene chloride/methanol=9:1)

Mass spectrum (ESI⁺): m/z=491, 493, 495 [M+H]⁺

(59) {[(3,5-dichloro-phenylsulphonyl)-quinazolin-8-yl-amino]-methyl}-phosphonic acid

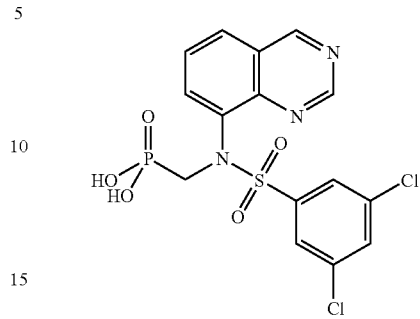

Mass spectrum (ESI⁻): m/z=446, 448, 450 [M−H]⁻

Example 3

{[(3,5-dichloro-phenylsulphonyl)-(5-methylaminocarbonyl-naphthalen-2-yl)-amino]-methyl}-phosphonic acid bis(2,2-dimethyl-propionyloxymethoxy) ester

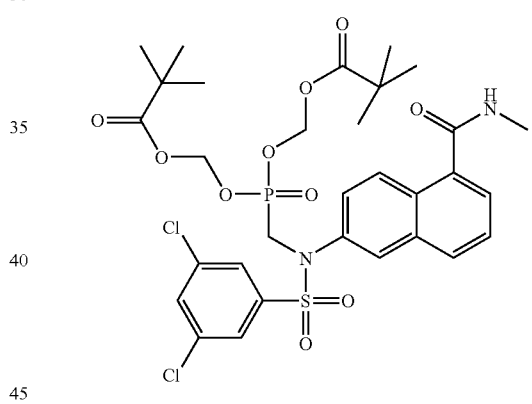

616 mg silver carbonate and 0.81 ml chloromethyl pivalate are added to 500 mg {[(3,5-dichloro-phenylsulphonyl)-(5-methylaminocarbonyl-naphthalen-2-yl)-amino]-methyl}-phosphonic acid in 35 ml acetone and 15 ml acetonitrile at 55° C. The reaction mixture is stirred overnight at 55° C., diluted with 20 ml acetonitrile and stirred for a further 22 hours. For working up the reaction mixture is diluted with ethyl acetate, filtered and evaporated down. The residue is taken up in ethyl acetate, washed with dilute sodium carbonate solution, water and saturated sodium chloride solution, dried on magnesium sulphate and evaporated down. The flask residue is chromatographed through a silica gel column with ethyl acetate as eluant.

Yield: 397 mg (52% of theory)

$R_f$ value: 0.20 (Reversed phase ready-made TLC plate (E. Merck), acetonitrile/water/trifluoroacetic acid=60:40:1)

Mass spectrum (ESI⁺): m/z=748, 750, 752 [M+NH₄]⁺

The following compounds are obtained analogously to Example 3:

(1) {[(3,5-dichloro-phenylsulphonyl)-(5-methylaminocarbonyl-naphthalen-2-yl)-amino]-methyl}-phosphonic acid-mono-(2,2-dimethyl-propionyloxymethoxy)-ester

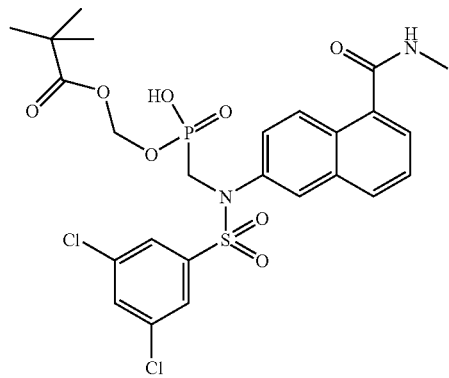

R$_f$ value: 0.55 (Reversed phase ready-made TLC plate (E. Merck), acetonitrile/water/trifluoroacetic acid=60:40:1)

Mass spectrum (ESI$^-$): m/z=615, 617, 619 [M–H]$^-$ (2) {[(3,5-dichloro-phenylsulphonyl)-(5-methylaminocarbonyl-naphthalen-2-yl)-amino]-methyl}-phosphonic acid-bis(isopropyloxycarbonyloxymethyl)-ester

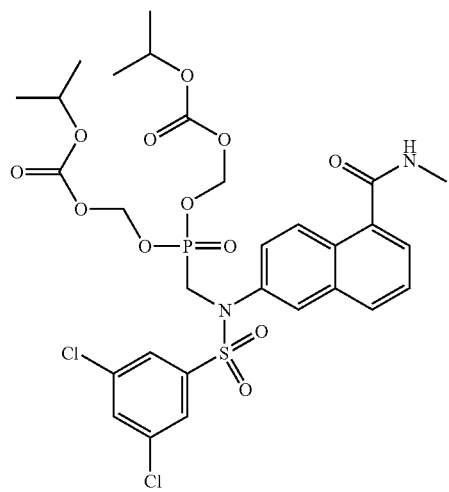

(The reaction is carried out with isopropyl chloromethylcarbonate.)

R$_f$ value: 0.68 (silica gel, ethyl acetate)

Mass spectrum (ESI$^+$): m/z=735, 737, 739 [M+H]$^+$ (3) {[(3-bromo-5-chloro-phenylsulphonyl)-naphthalen-1-yl-amino]-methyl}-phosphonic acid-bis(isopropyloxycarbonyloxymethyl)-ester

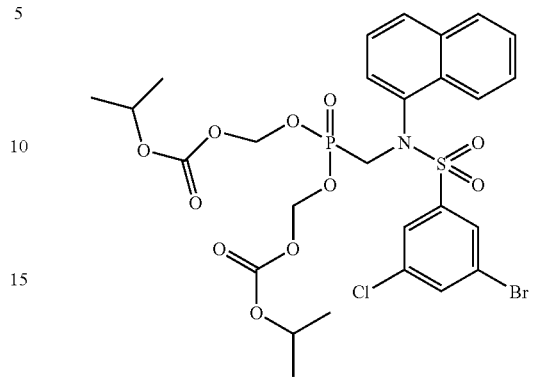

(The reaction is carried out with isopropylchloromethylcarbonate.)

R$_f$ value: 0.40 (silica gel, petroleum ether/ethyl acetate=2:1)

Mass spectrum (ESI$^+$): m/z=739, 741, 743 [M+NH$_4$]$^+$ (4) {[(3-bromo-5-chloro-phenylsulphonyl)-naphthalen-1-yl-amino]-methyl}-phosphonic acid-bis(2,2-dimethyl-propionyloxymethoxy)-ester

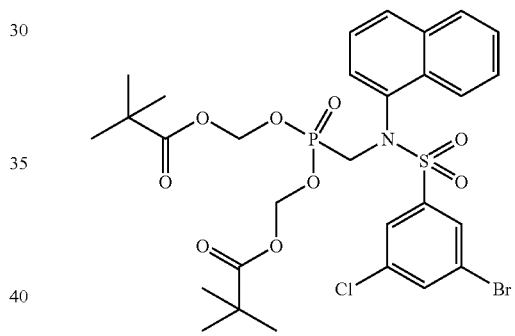

R$_f$ value: 0.60 (silica gel, petroleum ether/ethyl acetate=2:1)

Mass spectrum (ESI$^+$): m/z=735, 737, 739 [M+NH$_4$]$^+$ (5) {[(3,5-dichloro-phenylsulphonyl)-quinolin-6-yl-amino]-methyl}-phosphonic acid-bis(2,2-dimethyl-propionyloxymethoxy)-ester

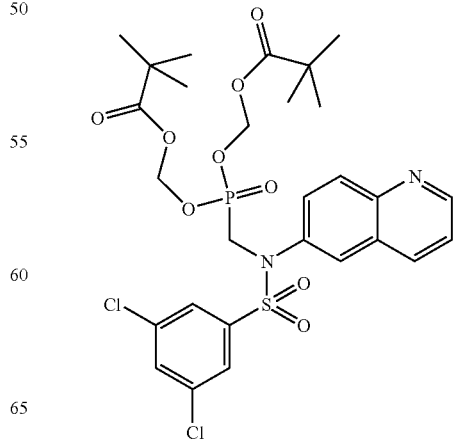

$R_f$ value: 0.45 (silica gel, petroleum ether/ethyl acetate=1:2)

Mass spectrum (ESI$^+$): m/z=675, 677, 679 [M+H]$^+$ (6) {[(3,5-dichloro-phenylsulphonyl)-quinolin-6-yl-amino]-methyl}-phosphonic acid-bis(isopropyloxy-carbonyloxymethyl)-ester

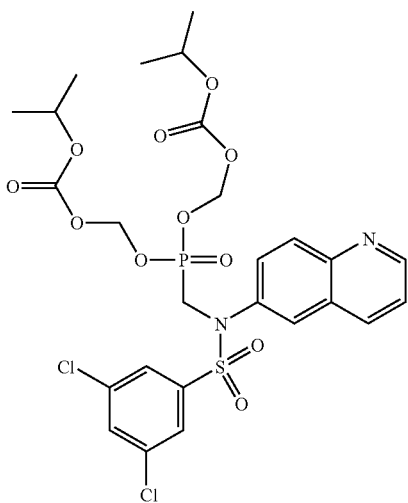

(The reaction is carried out with isopropyl chloromethyl-carbonate.)

$R_f$ value: 0.65 (silica gel, ethyl acetate)
Mass spectrum (ESI$^+$): m/z=679, 681, 683 [M+H]$^+$ Example 4

{[(3-bromo-5-chloro-phenylsulphonyl)-naphthalen-1-yl-amino]-methyl}-[N,N'-bis((S)-1-ethoxycarbo-nyl)ethyl-phosphonamide

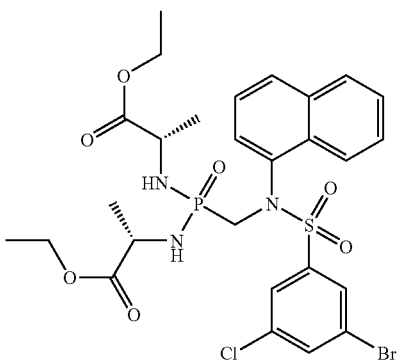

2.19 ml of thionyl chloride and 50 μl N,N-dimethylformamide are added to 2.45 g of 3-bromo-5-chloro-phenylsulpho-nyl)-naphthalen-1-yl-amino]-methyl}-phosphonic acid in 25 ml of dichloroethane under a nitrogen atmosphere. The reaction mixture is refluxed for 2.5 hours and then evaporated down in vacuo. The flask residue is taken up in 10 ml methylene chloride and while cooling with an ice bath it is combined with 1.69 g L-alanine-ethylester-hydrochloride as well as 2.23 ml triethylamine, dissolved in 15 ml methylene chloride. The reaction mixture is heated to ambient temperature overnight. For working up it is diluted with methylene chloride, washed with water and saturated sodium chloride solution, dried on magnesium sulphate and evaporated down. The flask residue is chromatographed through a silica gel column with cyclohexane/ethyl acetate (40:60 to 20:80) as eluant.

Yield: 1.74 g (51% of theory)
Mass spectrum (ESI$^+$): m/z=688, 690, 692 [M+H]$^+$
$R_f$ value: 0.32 (silica gel, petroleum ether/ethyl acetate=1:2)

Example 5

Coated Tablets Containing 75 mg of Active Substance
1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| die: | 9 mm, convex |

The tablet cores thus produced are coated with a film consisting essentially of hydroxypropylmethylcellulose. The finished film-coated tablets are polished with beeswax.

| | |
|---|---|
| Weight of coated tablet: | 245 mg. |

Example 6

Tablets Containing 100 mg of Active Substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

Example 7

Tablets Containing 150 mg of Active Substance
Composition:
1 tablet contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

Example 8

Hard gelatine capsules containing 150 mg of active substance
1 capsule contains:

| | |
|---|---|
| active substance | 50.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

| | |
|---|---|
| Capsule filling: | approx. 320 mg |
| Capsule shell: | size 1 hard gelatine capsule. |

Example 9

Suppositories containing 150 mg of active substance
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example 10

Suspension containing 50 mg of active substance
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavouring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

Example 11

Ampoules containing 10 mg active substance
Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

Example 12

Ampoules containing 50 mg of active substance
Composition:

| | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

The invention claimed is:
1. A compound of formula (I)

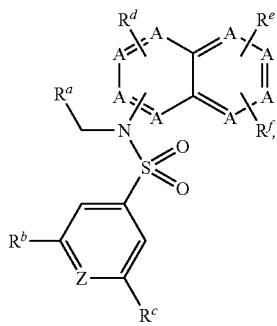

(I)

wherein the bicyclic heteroaromatic group of general formula (II)

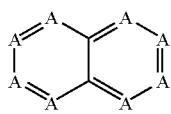

(II)

denotes naphthalene, quinoline, isoquinoline, quinazoline, quinoxaline or cinnoline, $R^a$ denotes a group of formula $PO(OH)_2$, wherein one or two OH groups in each case may be replaced by
  a $C_{1-2}$-alkoxy group, which is substituted in the alkyl moiety by a $C_{1-4}$-alkyl-carbonyloxy or $C_{1-4}$-alkoxy-carbonyloxy group, or by
  a $C_{1-3}$-alkylamino group, which is substituted in the alkyl moiety by a $C_{1-3}$-alkoxy-carbonyl group, $R^b$ and $R^c$ independently of one another denote fluorine, chlorine, bromine, cyano, $C_{1-2}$-alkyl, ethynyl, trifluoromethyl, methoxy, amino or nitro, Z denotes CH or CF and $R^d$ denotes H, fluorine, chlorine, bromine, cyano, $C_{1-3}$-alkyl, $C_{2-3}$-alkynyl, aryl, heteroaryl, aryl-$C_{2-3}$-alkynyl, $C_{1-3}$-alkoxy, arylcarbonyl, di-($C_{1-3}$-alkyl)-aminosulphonyl,
  5- to 7-membered cycloalkyleneimino-carbonyl, aminocarbonyl, wherein one or two hydrogen atoms independently of one another may be replaced in each case by a $C_{1-3}$-alkyl or aryl-($C_{1-3}$-alkyl)-group, or amino, which may be substituted by one or two $C_{1-3}$-alkyl groups or an aryl-$C_{1-3}$-alkylcarbonyl or arylaminocarbonyl group,
  while by an aryl group is meant a phenyl group which may optionally be substituted by a cyano group,
  and by a heteroaryl group is meant a 5-methyl-[1,2,4]oxadiazolyl, benzoxazolyl, benzothiazolyl or pyrimidinyl group, $R^e$ has the meaning given hereinbefore for $R^d$ with the proviso that at least one of the groups $R^d$ and $R^e$ must be H or $C_{1-3}$-alkyl, and $R^f$ denotes H or $C_{1-3}$-alkyl, or a physiologically acceptable salts thereof.

2. The compound of formula (I) according to claim 1, wherein the bicyclic heteroaromatic group of formula (II) denotes naphthalene, quinoline, quinazoline, quinoxaline or cinnoline, $R^a$ denotes a group of formula $PO(OH)_2$, wherein one or two OH groups may be replaced in each case by a tert-butyl-carbonyloxy-methoxy, iso-propyloxy-carbonyloxy-methoxy or 1-ethoxycarbonyl-ethylamino group, $R^b$ and $R^c$ independently of one another denote fluorine, chlorine, bromine, $C_{1-2}$-alkyl or trifluoromethyl, Z denotes CH, $R^d$ denotes hydrogen,
  or, if $R^e$ denotes hydrogen, $R^d$ may also denote a group selected from among chlorine, bromine, cyano, $C_{1-2}$-alkyl, ethynyl, 2-phenyl-ethynyl, $C_{1-2}$-alkoxy, 5-methyl-[1,2,4]oxadiazolyl, benzoxazolyl, benzothiazolyl, phenylcarbonyl, pyrrolidinylcarbonyl and
  aminocarbonyl, wherein a hydrogen atom may be replaced by a methyl or benzyl group and optionally another hydrogen atom may be replaced by a further methyl group, $R^e$ denotes hydrogen,
  or, if $R^d$ denotes hydrogen, $R^d$ may also denote a group selected from among cyano, $C_{1-2}$-alkyl, $C_{1-2}$-alkoxy, dimethylaminosulphonyl, 5-methyl-[1,2,4]oxadiazolyl, pyrimidinyl,
  amino, which is substituted by one or two methyl groups or a benzylcarbonyl or phenylaminocarbonyl group, and
  aminocarbonyl, wherein a hydrogen atom may be replaced by a methyl group and the other hydrogen atom may optionally be replaced by a phenyl-($C_{1-2}$-alkyl) group, which may be substituted in the phenyl moiety by a cyano group, and $R^f$ denotes H, or a physiologically acceptable salt thereof.

3. The compound according to claim 1 selected from:
(1) {[(3,5-dichloro-phenylsulphonyl)-naphthalen-2-yl-amino]-methyl}-phosphonic acid,
(2) ({(3,5-dichloro-phenylsulphonyl)-[6-(5-methyl-[1,2,4]oxadiazol-3-yl)-naphthalen-2-yl]-amino}-methyl)-phosphonic acid,
(3) {[(5-benzylaminocarbonyl-naphthalen-2-yl)-(3,5-dichloro-phenylsulphonyl)-amino]-methyl}-phosphonic acid, (4) {[(5-benzylaminocarbonyl-naphthalen-1-yl)-(3,5-dichloro-phenylsulphonyl)-amino]-methyl}-phosphonic acid,
(5) ({(3,5-dichloro-phenylsulphonyl)-[6-(phenylaminocarbonylamino)-naphthalen-2-yl]-amino}-methyl)-phosphonic acid,
(6) {[(6-benzylcarbonylamino-naphthalen-2-yl)-(3,5-dichloro-phenylsulphonyl)-amino]-methyl}-phosphonic acid,
(7) {[(3,5-dichloro-phenylsulphonyl)-naphthalen-1-yl-amino]-methyl}-phosphonic acid,
(8) {[[5-(N-benzyl-N-methyl-aminocarbonyl)-naphthalen-1-yl]-(3,5-dichloro-phenylsulphonyl)-amino]-methyl}-phosphonic acid,
(9) {[3,5-dichloro-phenylsulphonyl)-(5-phenylethylaminocarbonyl-naphthalen-1-yl)-amino]-methyl}-phosphonic acid,
(10) {[(3,5-dichloro-phenylsulphonyl)-(5-methylaminocarbonyl-naphthalen-2-yl)-amino]-methyl}-phosphonic acid,
(11) ({(3,5-dichloro-phenylsulphonyl)-[5-(phenylaminocarbonylamino)-naphthalen-1-yl]-amino}-methyl)-phosphonic acid,
(12) {[(3,5-dichloro-phenylsulphonyl)-(6-pyrimidin-2-yl-naphthalen-2-yl)-amino]-methyl}-phosphonic acid,
(13) ({[5-(4-cyano-benzylaminocarbonyl)-naphthalen-2-yl]-(3,5-dichloro-phenyl-sulphonyl)-amino}-methyl)-phosphonic acid,
(14) {[(5-cyano-naphthalen-1-yl)-(3,5-dichloro-phenylsulphonyl)-amino]-methyl}-phosphonic acid,
(15) {[(3,5-dichloro-phenylsulphonyl)-[5-(5-methyl-[1,2,4]oxadiazol-3-yl)-naphthalen-1-yl]-amino}-methyl)-phosphonic acid,
(16) {[(3,5-dibromo-phenylsulphonyl)-naphthalen-1-yl-amino]-methyl}-phosphonic acid,
(17) {[(3,5-dichloro-phenylsulphonyl)-(5-dimethylaminosulphonyl-naphthalen-1-yl)-amino]-methyl}-phosphonic acid,
(18) {[(3,5-dichloro-phenylsulphonyl)-quinolin-8-yl-amino]-methyl}-phosphonic acid,
(19) ({(3,5-dichloro-phenylsulphonyl)-[6-(5-methyl-[1,2,4]oxadiazol-3-yl)-naphthalen-1-yl]-amino}-methyl)-phosphonic acid,
(20) {[(3,5-dichloro-phenylsulphonyl)-quinolin-5-yl-amino]-methyl}-phosphonic acid,
(21) {[(3-chloro-5-methyl-phenylsulphonyl)-naphthalen-1-yl-amino]-methyl}-phosphonic acid,
(22) {[(3-bromo-5-chloro-phenylsulphonyl)-naphthalen-1-yl-amino]-methyl}-phosphonic acid,
(23) {[(3,5-dichloro-phenylsulphonyl)-(3-methyl-naphthalen-2-yl)-amino]-methyl}-phosphonic acid,
(24) {[(3,5-dichloro-phenylsulphonyl)-quinoxalin-6-yl-amino]-methyl}-phosphonic acid,
(25) {[(3,5-dichloro-phenylsulphonyl)-quinolin-3-yl-amino]-methyl}-phosphonic acid,
(26) {[(3,5-dichloro-phenylsulphonyl)-quinolin-6-yl-amino]-methyl}-phosphonic acid,
(27) {[(3,5-dichloro-phenylsulphonyl)-(2-cyano-naphthalen-1-yl)-amino]-methyl}-phosphonic acid,
(28) {[(3-bromo-5-methyl-phenylsulphonyl)-naphthalen-1-yl-amino]-methyl}-phosphonic acid,
(29) {[(3,5-dichloro-phenylsulphonyl)-(2-chloro-naphthalen-1-yl)-amino]-methyl}-phosphonic acid,
(30) {[(3,5-dichloro-phenylsulphonyl)-(5-methoxy-naphthalen-1-yl)-amino]-methyl}-phosphonic acid,
(31) {[(3,5-dichloro-phenylsulphonyl)-(4-methoxy-naphthalen-1-yl)-amino]-methyl}-phosphonic acid,
(32) {[(3,5-dichloro-phenylsulphonyl)-(2-bromo-naphthalen-1-yl)-amino]-methyl}-phosphonic acid,
(33) {[(3,5-dichloro-phenylsulphonyl)-(7-methyl-quinolin-8-yl)-amino]-methyl}-phosphonic acid,
(34) {[(3,5-dichloro-phenylsulphonyl)-(2-methyl-quinolin-8-yl)-amino]-methyl}-phosphonic acid,
(35) {[(3,5-dichloro-phenylsulphonyl)-(2-methoxy-naphthalen-1-yl)-amino]-methyl}-phosphonic acid,
(36) {[(3,5-dichloro-phenylsulphonyl)-(2-ethynyl-naphthalen-1-yl)-amino]-methyl}-phosphonic acid,
(37) {[(2-benzylaminocarbonyl-naphthalen-1-yl)-(3,5-dichloro-phenylsulphonyl)-amino]-methyl}-phosphonic acid,
(38) {[(3,5-dichloro-phenylsulphonyl)-(5-methylaminocarbonyl-naphthalen-2-yl)-amino]-methyl}-phosphonic acid-bis(2,2-dimethyl-propionyloxymethoxy)-ester,
(39) {[(3,5-dichloro-phenylsulphonyl)-(5-methylaminocarbonyl-naphthalen-2-yl)-amino]-methyl}-phosphonic acid-mono-(2,2-dimethyl-propionyloxymethoxy)-ester,
(40) {[(3,5-dichloro-phenylsulphonyl)-(5-methylaminocarbonyl-naphthalen-2-yl)-amino]-methyl}-phosphonic acid-bis(isopropyloxycarbonyloxymethyl)-ester,
(41) {[(3-bromo-5-chloro-phenylsulphonyl)-naphthalen-1-yl-amino]-methyl}-phosphonic acid-bis(isopropyloxycarbonyloxymethyl)-ester,
(42) {[(3-bromo-5-chloro-phenylsulphonyl)-naphthalen-1-yl-amino]-methyl}-phosphonic acid-bis(2,2-dimethyl-propionyloxymethoxy)-ester,
(43) {[(3,5-dichloro-phenylsulphonyl)-(3-methyl-cinnolin-5-yl)-amino]-methyl}-phosphonic acid,
(44) {[(3,5-dichloro-phenylsulphonyl)-quinoxalin-5-yl-amino]-methyl}-phosphonic acid,
(45) {[(3,5-dichloro-phenylsulphonyl)-quinoline-7-yl-amino]-methyl}-phosphonic acid,
(46) {[(3,5-dichloro-phenylsulphonyl)-(3-methyl-quinolin-5-yl)-amino]-methyl}-phosphonic acid,
(47) {[(3,5-dichloro-phenylsulphonyl)-(4-dimethylamino-quinazolin-8-yl)-amino]-methyl}-phosphonic acid,
(48) {[(3,5-dichloro-phenylsulphonyl)-quinolin-6-yl-amino]-methyl}-phosphonic acid-bis(2,2-dimethyl-propionyloxymethoxy)-ester,
(49) {[3,5-dichloro-phenylsulphonyl)-quinolin-6-yl-amino]-methyl}-phosphonic acid-bis(isopropyloxycarbonyloxymethyl)-ester or
(50) {[(3,5-dichloro-phenylsulphonyl)-quinazolin-8-yl-amino]-methyl}-phosphonic acid or a physiologically acceptable salt of any of the foregoing compounds.

4. A pharmaceutically acceptable composition comprising a compound according to claim 1 together with one or more inert carriers and/or diluents.

* * * * *